(12) United States Patent
Fischer et al.

(10) Patent No.: US 8,901,038 B2
(45) Date of Patent: Dec. 2, 2014

(54) BIPHENYL-SUBSTITUTED CYCLIC KETOENOLS

(75) Inventors: Reiner Fischer, Monheim (DE); Stefan Lehr, Liederbach (DE); Isolde Häuser-Hahn, Leverkusen (DE); Christopher Hugh Rosinger, Hofheim (DE); Chieko Ueno, Frankfurt (DE); Arnd Voerste, Köln (DE); Elmar Gatzweiler, Büdingen (DE); Ines Heinemann, Hofheim (DE); Ulrich Görgens, Ratingen (DE)

(73) Assignee: Bayer CropScience AG, Monheim (DE)

( * ) Notice: Subject to any disclaimer, the term of this patent is extended or adjusted under 35 U.S.C. 154(b) by 905 days.

(21) Appl. No.: 13/024,977

(22) Filed: Feb. 10, 2011

(65) Prior Publication Data

US 2011/0230346 A1    Sep. 22, 2011

Related U.S. Application Data

(60) Provisional application No. 61/303,071, filed on Feb. 10, 2010.

(30) Foreign Application Priority Data

Feb. 10, 2010 (EP) ..................................... 10153201

(51) Int. Cl.

| C07D 209/54 | (2006.01) |
|---|---|
| C07D 207/40 | (2006.01) |
| C07D 307/60 | (2006.01) |
| C07D 307/94 | (2006.01) |
| A61K 31/407 | (2006.01) |
| A61K 31/343 | (2006.01) |
| A61K 31/341 | (2006.01) |
| A61K 31/40 | (2006.01) |
| A01N 43/12 | (2006.01) |
| A01N 43/36 | (2006.01) |
| A01N 43/90 | (2006.01) |
| A01N 43/08 | (2006.01) |
| A01N 43/38 | (2006.01) |
| C07D 207/36 | (2006.01) |

(52) U.S. Cl.
CPC .............. *C07D 207/36* (2013.01); *A01N 43/90* (2013.01); *A01N 43/08* (2013.01); *A01N 43/38* (2013.01); *A01N 43/36* (2013.01); *C07D 307/60* (2013.01); *A01N 43/12* (2013.01)
USPC ........... 504/283; 504/299; 514/462; 514/473; 514/409; 514/425; 548/544; 548/408; 549/477; 549/330

(58) Field of Classification Search
None
See application file for complete search history.

(56) References Cited

U.S. PATENT DOCUMENTS

| 2,842,476 A | 7/1958 | Schreiber |
|---|---|---|
| 4,245,432 A | 1/1981 | Dannelly |
| 4,272,417 A | 6/1981 | Barke et al. |
| 4,623,727 A | 11/1986 | Hübele |
| 4,639,266 A | 1/1987 | Heubach et al. |
| 4,808,430 A | 2/1989 | Kouno |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |

(Continued)

FOREIGN PATENT DOCUMENTS

| AU | 2003206693 A1 | 7/2003 |
|---|---|---|
| CA | 1 162 071 A1 | 2/1984 |

(Continued)

OTHER PUBLICATIONS

Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, SCI, Great Britain (1997).

(Continued)

*Primary Examiner* — Michael Barker
(74) *Attorney, Agent, or Firm* — Sterne, Kessler, Goldstein & Fox P.L.L.C.

(57) ABSTRACT

The invention relates to novel compounds of the formula (I)

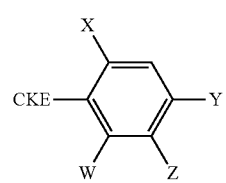

in which W, X, Y, Z, and CKE have the meanings given above, to a plurality of processes and intermediates for their preparation and to their use as pesticides and/or herbicides and/or fungicides.

Moreover, the invention relates to selectively herbicidal compositions comprising, firstly, the biphenyl-substituted cyclic ketoenols and, secondly, a crop plant compatibility-improving compound.

The present invention furthermore relates to the boosting of the action of crop protection compositions comprising in particular biphenyl-substituted cyclic ketoenols through the addition of ammonium or phosphium salts and optionally penetrants, to the corresponding compositions, to processes for their preparation and to their use in crop protection as insecticides and/or nematicides and/or acaricides and/or fungicides and/or for preventing unwanted plant growth.

18 Claims, No Drawings

(56) References Cited

U.S. PATENT DOCUMENTS

| | | |
|---|---|---|
| 4,944,790 A | 7/1990 | Moser et al. |
| 4,985,063 A | 1/1991 | Fischer et al. |
| 5,013,659 A | 5/1991 | Bedbrook et al. |
| 5,045,560 A | 9/1991 | Fischer et al. |
| 5,094,681 A | 3/1992 | Krämer et al. |
| 5,116,836 A | 5/1992 | Fischer et al. |
| 5,215,570 A | 6/1993 | Burckhardt et al. |
| 5,225,434 A | 7/1993 | Bertram et al. |
| 5,258,527 A | 11/1993 | Krauskopf et al. |
| 5,262,383 A | 11/1993 | Fischer et al. |
| 5,314,863 A | 5/1994 | Löher et al. |
| 5,380,852 A | 1/1995 | Schütze et al. |
| 5,401,700 A | 3/1995 | Sohn et al. |
| 5,462,912 A | 10/1995 | Hioki et al. |
| 5,462,913 A | 10/1995 | Fischer et al. |
| 5,500,367 A | 3/1996 | Hain et al. |
| 5,504,057 A | 4/1996 | Fischer et al. |
| 5,508,436 A | 4/1996 | Fischer et al. |
| 5,516,750 A | 5/1996 | Willms et al. |
| 5,538,937 A | 7/1996 | Hasebe et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,683,965 A | 11/1997 | Bachmann et al. |
| 5,689,046 A | 11/1997 | Schröder et al. |
| 5,700,758 A | 12/1997 | Rösch et al. |
| 5,703,132 A | 12/1997 | Sagenmüller et al. |
| 5,705,476 A | 1/1998 | Hoffarth |
| 5,739,079 A | 4/1998 | Holdgrün et al. |
| 5,792,755 A | 8/1998 | Sagenmüller et al. |
| 5,811,374 A | 9/1998 | Bertram et al. |
| 5,830,825 A | 11/1998 | Fischer et al. |
| 5,830,826 A | 11/1998 | Fischer et al. |
| 5,876,739 A | 3/1999 | Turnblad et al. |
| 5,972,839 A | 10/1999 | Ziemer et al. |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,589,976 B1 | 7/2003 | Fischer et al. |
| 6,602,823 B1 | 8/2003 | Röchling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 7,432,225 B2 | 10/2008 | Fischer et al. |
| 7,491,738 B2 | 2/2009 | Goto et al. |
| 7,612,100 B2 | 11/2009 | Koyanagi et al. |
| 7,638,547 B2 | 12/2009 | Himmler et al. |
| 7,718,186 B2 | 5/2010 | Fischer et al. |
| 7,727,933 B2 | 6/2010 | Fischer et al. |
| 7,754,654 B2 | 7/2010 | Fischer et al. |
| 7,776,791 B2 | 8/2010 | Fischer et al. |
| 7,838,463 B2 | 11/2010 | Bickers et al. |
| 7,872,036 B2 | 1/2011 | Toriyabe et al. |
| 7,888,285 B2 | 2/2011 | Fischer et al. |
| 7,897,543 B2 | 3/2011 | Bretschneider et al. |
| 7,915,282 B2 | 3/2011 | Ruther et al. |
| 7,947,704 B2 | 5/2011 | Bretschneider et al. |
| 8,013,172 B2 | 9/2011 | Fischer et al. |
| 8,039,014 B2 | 10/2011 | Fischer et al. |
| 8,084,452 B2 | 12/2011 | Jeschke et al. |
| 8,106,211 B2 | 1/2012 | Jeschke et al. |
| 8,106,212 B2 | 1/2012 | Jeschke et al. |
| 8,119,566 B2 | 2/2012 | Fischer et al. |
| 8,138,118 B2 | 3/2012 | Bickers et al. |
| 8,138,119 B2 | 3/2012 | Fischer et al. |
| 2003/0171219 A1 | 9/2003 | Lieb et al. |
| 2003/0176428 A1 | 9/2003 | Schneidersmann et al. |
| 2003/0216260 A1 | 11/2003 | Ruther et al. |
| 2003/0224939 A1 | 12/2003 | Miles |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0049145 A1 | 3/2005 | Bickers et al. |
| 2005/0054535 A1 | 3/2005 | Fischer et al. |
| 2005/0096386 A1 | 5/2005 | Cottrell et al. |
| 2005/0256000 A1 | 11/2005 | Schaper et al. |
| 2006/0160847 A1 | 7/2006 | Fischer et al. |
| 2006/0166829 A1 | 7/2006 | Fischer et al. |
| 2006/0281780 A1 | 12/2006 | Goto et al. |
| 2007/0015664 A1 | 1/2007 | Fischer et al. |
| 2007/0032539 A1 | 2/2007 | Himmler |
| 2007/0129252 A1 | 6/2007 | Fischer et al. |
| 2007/0129407 A1 | 6/2007 | Koyanagi et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0081807 A1 | 4/2008 | Lieb et al. |
| 2008/0167188 A1 | 7/2008 | Fischer et al. |
| 2008/0188371 A1 | 8/2008 | Fischer et al. |
| 2008/0220973 A1 | 9/2008 | Fischer et al. |
| 2008/0269052 A1 | 10/2008 | Rosinger et al. |
| 2008/0269059 A1 | 10/2008 | Ziemer et al. |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0076282 A1 | 3/2009 | Toriyabe et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0247551 A1 | 10/2009 | Jeschke et al. |
| 2009/0253749 A1 | 10/2009 | Jeschke et al. |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |
| 2010/0168226 A1 | 7/2010 | Fischer et al. |
| 2010/0240705 A1 | 9/2010 | Jeschke et al. |
| 2010/0261608 A1 | 10/2010 | Fischer et al. |
| 2010/0279873 A1 | 11/2010 | Fischer et al. |
| 2010/0298145 A1 | 11/2010 | Bretschneider et al. |
| 2010/0311593 A1 | 12/2010 | Fischer et al. |
| 2011/0086762 A1 | 4/2011 | Fischer et al. |
| 2011/0130284 A1 | 6/2011 | Fischer et al. |
| 2011/0263424 A1 | 10/2011 | Bretschneider et al. |
| 2011/0306499 A1 | 12/2011 | Bretschneider et al. |
| 2012/0015807 A1 | 1/2012 | Fischer et al. |

FOREIGN PATENT DOCUMENTS

| | | |
|---|---|---|
| CA | 2 671 179 A1 | 6/2008 |
| CA | 2 695 032 A1 | 2/2009 |
| CA | 2 700 292 A1 | 4/2009 |
| CA | 2 718 735 A1 | 9/2009 |
| DE | 10 2005 059 892 A1 | 6/2007 |
| DE | 102006057037 A1 * | 6/2008 |
| EP | 0 142 924 A2 | 5/1985 |
| EP | 0 193 259 A1 | 9/1986 |
| EP | 0 221 044 A1 | 5/1987 |
| EP | 0 242 236 A1 | 10/1987 |
| EP | 0 242 246 A1 | 10/1987 |
| EP | 0 257 993 A2 | 3/1988 |
| EP | 0 262 399 A2 | 4/1988 |
| EP | 0 346 620 A1 | 12/1989 |
| EP | 0 453 086 A2 | 10/1991 |
| EP | 0 539 588 A1 | 5/1993 |
| GB | 2 266 888 A | 11/1993 |

(56) References Cited

FOREIGN PATENT DOCUMENTS

| | | |
|---|---|---|
| JP | 60-87254 A | 5/1985 |
| JP | 2000-53670 A | 2/2000 |
| JP | 2002-205984 A | 7/2002 |
| WO | WO 84/02919 A1 | 8/1984 |
| WO | WO 89/10396 A1 | 11/1989 |
| WO | WO 91/13972 A1 | 9/1991 |
| WO | WO 91/19806 A1 | 12/1991 |
| WO | WO 92/00377 A1 | 1/1992 |
| WO | WO 92/11376 A1 | 7/1992 |
| WO | WO 92/14827 A1 | 9/1992 |
| WO | WO 92/16108 A1 | 10/1992 |
| WO | WO 95/17817 A1 | 7/1995 |
| WO | WO 96/33270 A1 | 10/1996 |
| WO | WO 98/13361 A1 | 4/1998 |
| WO | WO 98/35553 A1 | 8/1998 |
| WO | WO 98/38856 A1 | 9/1998 |
| WO | WO 02/28186 A2 | 4/2002 |
| WO | WO 02/34048 A1 | 5/2002 |
| WO | WO 02/080675 A1 | 10/2002 |
| WO | WO 03/062244 A1 | 7/2003 |
| WO | WO 2005/035486 A1 | 4/2005 |
| WO | WO 2006/056433 A2 | 6/2006 |
| WO | WO 2006/100288 A2 | 9/2006 |
| WO | WO 2007/023719 A1 | 3/2007 |
| WO | WO 2007/023764 A1 | 3/2007 |
| WO | WO 2007/024782 A2 | 3/2007 |
| WO | WO 2007/027777 A2 | 3/2007 |
| WO | WO 2007/043677 A1 | 4/2007 |
| WO | WO 2007/057407 A2 | 5/2007 |
| WO | WO 2007/095229 A2 | 8/2007 |
| WO | WO 2007/149134 A1 | 12/2007 |
| WO | WO 2008/104503 A1 | 9/2008 |
| WO | WO 2008/138551 A2 | 11/2008 |
| WO | WO 2009/049851 A1 | 4/2009 |
| WO | WO 2010/000066 A1 | 1/2010 |
| WO | WO 2010/052161 A2 | 5/2010 |
| WO | WO 2010/063670 A1 | 6/2010 |
| WO | WO 2010/066780 A1 | 6/2010 |
| WO | WO 2010/135914 A1 | 12/2010 |
| ZA | 985601 A | 1/1999 |

OTHER PUBLICATIONS

Bhattacharya, B., "Isoquinoline Derivatives: Part XVIII—Formation of I-Alkyl(or alkaryl or aryl)-3-methyl-7-chloro-(or 5-chloro)-isoquinolines," *Indian J Chem.* 6:341-345, Council of Scientific & Industrial Research, India (1968).

Braun, H-P., et al., "The general mitochondrial processing peptidase from potato is an integral part of cytochrome *c* reductase of the respiratory chain," *The EMBO Journal*, 11(9): 3219-3227, Oxford University Press, England (1992).

Campbell, A.C., et al., "Synthesis of (*E* )- and (*Z* )-Pulvinones," *J. Chem. Soc. Perkin Trans*. 1:1567, Chemical Society, England (1985).

Christou, P., "Transformation technology, " *Trends in Plant Science* 1(12):423-431, Elsevier Science Ltd., England (1996).

Compagnon, P.L. and Miocque, M., "Addition des Réactifs Nucléophiles sur la Triple Liaison Nitrile," *Ann. Chim.* 5:11-27, SocietàChimica Italiana, Italy (1970).

Draber W., "Chemie der Pflanzenschutz-und Schadlingsbekampfungsmittel [Chemistry of Plant Protection and Pest Control Agents]," R. Wegler (eds.) 2:400-412, Springer-Verlag, Berlin (1970).

English language translation of Draber W., "Chemic der Pflanzenschutz-und Schadlingsbekampfungsmittel [Chemistry of Plant Protection and Pest Control Agents]," R. Wegler (eds.) 2:400-412, Springer-Verlag, Berlin (1970).

Edward, J.T., and Jitrangsri, C., "Stereochemistry of the Bucherer-Bergs and Strecker Reactions of 4-*tert*-Butylcyclohexanone," *Can. J. Chem.* 53: 3339-3350, National Research Council, Canada (1975).

Harrision, H. R., et al., "Use of molecular sieves in the methyl esterification of carboxylic acids," *Chemistry and Industry* 1568, Society of Chemical Industry, England (1968).

Ito, M., et al., "Synthesis and Insecticidal Activity of Novel *N*-Oxydihydropyrrole Detivatives with a Substituted Spirocycohexyl Group," *Biosci. Biotechnol. Biochem.* 67(6):1230-1238, Japan Society for Bioscience, Biotechnology, and Agrochemistry, Japan (2003).

Klingman, G.C., eds., "Surface Active Agents," in *Weed Control as a Science*, pp. 81-96, John Wiley and Sons, Inc., New York, United States (1961).

Munday, L., "861. Amino-acids of the Cyclohexane Series. Part I," *J. Chem. Soc.* 4372-4379, Chemical Society (Great Britain), England (1961).

Perry, J.H., eds., *Chemical Engineers' Handbook, Fourth Edition*, pp. 4, McGraw Hill Book Company, Inc., United States (1963).

Schmierer, S., and Mildenberger, H., "Cyclisierung von *N*-Acylalanin- und *N*- Acylglycinestern," *Liebigs Ann. Chem.*:1095-1098, VCH Verlagsgesllschaft mbH, Weinheim, Germany (1985).

English-language, machine generated translation of Schmierer, S., and Mildenberger, H., "Cyclisierung von *N*-Acylalanin- und *N*-Acylglycinestern," *Liebigs Ann. Chem.*:1095-1098, VCH Verlagsgesellschaft mbH, Weinheim, Germany (1985).

Sonnewald, U., et al., "Transgenic tobacco plants expressing yeast-derived invertase in either the cytosol, vacuole or apoplast: a powerful tool for studying sucrose metabolism and sink/source interactions," *The Plant Journal* 1 (1):95-106, Blackwell Scientific Publishers, England (1991).

Sonntag, N.O.V., "The Reactions of Aliphatic Acid Chlorides," *Chemical Reviews* 52:237-416, American Chemical Society, United States (1953).

Suzuki, S., et al., "Studies on Antiviral Agents IV. Biological Activity of Tenuazonic Acid Derivatives," *Chem. Pharm. Bull.* 13(8):1120-1122, Pharmaceutical Society of Japan, Japan (1967).

Wolter, F.P., et al., "rbcS genes in *Solanum tuberosum*: Conservation of transit peptide and exon shuffling during evolution," *Proc. Natl. Acad. Sci. USA* 85:846-850, National Academy of Science, United States (1988).

"D.7.1.5. Reaktionen von Carbonsäuren und Carbonsäurederivaten mit Basen," 505, Organikum, Berlin, Germany (1977).

"The Use of Herbicides in Potato," in *Weed Control Handbook*, pp. 101-103, British Crop Protection Council, Blackwell Scientific, England (1968).

English language Abstract of WIPO Patent Publication No. WO 2007/023764 A1, published Mar. 1, 2007, European Patent Office, espacenet database—Worldwide (2007).

English language Abstract of EP Patent Publication No. EP 0 346 620 A1, published Dec. 20, 1989, European Patent Office, espacenet database—Worldwide (1989).

English language Abstract of JP Patent Publication No. JP 60-87254 A, published May 16, 1985, European Patent Office, espacenet database—Worldwide (1985).

English language Abstract of WIPO Patent Publication No. WO 2007/023719 A1, published Mar. 1, 2007, European Patent Office, espacenet database—Worldwide (2007).

Unverified English language Translation of German Patent Application No. WO DE 10 2005 059 892 A1, published Jun. 28, 2007.

Unverified English language Translation of WIPO Patent Publication No. WO 2008/138551 A2, published Nov. 20, 2008.

English language Abstract of Japanese Patent Publication No. JP 2000-53670 A, published Feb. 22, 2000, Japanese Patent Office, Patent & Utility Model Gazette DB, Patent Abstracts of Japan (2000).

English language Abstract of Japanese Patent Publication No. JP 2002-205984 A, published Jul. 23, 2002, Japanese Patent Office, Patent & Utility Model Gazette DB, Patent Abstracts of Japan (2000).

European Search Report for European Application No. 10 15 3201, European Patent Office, The Hague, Netherlands, mailed on Jul. 7, 2010.

* cited by examiner

BIPHENYL-SUBSTITUTED CYCLIC KETOENOLS

The present invention relates to novel biphenyl-substituted cyclic ketoenols, to a plurality of processes for their preparation and to their use as pesticides and/or herbicides and/or fungicides. The invention also relates to selective herbicidal compositions comprising, firstly, biphenyl-substituted cyclic ketoenols and, secondly, a crop plant compatibility-improving compound.

The present invention furthermore relates to boosting the action of crop protection compositions comprising in particular biphenyl-substituted cyclic ketoenols by addition of ammonium or phosphonium salts and optionally penetrants, to the corresponding compositions, to processes for their preparation and to their use in crop protection as insecticides and/or acaricides and/or nematicides and/or fungicides and/or for preventing unwanted vegetation.

For 3-acylpyrrolidin-2,4-diones pharmaceutical properties have been previously described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). Biological activity of these compounds has not been described.

EP-A-0 262 399 and GB-A-2 266 888 disclose similarly structured compounds (3-arylpyrrolidine-2,4-diones) for which, however, no herbicidal, insecticidal or acaricidal action has been disclosed. Known compounds with herbicidal, insecticidal or acaricidal action are unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893, EP-A-442 077 and WO 10/066,780).

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140,881, WO 08/067,873, WO 08/067,910, WO 08/067,911, WO 08/138,551, WO 09/015,801, WO 09/039,975, WO 09/049,851, WO 09/115,262, WO 10/052,161, WO 10/102,758, WO 10/063,378, WO 10/063,670). Moreover, ketal-substituted 1-H-arylpyrrolidine-2,4-diones are known from WO 99/16748 and (spiro)ketal-substituted N-alkoxyalkoxy-substituted arylpyrrolidinediones are known from JP-A-14 205 984 and Ito M. et al., Bioscience, Biotechnology and Biochemistry 67, 1230-1238, (2003). The addition of safeners to ketoenols is also known in principle from WO 03/013249. Moreover, herbicidal compositions comprising ketoenols are known from WO 06/024411.

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuranone-(2)) is likewise described in DE-A-4 014 420. Similarly structured compounds without any insecticidal and/or acaricidal activity stated are known from the publication Campbell et al., J. Chem. Soc., Perkin Trans. 1, 1985, (8) 1567-76. Furthermore known are 3-aryl-$\Delta^3$-dihydrofuranone derivatives having herbicidal, acaricidal and insecticidal properties, from: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048, 545, WO 07/073,856, WO 07/096,058, WO 07/121,868, WO 07/140,881, WO 08/067,911, WO 08/083,950, WO 09/015, 801, WO 09/039,975, WO 10/133,337 and WO 10/135,914.

Also known are biphenyl-substituted 1H-pyrrolidinedione derivatives having fungicidal action (WO 03/059065).

However, in particular at low application rates and concentrations, the activity and activity spectrum of these compounds is not always fully satisfactory. Furthermore, the compatibility of these compounds with crop plants is not always sufficient. Moreover, the toxicological properties and/or environmental properties of these compounds are not always fully satisfactory.

This invention now provides novel compounds of the formula (I)

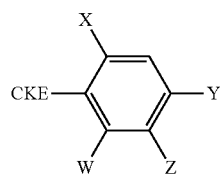

in which
W represents halogen or alkyl,
X represents halogen, alkyl or haloalkyl,
Z represents optionally mono- or polysubstituted phenyl,
Y represents hydrogen, halogen, alkyl, alkoxy, haloalkyl or haloalkoxy,
with the proviso that at least one of the radicals W or X represents halogen or ethyl,
CKE represents one of the groups

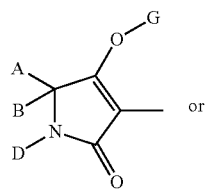

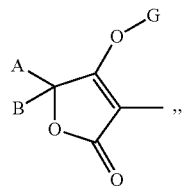

in which
A represents hydrogen, or represents in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, or represents in each case optionally substituted arylalkyl, aryl, hetarylalkyl or hetaryl or A and D together with the atoms to which they are attached represent a saturated or unsaturated cycle which is unsubstituted or substituted in the A,D moiety and optionally contains at least one heteroatom, G represents hydrogen (a) or represents one of the groups

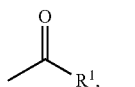
(b)

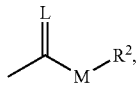
(c)

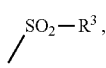
(d)

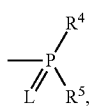
(e)

E or (f)

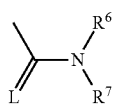
(g)

in which

E represents a metal ion or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cylcoalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, or represent optionally substituted phenyl, optionally substituted benzyl or together with the nitrogen atom to which they are attached represent a ring which is optionally interrupted by oxygen or sulphur.

Depending inter alia on the nature of the substituents, the compounds of the formula (I) may be present as geometrical and/or optical isomers or isomer mixtures of varying composition which, if appropriate, may be separated in a customary manner. The present invention provides the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having varying proportions of isomeric compounds.

Including the meanings (1) and (2) of the group CKE, the following principal structures (I-1) and (I-2) result:

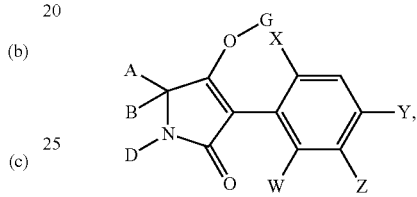
(I-1)

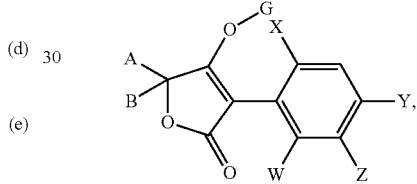
(I-2)

in which

A, B, D, G, W, X, Y and Z have the meaning given above.

Including the different meanings (a), (b), (c), (d), (e), (f) and (g) of group G, the following principal structures (I-1-a) to (I-1-g) result if CKE represents the group (1)

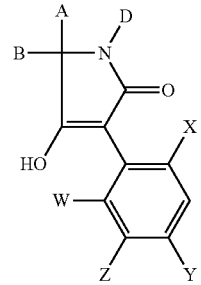
(I-1-a)

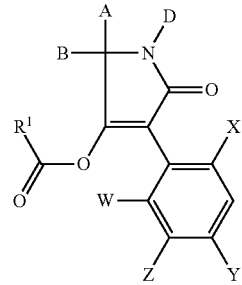
(I-1-b)

-continued
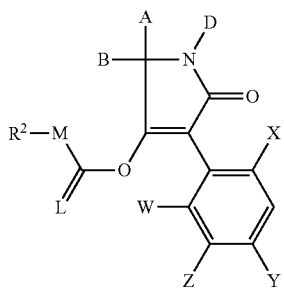
(I-1-c)
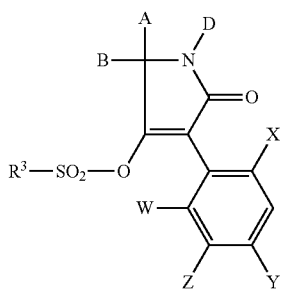
(I-1-d)
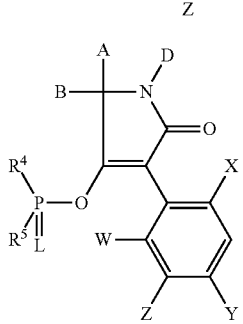
(I-1-e)
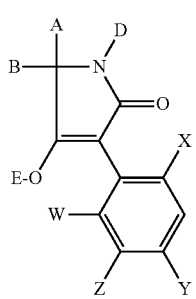
(I-1-f)
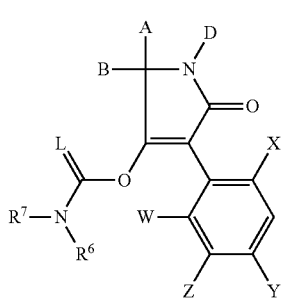
(I-1-g)
in which
A, B, D, E, L, M, W, X, Y, Z, $R^1$, $R^2$, $R^3$, $R^4$, $R^5$, $R^6$ and $R^7$ have the meanings given above.
Including the different meanings (a), (b), (c), (d), (e), (f) and (g) of group G, the following principal structures (I-2-a) to (I-2-g) result if CKE represents the group (2)
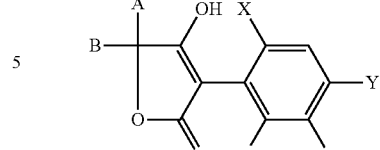
(I-2-a)
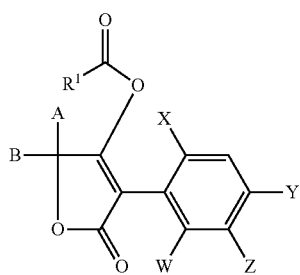
(I-2-b)
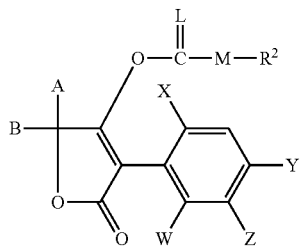
(1-2-c)
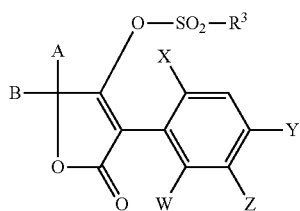
(1-2-d)
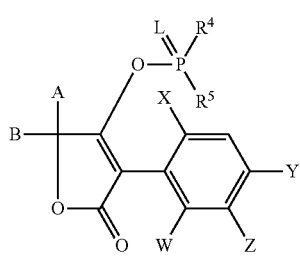
(1-2-e)
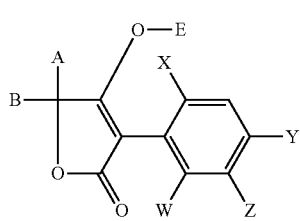
(1-2-f)

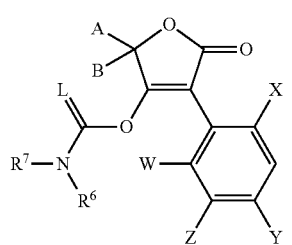
(I-2-g)

in which

A, B, E, L, M, W, X, Y, Z, $R^1$, $R^2$, $R^3$, $R^4$, $R^5$, $R^6$ and $R^7$ have the meanings given above.

Furthermore, it has been found that the novel compounds of the formula (I) are obtained by one of the processes described below:

(A) Substituted 3-biphenylpyrrolidine-2,4-diones or enols thereof of the formula (I-1-a)

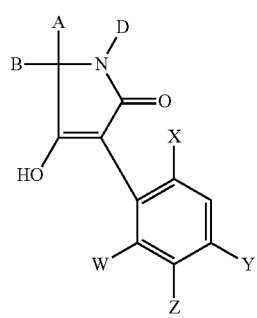
(I-1-a)

in which

A, B, D, W, X, Y and Z have the meanings given above are obtained when

N-Acylamino acid esters of the formula (II)

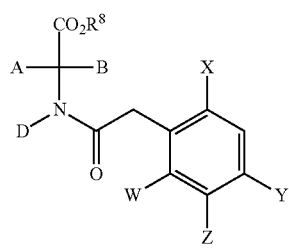
(II)

in which

A, B, D, W, X, Y and Z have the meanings given above and $R^8$ represents alkyl (preferably $C_1$-$C_6$-alkyl), are condensed intramolecularly in the presence of a diluent and in the presence of a base.

(B) Moreover, it has been found that substituted 3-biphenyl-4-hydroxy-$\Delta^3$-dihydrofuranone derivatives of the formula (I-2-a)

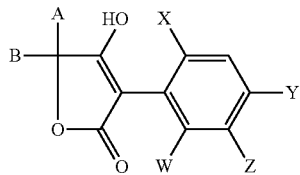
(I-2-a)

in which

A, B, W, X, Y and Z have the meanings given above and are obtained when carboxylic esters of the formula (III)

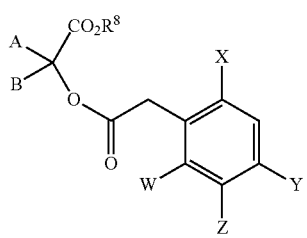
(III)

in which

A, B, W, X, Y, Z and $R^8$ have the meanings given above are condensed intramolecularly in the presence of a diluent and in the presence of a base.

(C) Furthermore, it has been found that compounds of the formulae (I-1-a) to (I-2-g) shown above in which A, B, D, G, W, X, Y and Z have the meaning given above are obtained when compounds of the formulae (I-1'-a) to (I-2'-g),

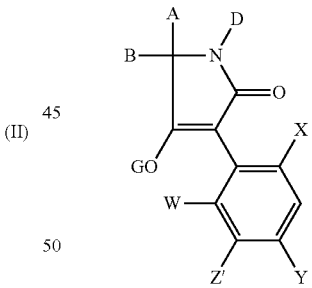
(I-1'-a) to (I-1'-g)

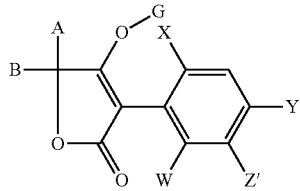
(I-2'-a) to (I-2'-g)

in which

A, B, D, G, W, X and Y have the meaning given above and

Z' represents chlorine, bromine, iodine, preferably bromine, are reacted with boronic acids or boronic acid derivatives of the formula (IV)

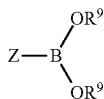  (IV)

in which

R$^9$ represents hydrogen, C$_1$-C$_6$-alkyl or C$_2$-C$_6$-alkanediyl and

Z has the meaning given above, in the presence of a solvent, a base and a catalyst, suitable catalysts being in particular palladium salts or palladium complexes.

Moreover, it has been found (D) that the compounds of the formulae (I-1-b) to (I-2-b) shown above in which A, B, D, R$^1$, W, X, Y and Z have the meanings given above are obtained when compounds of the formulae (I-1-a) to (I-2-a) shown above in which A, B, D, W, X, Y and Z have the meanings given above are in each case reacted (α) with acid halides of the formula (V)

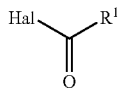  (V)

in which

R$^1$ has the meaning given above and

Hal represents halogen (in particular chlorine or bromine) or (β) with carboxylic anhydrides of the formula (VI)

  (VI)

R$^1$—CO—O—CO—R$^1$ in which

R$^1$ has the meaning given above, if appropriate in the presence of a diluent and if appropriate in the presence of an acid binder;

(E) that the compounds of the formulae (I-1-c) to (I-2-c) shown above in which A, B, D, R$^2$, M, W, X, Y and Z have the meanings given above and L represents oxygen are obtained when compounds of the formulae (I-1-a) to (I-2-a) shown above in which A, B, D, W, X, Y and Z have the meanings given above are in each case reacted with chloraformic esters or chloraformic thioesters of the formula (VII)

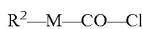  (VII)

R$^2$—M—CO—Cl in which

R$^2$ and M have the meanings given above, if appropriate in the presence of a diluent and if appropriate in the presence of an acid binder;

(F) that compounds of the formulae (I-1-c) to (I-2-c) shown above in which A, B, D, R$^2$, M, W, X, Y and Z have the meanings given above and L represents sulphur are obtained when compounds of the formulae (I-1-a) to (I-2-a) shown above in which A, B, D, W, X, Y and Z have the meanings given above are in each case reacted with chloromonothioformic esters or chlorodithioformic esters of the formula (VIII)

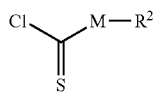  (VIII)

in which

M and R$^2$ have the meanings given above, if appropriate in the presence of a diluent and if appropriate in the presence of an acid binder, (G) that compounds of the formulae (I-1-d) to (I-2-d) shown above in which A, B, D, R$^3$, W, X, Y and Z have the meanings given above are obtained when compounds of the formulae (I-1-a) to (I-2-a) shown above in which A, B, D, W, X, Y and Z have the meanings given above are in each case reacted with sulphonyl chlorides of the formula (IX)

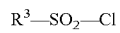  (IX)

R$^3$—SO$_2$—Cl in which

R$^3$ has the meaning given above, if appropriate in the presence of a diluent and if appropriate in the presence of an acid binder, (H) that compounds of the formulae (I-1-e) to (I-2-e) shown above in which A, B, D, L, R$^4$, R$^5$, W, X, Y and Z have the meanings given above are obtained when compounds of the formulae (I-1-a) to (I-2-a) shown above in which A, B, D, W, X, Y and Z have the meanings given above are in each case reacted with phosphorus compounds of the formula (X)

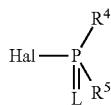  (X)

in which

L, R$^4$ and R$^5$ have the meanings given above and

Hal represents halogen (in particular chlorine or bromine), if appropriate in the presence of a diluent and if appropriate in the presence of an acid binder, (I) that compounds of the formulae (I-1-f) to (I-2-f) shown above in which A, B, D, E, W, X, Y and Z have the meanings given above are obtained when compounds of the formulae (I-1-a) to (I-2-a) shown above in which A, B, D, W, X, Y and Z have the meanings given above are in each case reacted with metal compounds or amines of the formulae (XI) and (XII), respectively,

  (XI)

Me(OR$^{10}$)$_t$

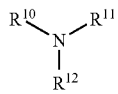  (XII)

in which

Me is a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (J) that compounds of the formulae (I-1-g) to (I-2-g) shown above in which A, B, D, L, $R^6$, $R^7$, W, X, Y and Z have the meanings given above are obtained when compounds of the formulae (I-1-a) to (I-2-a) shown above in which A, B, D, W, X, Y and Z have the meanings given above are in each case reacted (α) with isocyanates or isothiocyanates of the formula (XIII)

$$R^6\!-\!N\!=\!C\!=\!L \qquad (XIII)$$

in which $R^6$ and L have the meanings given above, if appropriate in the presence of a diluent and if appropriate in the presence of a catalyst, or (β) with carbamoyl chlorides or thiocarbamoyl chlorides of the formula (XIV)

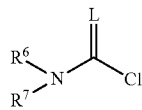
(XIV)

in which

L, $R^6$ and $R^7$ have the meanings given above, if appropriate in the presence of a diluent and if appropriate in the presence of an acid binder.

Furthermore, it has been found that the novel compounds of the formula (I) are very effective as pesticides, preferably as insecticides and/or acaricides and/or nematicides, and/or fungicides and/or herbicides, that they are additionally frequently tolerated very well by plants, in particular by crop plants, and/or that they have favourable toxicological and/or environmental properties.

Surprisingly, it has now also been found that certain biphenyl-substituted spirocyclic ketoenols, when used together with crop plant compatibility-improving compounds (safeners/antidotes) described below, very efficiently prevent damage to the crop plants and can be used in a particularly advantageous manner as broad-spectrum combination preparations for the selective control of unwanted plants in crops of useful plants, such as, for example, in cereals, but also in maize, oilseed rape, soya beans and rice.

The invention also provides selective herbicidal compositions comprising an effective amount of an active compound combination comprising, as components, (a') at least one compound of the formula (I), in which CKE, W, X, Y and Z have the meaning given above and (b') at least one crop plant compatibility-improving compound (safener).

The safeners are preferably selected from the group consisting of:

Si) Compounds of the formula (S1)

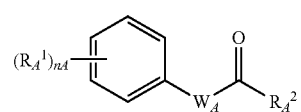
(S1)

where the symbols and indices have the following meanings:

$n_A$ is a natural number from 0 to 5, preferably from 0 to 3;

$R_A^1$ is halogen, ($C_1$-$C_4$)-alkyl, ($C_1$-$C_4$)-alkoxy, nitro or ($C_1$-$C_4$)-haloalkyl;

$W_A$ is an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of ($W_A^1$) to ($W_A^4$),

($W_A^1$)

($W_A^2$)

($W_A^3$)

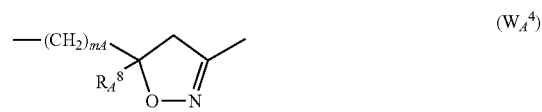
($W_A^4$)

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of ($C_1$-$C_4$)-alkyl, ($C_1$-$C_4$)-alkoxy and optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical having preferably a total of 1 to 18 carbon atoms;

$R_A4$ is hydrogen, ($C_1$-$C_6$)-alkyl, ($C_1$-$C_6$)-alkoxy or substituted or unsubstituted phenyl;

$R_A^5$ is H, ($C_1$-$C_8$)-alkyl, ($C_1$-$C_8$)-haloalkyl, ($C_1$-$C_4$)-alkoxy-($C_1$-$C_8$)-alkyl, cyano or $COOR_A^9$ where $R_A^9$ is hydrogen, ($C_1$-$C_8$)-alkyl, ($C_1$-$C_4$)-haloalkyl, ($C_1$-$C_4$)-alkoxy-($C_1$-$C_4$)-alkyl, ($C_1$-$C_6$)-hydroxyalkyl, ($C_3$-$C_{12}$)-cycloalkyl or tri-($C_1$-$C_4$)-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:
a) compounds of the type of the dichlorophenylpyrazoline-3-carboxylic acid ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;
b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;
c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;
d) compounds of the type of the triazolecarboxylic acids ($S1^d$), preferably compounds such as fenchlorazole (ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;
e) compounds of the type of the 5-benzyl- or 5-phenyl-2-isoxazoline-3-carboxylic acid or the 5,5-diphenyl-2-isoxazoline-3-carboxylic acid ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.

S2) Quinoline derivatives of the formula (S2)

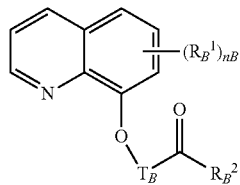

(S2)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl, preferably a radical of the formula $OR_B^3$, $NHR_B^4$ or $N(CH_3)_2$, in particular of the formula $OR_B^3$;
$R_B^3$ is hydrogen or an unsubstituted or substituted aliphatic hydrocarbon radical having preferably a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a $(C_1-$ or $C_2)$-alkanediyl chain which is unsubstituted or substituted by one or two $(C_1-C_4)$-alkyl radicals or by $[(C_1-C_3)$-alkoxy]carbonyl;

preferably:
a) compounds of the type of the 8-quinolinoxyacetic acid ($S2^a$), preferably 1-methylhexyl (5-chloro-8-quinolinoxy)acetate ("cloquintocet-mexyl") (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;
b) compounds of the type of the (5-chloro-8-quinolinoxy) malonic acid ($S2^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

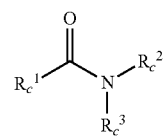

(S3)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the type of the dichloroacetamides which are frequently used as pre-emergence safeners (soil-acting safeners), such as, for example, "dichloromide" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl] dichloroacetamide) from PPG Industries (S3-5), "DKA-24" (N-allyl-N-[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9) (3-dichloroacetyl-2,5,5-trimethyl-1,3-diazabicyclo[4.3.0] nonane) from BASF, "furilazole" or "MON 13900" ((RS)-3-dichloroacetyl-5-(2-furyl)-2,2-dimethyloxazolidine) (S3-10) and also its (R)-isomer (S3-11).

S4) N-Acylsulphonamides of the formula (S4) and their salts

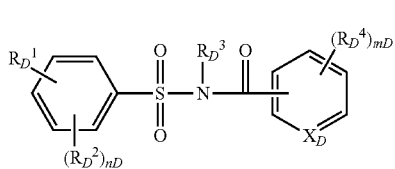

(S4)

where the symbols and indices have the following meanings:

$X_D$ is CH or N;
$R_D^1$ is CO—$NR_D^5 R_D'$ or NHCO—$R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;
$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$n_D$ is 0, 1 or 2;
$m_D$ is 1 or 2;
$v_D$ is 0, 1, 2 or 3;

from among these, preference is given to compounds of the type of the N-acylsulphonamides, for example of the formula (S4$^a$) below, which are known, for example, from WO-A-97/45016

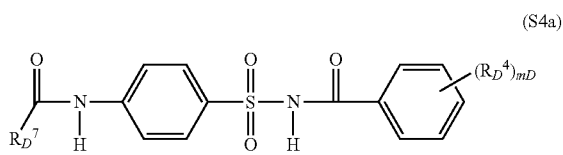

(S4a)

in which
$R_D^7$ is $(C_1-C_6)$-alkyl, $(C_3-C_6)$-cycloalkyl, where the 2 last-mentioned radicals are substituted by $V_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_4)$-alkyl, $(C_1-C_4)$-alkoxy, $CF_3$;
$m_D$ is 1 or 2;
$v_D$ is 0, 1, 2 or 3;

and also
acylsulphamoylbenzamides, for example of the formula (S4$^b$) below, which are known, for example, from WO-A-99/16744,

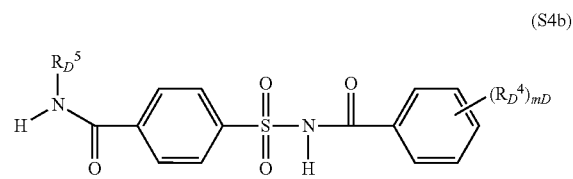

(S4b)

for example those in which
$R_D^5$=cyclopropyl and $(R_D^4)$=2-OMe ("cyprosulphamide", S4-1),
$R_D^5$=cyclopropyl and $(R_D^4)$=5-$C_{1-2}$-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)

and also
compounds of the type of the N-acylsulphamoylphenylureas of the formula (S4$^c$), which are known, for example, from EP-A-365484,

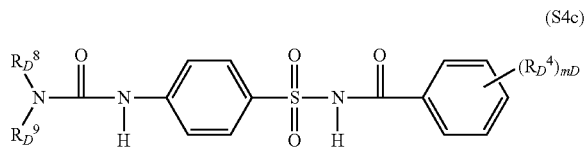

in which $R_D^8$ and $R_D^9$ independently of one another are hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$, $m_D$ is 1 or 2;

for example

1-[4-(N-2-methoxybenzoylsulphamoyl)phenyl]-3-methylurea,

1-[4-(N-2-methoxybenzoylsulphamoyl)phenyl]-3,3-dimethylurea,

1-[4-(N-4,5-dimethylbenzoylsulphamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

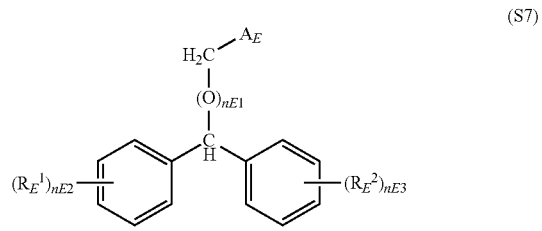

where the symbols and indices have the following meanings:

$R_E^1$, $R_E^2$ independently of one another are halogen, $(C_1-C_4)$-alkyl, $(C_1-C_4$-alkoxy, $(C_1-C_4)$-haloalkyl, $(C_1-C_4)$-alkylamino, di-$(C_1-C_4$-alkylamino, nitro;

$A_E$ is $COOR_E^3$ or $COSR_E^4$;

$R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1;

$n_E^2$, $n_E^3$ independently of one another are 0, 1 or 2, preferably:

diphenylmethoxyacetic acid, ethyl diphenylmethoxyacetate, methyl diphenylmethoxyacetate (CAS Reg. No.: 41858-19-9) (S7-1).

S8) Compounds of the formula (S8), as described in WO-A-98/27049,

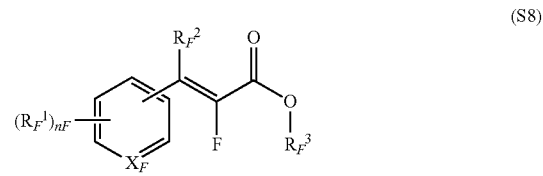

in which $X_F$ is CH or N, $n_F$ is, if $X_F$=N, an integer from 0 to 4 and is, if $X_F$=CH, an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4$-alkylthio, $(C_1-C_4)$-alkylsulphonyl, $(C_1-C_4)$-alkoxycarbonyl, optionally substituted phenyl, optionally substituted phenoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof, preferably compounds in which $X_F$ is CH, $n_F$ is an integer from 0 to 2, $R_F^1$ is halogen, $(C_1-C_4)$-alkyl, $(C_1-C_4)$-haloalkyl, $(C_1-C_4)$-alkoxy, $(C_1-C_4)$-haloalkoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.

S10) Compounds of the formula (S10a) or (S10$^b$) as described in WO-A-2007/023719 and WO-A-2007/023764

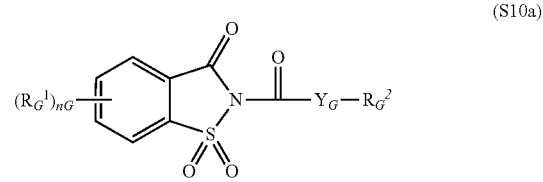

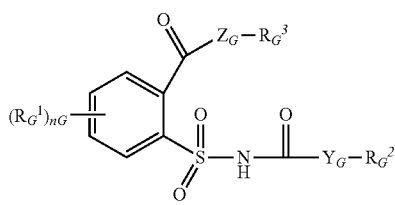

in which
R_G^1 is halogen, $(C_1\text{-}C_4)$-alkyl, methoxy, nitro, cyano, $CF_3$, $OCF_3$;
$Y_G$, $Z_G$ independently of one another are O or S,
$n_G$ is an integer from 0 to 4,
$R_G^2$ is $(C_1\text{-}C_{16})$-alkyl, $(C_2\text{-}C_6)$-alkenyl, $(C_3\text{-}C_6)$-cycloalkyl, aryl, benzyl, halobenzyl,
$R_G^3$ is hydrogen or $(C_1\text{-}C_6)$-alkyl.

S11) Active compounds of the type of the oxyimino compounds (S11), which are known as seed dressings, such as, for example, "oxabetrinil" ((Z)-1,3-dioxolan-2-ylmethoxyimino(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (511-2), which is known as seed dressing safener for millet against metolachlor damage, and "cyometrinil" or "CGA-43089" ((Z)-cyanomethoxyimino(phenyl)acetonitrile) (S11-3), which is known as seed dressing safener for millet against metolachlor damage.

S12) Active compounds from the class of the isothiochromanones (S12), such as, for example, methyl [(3-oxo-1H-2-benzothiopyran-4(3H)ylidene)methoxy]acetate (CAS Reg. No.: 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as safener for pretilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL-304415" (CAS Reg. No.: 31541-57-8) (4-carboxy-3,4-dihydro-2H-1-benzopyran-4-acetic acid) (S13-4) from American Cyanamid, which is known as safener for corn against imidazolinone damage, "MG-191" (CAS Reg. No.: 96420-72-3) (2-dichloromethyl-2-methyl-1,3-dioxolane) (S13-5) from Nitrokemia, which is known as safener for corn, "MG-838" (CAS Reg. No.: 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active compounds which, besides a herbicidal effect against harmful plants, also have a safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulphuron herbicide damage, "cumyluron"="JC-940" (3-(2-chlorophenylmethyl)-1-(1-methyl-1-phenyl-ethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulphonyl)benzene) from Kumiai, (CAS Reg. No. 54091-06-4), which is known as safener against some herbicide damage in rice.

S15) Compounds of the formula (S15) or tautomers thereof

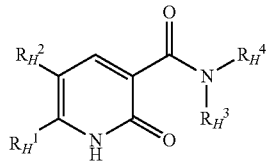

as described in WO-A-2008/131861 and WO-A-2008/131860
in which
$R_H^1$ represents a $(C_1\text{-}C_6)$haloalkyl radical and
$R_H^2$ represents hydrogen or halogen and
$R_H^3$, $R_H^4$ independently of one another represent hydrogen, $(C_1\text{-}C_{16})$-alkyl, $(C_2\text{-}C_{16})$-alkenyl or $(C_2\text{-}C_{16})$-alkynyl,
where each of the 3 last-mentioned radicals is unsubstituted or substituted by one or more radicals from the group consisting of halogen, hydroxy, cyano, $(C_1\text{-}C_4)$-alkoxy, $(C_1\text{-}C_4)$-haloalkoxy, $(C_1\text{-}C_4)$-alkylthio, $(C_1\text{-}C_4)$-alkylamino, di[$(C_1\text{-}C_4)$-alkyl]amino, [$(C_1\text{-}C_4)$-alkoxy]carbonyl, [$(C_1\text{-}C_4)$-haloalkoxy]carbonyl, $(C_3\text{-}C_6)$-cycloalkyl, which is unsubstituted or substituted, phenyl, which is unsubstituted or substituted, and heterocyclyl, which is unsubstituted or substituted,
or $(C_3\text{-}C_6)$-cycloalkyl, $(C_4\text{-}C_6)$-cycloalkenyl, $(C_3\text{-}C_6)$-cycloalkyl which is condensed on one side of the ring to a 4- to 6-membered saturated or unsaturated carbocyclic ring, or $(C_4\text{-}C_6)$-cycloalkenyl which is condensed on one side of the ring to a 4- to 6-membered saturated or unsaturated carbocyclic ring,
where each of the 4 last-mentioned radicals is unsubstituted or substituted by one or more radicals from the group consisting of halogen, hydroxy, cyano, $(C_1\text{-}C_4)$-alkyl, $(C_1\text{-}C_4)$-haloalkyl, $(C_1\text{-}C_4)$-alkoxy, $(C_1\text{-}C_4)$-haloalkoxy, $(C_1\text{-}C_4)$-alkylthio, $(C_1\text{-}C_4)$-alkylamino, di[$(C_1\text{-}C_4)$-alkyl]amino, [$(C_1\text{-}C_4)$-alkoxy]carbonyl, [$(C_1\text{-}C_4)$-haloalkoxy]carbonyl, $(C_3\text{-}C_6)$-cycloalkyl, which is unsubstituted or substituted, phenyl, which is unsubstituted or substituted, and heterocyclyl, which is unsubstituted or substituted,
or
$R_H^3$ represents $(C_1\text{-}C_4)$-alkoxy, $(C_2\text{-}C_4)$-alkenyloxy, $(C_2\text{-}C_6)$-alkinyloxy or $(C_2\text{-}C_4)$-haloalkoxy and $R_H^4$ represents hydrogen or $(C_1-C_4)$-alkyl or $R_H^3$ and $R_H^4$ together with the directly attached nitrogen atom represent a 4- to 8-membered heterocyclic ring which, in addition to the nitrogen atom, may also contain further hetero ring atoms, preferably up to two further hetero ring atoms from the group consisting of N, O and S, and which is unsubstituted or substituted by one or more radicals from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are primarily used as herbicides, but also have safener effect on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

The most preferred crop plant compatibility-improving compounds [components (b')] are cloquintocet-mexyl, fenchlorazole-ethyl, isoxadifen-ethyl, mefenpyr-diethyl, fenclorim, cumyluron, S4-1 and S4-5, and particular emphasis is given to cloquintocet-mexyl and mefenpyr-diethyl.

Surprisingly, it has now been found that the above-defined active compound combinations of compounds of the general formula (I) and safeners (antidotes) of group (b) listed above, whilst being tolerated very well by crop plants, have particularly high herbicidal activity and can be used in various crops, in particular in cereal (especially wheat), but also in soya beans, potatoes, maize and rice, for the selective control of weeds.

Here, it has to be considered to be surprising that, from a large number of known safeners or antidotes which are capable of antagonizing the damaging effect of a herbicide on the crop plants, it is in particular the abovementioned compounds of group (b) which neutralize the damaging effect of the compounds of formula (I) on the crop plants virtually completely without negatively affecting the herbicidal activity with respect to the weeds.

Emphasis is given here to the particularly advantageous effect of the particularly and most preferred combination partners from group (b'), in particular in respect of sparing cereal plants, such as, for example, wheat, barley and rye, but also maize and rice, as crop plants.

The formula (I) provides a general definition of the compounds according to the invention. Preferred substituents or ranges of the radicals given in the formulae above and below are illustrated below:

W preferably represents halogen or $C_1-C_4$-alkyl,

X preferably represents halogen, $C_1-C_6$-alkyl or $C_1-C_6$-haloalkyl,

Z preferably represents a radical

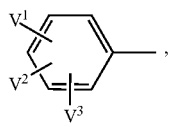

$V^1$ preferably represents hydrogen, halogen, $C_1-C_6$-alkyl, $C_1-C_6$-alkoxy, $C_1-C_6$-alkylthio, $C_1-C_6$-alkylsulphynyl, $C_1-C_6$-alkylsulphonyl, $C_1-C_4$-haloalkyl, $C_1-C_4$-haloalkoxy, nitro or cyano, $V^2$ preferably represents hydrogen, halogen, $C_1-C_6$-alkyl or $C_1-C_6$-alkoxy, $V^3$ preferably represents hydrogen, halogen, $C_1-C_6$-alkyl or $C_1-C_6$-alkoxy, Y preferably represents hydrogen, halogen, $C_1-C_6$-alkyl, $C_1-C_6$-haloalkyl, $C_1-C_6$-alkoxy or $C_1-C_6$-haloalkoxy, with the proviso that at least one of the radicals W or X represents halogen or ethyl, CKE preferably represents one of the groups

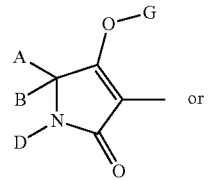

(1)

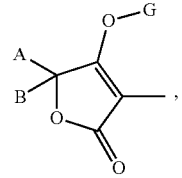

(2)

A preferably represents hydrogen or in each case optionally halogen-substituted $C_1-C_{12}$-alkyl, $C_3-C_8$-alkenyl, $C_1-C_{10}$-alkoxy-$C_1-C_8$-alkyl, $C_1-C_{10}$-alkylthio-$C_1-C_6$-alkyl, optionally halogen-, $C_1-C_6$-alkyl- or $C_1-C_6$-alkoxy-substituted $C_3-C_8$-cycloalkyl, in which optionally one or two not directly adjacent ring members are replaced by oxygen and/or sulphur or represents in each case optionally halogen-, $C_1-C_6$-alkyl-, $C_1-C_6$-haloalkyl-, $C_1-C_6$-alkoxy-, $C_1-C_6$-haloalkoxy-, cyano- or nitro-substituted phenyl, naphthyl, hetaryl having 5 or 6 ring atoms (for example furanyl, pyridyl, imidazolyl, triazolyl, pyrazolyl, pyrimidyl, thiazolyl or thienyl), phenyl-$C_1-C_6$-alkyl or naphthyl-$C_1-C_6$-alkyl, B preferably represents hydrogen, $C_1-C_{12}$-alkyl or $C_1-C_8$-alkoxy-$C_1-C_6$-alkyl or A, B and the carbon atom to which they are attached preferably represent saturated $C_3-C_{10}$-cycloalkyl or unsaturated $C_5-C_{10}$-cycloalkyl, in which optionally one ring member is replaced by oxygen, nitrogen or sulphur and which are optionally mono- or disubstituted by $C_1-C_8$-alkyl, $C_1-C_8$-alkoxy, $C_3-C_8$-alkenyloxy, $C_1-C_6$-alkoxy-$C_1-C_6$-alkyl, $C_1-C_6$-alkoxy-$C_1-C_6$-alkoxy, $C_3-C_6$-cycloalkyl-$C_1-C_2$-alkoxy, $C_3-C_{10}$-cycloalkyl, $C_1-C_8$-halo-alkyl or $C_2-C_6$-haloalkoxy or $C_1-C_6$-alkoxy-$C_1-C_4$-alkoxy, where the radicals mentioned above are also suitable as substituents at nitrogen, or A, B and the carbon atom to which they are attached preferably represent $C_3-C_6$-cycloalkyl which is substituted by an alkylenediyl group which is optionally substituted by $C_1-C_4$-alkyl and optionally contains one or two not directly adjacent oxygen and/or sulphur atoms, or by an alkylenedioxyl or by an alkylenedithioyl group which, together with the carbon atom to which it is attached, forms a further five- to eight-membered ring or A, B and the carbon atom to which they are attached preferably represents $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanediendiyl in which optionally one methylene group is replaced by oxygen or sulphur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D together preferably represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case:

halogen, hydroxy, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1), A and D then together with the atoms to which they are attached represent, for example, the groups AD-1 to AD-10 mentioned further below) which may contain oxygen or sulphur, or which optionally contains one of the groups below

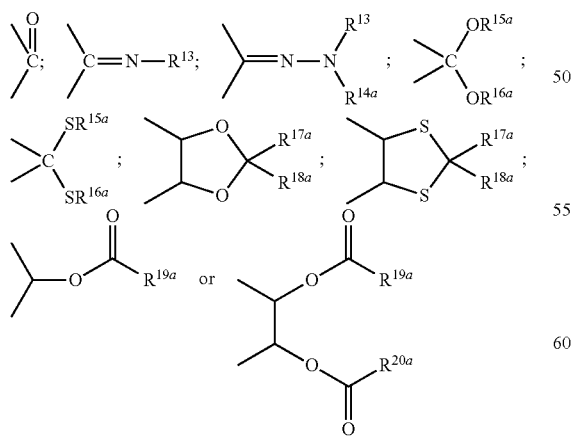

G preferably represents hydrogen (a) or represents one of the groups

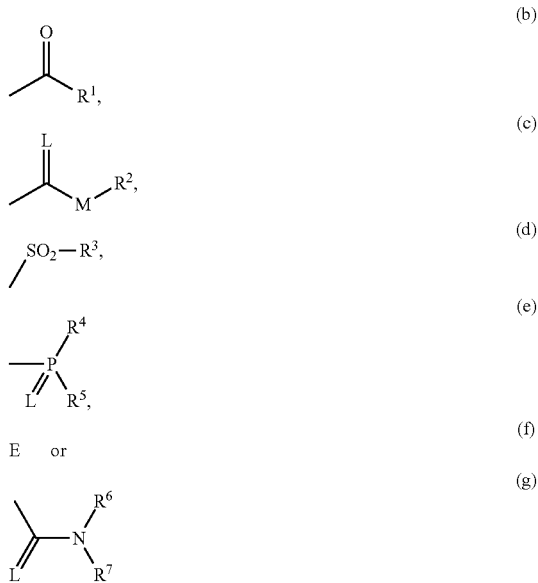

in particular (a), (b) or (c),
in which
E represents a metal ion or an ammonium ion,
L represents oxygen or sulphur and
M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-halo-alkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one methylene group is replaced by oxygen or sulphur, $R^{13}$ preferably represents hydrogen, represents in each case optionally halogen-substituted $C_1$-$C_8$-alkyl or $C_1$-$C_8$-alkoxy (only in the case of the C=N—$R^{13}$ group), represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl, hetaryl-$C_1$-$C_4$-alkyl, or, only in the case of the C=N—$R^{13}$ group, represents phenyl-$C_1$-$C_4$-alkoxy or hetaryl-$C_1$-$C_4$-alkoxy, $R^{14a}$ preferably represents hydrogen or $C_1$-$C_8$-alkyl or $R^{13}$ and $R^{14a}$ together preferably represent optionally $C_1$-$C_4$-alkyl-substituted $C_4$-$C_6$-alkanediyl which may optionally be interrupted by oxygen or sulphur, $R^{15a}$ and $R^{16a}$ are identical or different and preferably represent $C_1$-$C_6$-alkyl or $R^{15a}$ and $R^{16a}$ together preferably represent a $C_2$-$C_4$-alkanediyl radical or $C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, in particular fluorine, chlorine and bromine.

W particularly preferably represents methyl, ethyl, fluorine or chlorine,

X particularly preferably represents chlorine, bromine, $C_1$-$C_4$-alkyl or trifluoromethyl, Y particularly preferably represents hydrogen, $C_1$-$C_4$-alkyl, fluorine, chlorine, bromine, methoxy or trifluoromethyl, Z particularly preferably represents the radical

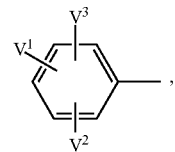

$V^1$ particularly preferably represents hydrogen, fluorine, chlorine, bromine, $C_1$-$C_6$-alkyl, $C_1$-$C_4$-alkoxy, $C_1$-$C_2$-haloalkyl or $C_1$-$C_2$-haloalkoxy, $V^2$ particularly preferably represents hydrogen, fluorine, chlorine, bromine, $C_1$-$C_4$-alkyl or $C_1$-$C_4$-alkoxy, $V^3$ particularly preferably represents hydrogen, fluorine or chlorine, with the proviso that at least one of the radicals W or X represents chlorine or ethyl, CKE particularly preferably represents one of the groups

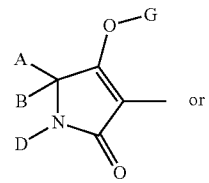

(1)

or

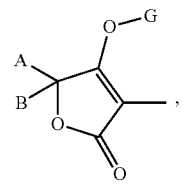

(2)

A particularly preferably represents hydrogen, represents $C_1$-$C_6$-alkyl, $C_1$-$C_4$-alkoxy-$C_1$-$C_2$-alkyl, each of which is optionally mono- to trisubstituted by fluorine and/or chlorine, represents $C_3$-$C_6$-cycloalkyl which is optionally mono- or disubstituted by $C_1$-$C_2$-alkyl or $C_1$-$C_2$-alkoxy and optionally interrupted by an oxygen atom or represents phenyl, pyridyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl or $C_1$-$C_2$-alkoxyl-$C_1$-$C_2$-alkyl or A, B and the carbon atom to which they are attached particularly preferably represent saturated or unsaturated $C_3$-$C_7$-cycloalkyl in which optionally one ring member is replaced by oxygen, nitrogen or sulphur and which is optionally mono- or disubstituted by $C_1$-$C_6$-alkyl, $C_1$-$C_4$-alkoxy-$C_1$-$C_2$-alkyl, trifluoromethyl, $C_1$-$C_6$-alkoxy, $C_3$-$C_6$-alkenyloxy, trifluoroethoxy, $C_1$-$C_3$-alkoxy-$C_1$-$C_3$-alkoxy or $C_3$-$C_6$-cycloalkylmethoxy, where the radicals mentioned above (but not trifluoromethyl) may also be suitable as substituents at nitrogen, A, B and the carbon atom to which they are attached particularly preferably represent $C_5$-$C_6$-cycloalkyl which is substituted by an alkylenediyl group which is optionally substituted by methyl or ethyl and optionally contains one or two not directly adjacent oxygen or sulphur atoms, or by an alkylenedioxyl group or by an alkylenedithiol group which, together with the carbon atom to which it is attached, forms a further five- or six-membered ring or A, B and the carbon atom to which they are attached particularly preferably represents $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, D particularly preferably represents hydrogen, represents $C_1$-$C_6$-alkyl, $C_3$-$C_6$-alkenyl, $C_1$-$C_4$-alkoxy-$C_1$-$C_3$-alkyl, each of which is optionally mono- to trisubstituted by fluorine, represents $C_3$-$C_6$-cycloalkyl which is optionally mono- or disubstituted by $C_1$-$C_4$-alkyl, $C_1$-$C_4$-alkoxy or $C_1$-$C_2$-haloalkyl and in which optionally one methylene group is replaced by oxygen or A and D together particularly preferably represent optionally mono- or disubstituted $C_3$-$C_5$-alkanediyl in which one methylene group may be replaced by oxygen or sulphur, possible substituents being $C_1$-$C_2$-alkyl or $C_1$-$C_2$-alkoxy, or A and D (in the case of the compounds of the formula (I-1)) together with the atoms to which they are attached represent one of the groups AD-1 to AD-10:

G particularly preferably represents hydrogen (a) or represents one of the groups in which E represents a metal ion equivalent or an ammonium ion, L represents oxygen or sulphur and M represents oxygen or sulphur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine,
represents $C_3$-$C_6$-cycloalkyl which is optionally monosubstituted by $C_1$-$C_2$-alkyl or $C_1$-$C_2$-alkoxy or
represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_8$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent a $C_4$-$C_5$-alkylene radical which is optionally substituted by methyl or ethyl and in which optionally one methylene group is replaced by oxygen or sulphur.

In the radical definitions mentioned as being particularly preferred, halogen represents fluorine, chlorine and bromine, in particular fluorine and chlorine.

W very particularly preferably represents methyl, ethyl or chlorine,

X very particularly preferably represents chlorine, methyl or ethyl,

Y very particularly preferably represents hydrogen, methyl, fluorine or chlorine, Z very particularly preferably represent the radical

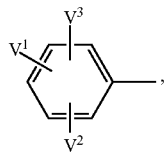

$V^1$ very particularly preferably represents hydrogen, fluorine, chlorine, methyl, ethyl, methoxy, ethoxy, trifluoromethyl or trifluoromethoxy, $V^2$ very particularly preferably represents hydrogen, fluorine or chlorine, $V^3$ very particularly preferably represents hydrogen or fluorine, with the proviso that at least one of the radicals W or X represents chlorine or ethyl, CKE very particularly preferably represents one of the groups

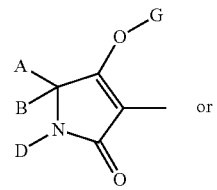

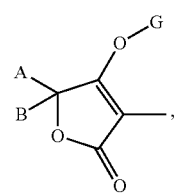

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl, represents phenyl which is optionally mono- or disubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen, methyl or ethyl or A, B and the carbon atom to which they are attached very particularly preferably represent saturated $C_5$-$C_6$-cycloalkyl in which optionally one ring member is replaced by oxygen, nitrogen or sulphur and which is optionally monosubstituted by methyl, ethyl, methoxymethyl, ethoxymethyl, methoxyethyl, ethoxyethyl, trifluoromethyl, methoxy, ethoxy, propoxy, butoxy, methoxyethoxy, ethoxyethoxy, allyloxy, trifluoroethoxy or cyclopropylmethoxy, where the radicals mentioned above (but not trifluoromethyl) are also suitable as substituents at nitrogen, or A, B and the carbon atom to which they are attached very particularly preferably represent $C_6$-cycloalkyl, which is optionally substituted by an alkylidenediyl group optionally interrupted by an oxygen atom or by an alkylenedioxyl group which contains two not directly adjacent oxygen atoms, where a further 5- or 6-membered ring is formed (which may optionally be mono- or disubstituted by methyl), or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, D very particularly preferably represents hydrogen, represents $C_1$-$C_4$-alkyl, $C_3$-$C_4$-alkenyl, $C_1$-$C_4$-alkoxy-$C_1$-$C_3$-alkyl, each of which is optionally mono- to trisubstituted by fluorine, or represents cyclopropyl, cyclopentyl or cyclohexyl, or A and D together very particularly preferably represent $C_3$-$C_5$-alkanediyl which is optionally monosubstituted by methyl or methoxy and in which optionally one carbon atom is replaced by oxygen or sulphur or represent the group AD-1, G very particularly preferably represents hydrogen (a) or represents one of the groups

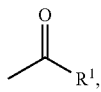
(b)

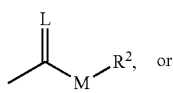
(c)

E,
(f)

in which

L represents oxygen or sulphur,

M represents oxygen or sulphur and

E represents a metal ion equivalent or an ammonium ion, $R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine.

W especially preferably represents methyl, ethyl or chlorine,

X especially preferably represents chlorine, methyl or ethyl,

Y especially preferably represents hydrogen or methyl,

Z especially preferably represents the radical

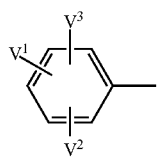 (notably 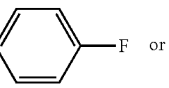 or

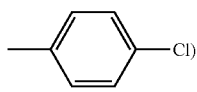)

$V^1$ especially preferably represents hydrogen, fluorine or chlorine, $V^2$ especially preferably represents hydrogen or fluorine, $V^3$ especially preferably represents hydrogen or fluorine, with the proviso that at least one of the radicals W or X represents chlorine or ethyl, CKE especially preferably represents the group

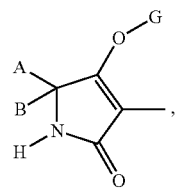
(1)

A, B and the carbon atom to which they are attached especially preferably represent saturated or unsaturated $C_6$-cycloalkyl in which optionally one ring member is replaced by oxygen and which is optionally monosubstituted by methoxy, G especially preferably represents hydrogen (a) or represents one of the groups

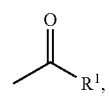
(b)

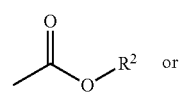
(c)

E
(f)

in which

E represents a metal ion equivalent (notably sodium), $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, (notably $C_1$-$C_6$-alkyl), $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, (notably $C_1$-$C_8$-alkyl), furthermore, W especially preferably also represents methyl, ethyl or chlorine (notably methyl or ethyl), X especially preferably also represents chlorine, methyl or ethyl (notably ethyl), Y especially preferably also represents hydrogen or methyl (notably hydrogen), Z especially preferably also represents the radical

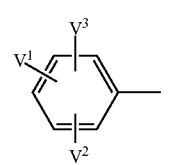 (notably 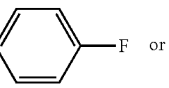 or

-continued

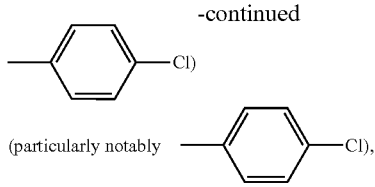

V¹ especially preferably also represents hydrogen, fluorine or chlorine,
V² especially preferably also represents hydrogen or fluorine,
V³ especially preferably also represents hydrogen or fluorine,
with the proviso that at least one of the radicals W or X represents chlorine or ethyl,
CKE especially preferably also represents the group

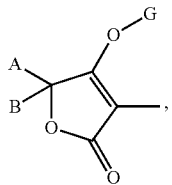 (2)

A, B and the carbon atom to which they are attached especially preferably represent saturated or unsaturated $C_6$-cycloalkyl in which optionally one ring member is replaced by oxygen and which is optionally monosubstituted by methoxy, or represent —$(CH_2)_2$—C(—$O(CH_2)_3$—)—$(CH_2)_2$—
G especially preferably represents hydrogen (a) or represents one of the groups

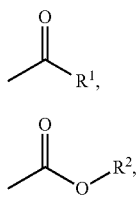

(notably hydrogen (a)), in which
R¹ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy (notably $C_1$-$C_6$-alkyl),
R² especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine (notably $C_1$-$C_8$-alkyl),
moreover
W especially preferably also represents methyl, ethyl or chlorine, (notably methyl or ethyl), X especially preferably also represents chlorine, methyl or ethyl, (notably ethyl),
Y especially preferably also represents hydrogen,
Z especially preferably also represents the radical

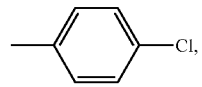

with the proviso that at least one of the radicals W or X represents chlorine or ethyl,
CKE especially preferably also represents the group

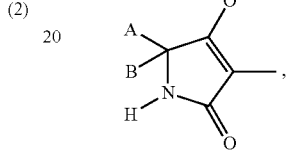 (1)

A B and the carbon atom to which they are attached especially preferably represent saturated or unsaturated $C_6$-cycloalkyl in which one ring member is replaced by nitrogen and which is monosubstituted by methoxy or ethoxy,
G especially preferably represents hydrogen (a) or represents one of the groups (b)

(c)

(f)
E 
(notably hydrogen (a)), in which
E represents a metal ion equivalent (notably sodium),
R¹ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy (notably $C_1$-$C_6$-alkyl),
R² especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine (notably $C_1$-$C_8$-alkyl),
W most preferably represents chlorine,
X most preferably represents methyl,
Y most preferably represents hydrogen, Z most preferably represents the radical

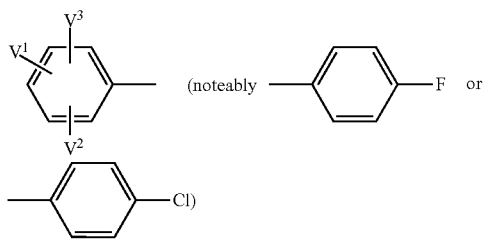

V¹ most preferably represents hydrogen, fluorine or chlorine,
V² most preferably represents hydrogen or fluorine,
V³ most preferably represents hydrogen or fluorine,
CKE most preferably represents the group

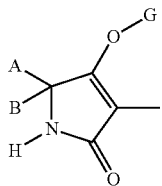 (1)

A, B and the carbon atom to which they are attached most preferably represent saturated or unsaturated $C_6$-cycloalkyl in which optionally one ring member is replaced by oxygen and which is optionally monosubstituted by methoxy,
G most preferably represents hydrogen (a) or represents one of the groups

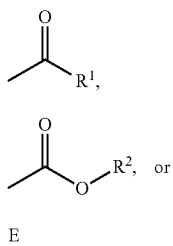

in which
E represents a metal ion equivalent (notably sodium),
R¹ most preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy (notably $C_1$-$C_6$-alkyl),
R² most preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine (notably $C_1$-$C_8$-alkyl), furthermore
W most preferably represents ethyl,
X most preferably represents ethyl,
Y most preferably represents hydrogen,
Z most preferably represents the radical

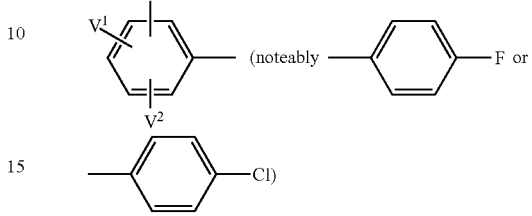

V¹ most preferably represents hydrogen, fluorine or chlorine,
V² most preferably represents hydrogen or fluorine,
V³ most preferably represents hydrogen or fluorine,
CKE most preferably represents the group

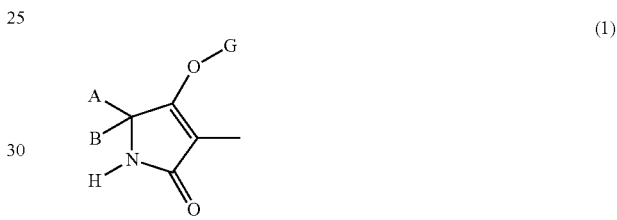 (1)

A, B and the carbon atom to which they are attached most preferably represent saturated or unsaturated $C_6$-cycloalkyl in which optionally one ring member is replaced by oxygen and which is optionally monosubstituted by methoxy,
G most preferably represents hydrogen (a) or represents one of the groups

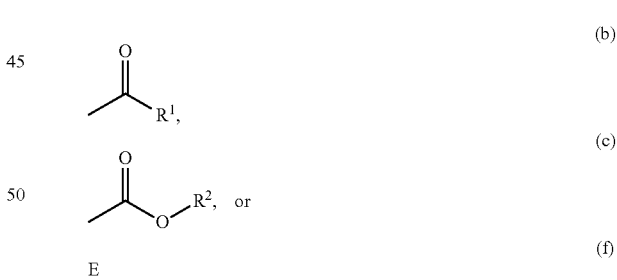

in which
E represents a metal ion equivalent (notably sodium),
R¹ most preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy, (notably $C_1$-$C_6$-alkyl), $R^2$ most preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, (notably $C_1$-$C_8$-alkyl).

The general or preferred radical definitions listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Most preference according to the invention is given to the compounds of the formula (I) which contain a combination of the meanings listed above as being most preferred.

Noteworthy are compounds where

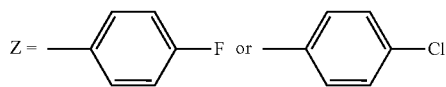

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

In addition to the compounds mentioned in the examples, the following compounds of the formula (I) may be specifically mentioned:

TABLE 1

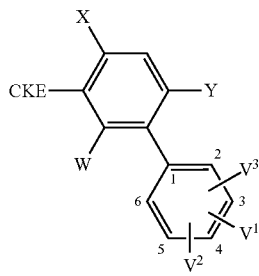

(I)

| W | X | Y | $V^1$ | $V^2$ | $V^3$ |
|---|---|---|---|---|---|
| Cl | $CH_3$ | H | 4-F | H | H |
| Cl | $CH_3$ | H | 4-Cl | H | H |
| Cl | $CH_3$ | H | 4-$CF_3$ | H | H |
| Cl | $CH_3$ | H | 4-$CH_3$ | H | H |
| Cl | $CH_3$ | H | 4-$OCH_3$ | H | H |
| Cl | $CH_3$ | H | 4-F | 3-F | H |
| Cl | $CH_3$ | H | 4-F | 3-Cl | H |
| Cl | $CH_3$ | H | 4-Cl | 3-F | H |
| Cl | $CH_3$ | H | 4-Cl | 3-Cl | H |
| Cl | $CH_3$ | H | 4-$CH_3$ | 3-F | H |
| Cl | $CH_3$ | H | 4-$CH_3$ | 3-Cl | H |
| Cl | $CH_3$ | H | 4-$OCH_3$ | 3-F | H |
| Cl | $CH_3$ | H | 4-$OCH_3$ | 3-Cl | H |
| Cl | $CH_3$ | H | 4-$CF_3$ | 3-F | H |
| Cl | $CH_3$ | H | 4-$CF_3$ | 3-Cl | H |
| Cl | $CH_3$ | H | 3-F | H | H |
| Cl | $CH_3$ | H | 3-Cl | H | H |
| Cl | $CH_3$ | H | 3-$CH_3$ | H | H |
| Cl | $CH_3$ | H | 3-$CH_3$ | 4-F | H |
| Cl | $CH_3$ | H | 3-$OCH_3$ | H | H |
| Cl | $CH_3$ | H | 3-$OCH_3$ | 4-F | H |
| Cl | $CH_3$ | H | 2-F | 4-F | H |
| Cl | $CH_3$ | H | 2-F | 4-Cl | H |
| Cl | $CH_3$ | H | 4-F | 5-F | 3-F |
| Cl | $CH_3$ | H | 4-F | 6-F | 2-F |
| Cl | $CH_3$ | H | 4-Cl | 5-F | 3-F |
| Cl | $CH_3$ | H | 2-F | 4-F | 5-F |
| Cl | $CH_3$ | H | 2-F | 4-F | 5-Cl |
| $CH_3$ | Cl | H | 4-F | H | H |
| $CH_3$ | Cl | H | 4-Cl | H | H |
| $CH_3$ | Cl | H | 4-$CF_3$ | H | H |
| $CH_3$ | Cl | H | 4-$CH_3$ | H | H |
| $CH_3$ | Cl | H | 4-$OCH_3$ | H | H |
| $CH_3$ | Cl | H | 4-F | 3-F | H |
| $CH_3$ | Cl | H | 4-F | 3-Cl | H |
| $CH_3$ | Cl | H | 4-Cl | 3-F | H |
| $CH_3$ | Cl | H | 4-Cl | 3-Cl | H |
| $CH_3$ | Cl | H | 4-$CH_3$ | 3-F | H |
| $CH_3$ | Cl | H | 4-$CH_3$ | 3-Cl | H |
| $CH_3$ | Cl | H | 4-$OCH_3$ | 3-F | H |
| $CH_3$ | Cl | H | 4-$OCH_3$ | 3-Cl | H |
| $CH_3$ | Cl | H | 4-$CF_3$ | 3-F | H |
| $CH_3$ | Cl | H | 4-$CF_3$ | 3-Cl | H |
| $CH_3$ | Cl | H | 3-F | H | H |
| $CH_3$ | Cl | H | 3-Cl | H | H |
| $CH_3$ | Cl | H | 3-$CH_3$ | H | H |
| $CH_3$ | Cl | H | 3-$CH_3$ | 4-F | H |
| $CH_3$ | Cl | H | 3-$OCH_3$ | H | H |
| $CH_3$ | Cl | H | 3-$OCH_3$ | 4-F | H |
| $CH_3$ | Cl | H | 2-F | 4-F | H |
| $CH_3$ | Cl | H | 2-F | 4-Cl | H |
| $CH_3$ | Cl | H | 4-F | 5-F | 3-F |
| $CH_3$ | Cl | H | 4-F | 6-F | 2-F |
| $CH_3$ | Cl | H | 4-Cl | 5-F | 3-F |
| $CH_3$ | Cl | H | 2-F | 4-F | 5-F |
| $CH_3$ | Cl | H | 2-F | 4-F | 5-Cl |
| Cl | Cl | H | 4-F | H | H |
| Cl | Cl | H | 4-Cl | H | H |
| Cl | Cl | H | 4-$CF_3$ | H | H |
| Cl | Cl | H | 4-$CH_3$ | H | H |
| Cl | Cl | H | 4-$OCH_3$ | H | H |
| Cl | Cl | H | 4-F | 3-F | H |
| Cl | Cl | H | 4-F | 3-Cl | H |
| Cl | Cl | H | 4-Cl | 3-F | H |
| Cl | Cl | H | 4-Cl | 3-Cl | H |
| Cl | Cl | H | 4-$CH_3$ | 3-F | H |
| Cl | Cl | H | 4-$CH_3$ | 3-Cl | H |
| Cl | Cl | H | 4-$OCH_3$ | 3-F | H |
| Cl | Cl | H | 4-$OCH_3$ | 3-Cl | H |

TABLE 1-continued

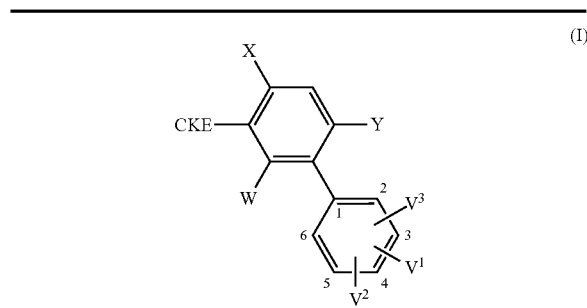

| W | X | Y | $V^1$ | $V^2$ | $V^3$ |
|---|---|---|---|---|---|
| Cl | Cl | H | 4-$CF_3$ | 3-F | H |
| Cl | Cl | H | 4-$CF_3$ | 3-Cl | H |
| Cl | Cl | H | 3-F | H | H |
| Cl | Cl | H | 3-Cl | H | H |
| Cl | Cl | H | 3-$CH_3$ | H | H |
| Cl | Cl | H | 3-$CH_3$ | 4-F | H |
| Cl | Cl | H | 3-$OCH_3$ | H | H |
| Cl | Cl | H | 3-$OCH_3$ | 4-F | H |
| Cl | Cl | H | 2-F | 4-F | H |
| Cl | Cl | H | 2-F | 4-Cl | H |
| Cl | Cl | H | 4-F | 5-F | 3-F |
| Cl | Cl | H | 4-F | 6-F | 2-F |
| Cl | Cl | H | 4-Cl | 5-F | 3-F |
| Cl | Cl | H | 2-F | 4-F | 5-F |
| Cl | Cl | H | 2-F | 4-F | 5-Cl |
| $C_2H_5$ | $CH_3$ | H | 4-F | H | H |
| $C_2H_5$ | $CH_3$ | H | 4-Cl | H | H |
| $C_2H_5$ | $CH_3$ | H | 4-$CF_3$ | H | H |
| $C_2H_5$ | $CH_3$ | H | 4-$CH_3$ | H | H |
| $C_2H_5$ | $CH_3$ | H | 4-$OCH_3$ | H | H |
| $C_2H_5$ | $CH_3$ | H | 4-F | 3-F | H |
| $C_2H_5$ | $CH_3$ | H | 4-F | 3-Cl | H |
| $C_2H_5$ | $CH_3$ | H | 4-Cl | 3-F | H |
| $C_2H_5$ | $CH_3$ | H | 4-Cl | 3-Cl | H |
| $C_2H_5$ | $CH_3$ | H | 4-$CH_3$ | 3-F | H |
| $C_2H_5$ | $CH_3$ | H | 4-$CH_3$ | 3-Cl | H |
| $C_2H_5$ | $CH_3$ | H | 4-$OCH_3$ | 3-F | H |
| $C_2H_5$ | $CH_3$ | H | 4-$OCH_3$ | 3-Cl | H |
| $C_2H_5$ | $CH_3$ | H | 4-$CF_3$ | 3-F | H |
| $C_2H_5$ | $CH_3$ | H | 4-$CF_3$ | 3-Cl | H |
| $C_2H_5$ | $CH_3$ | H | 3-F | H | H |
| $C_2H_5$ | $CH_3$ | H | 3-Cl | H | H |
| $C_2H_5$ | $CH_3$ | H | 3-$CH_3$ | H | H |
| $C_2H_5$ | $CH_3$ | H | 3-$CH_3$ | 4-F | H |
| $C_2H_5$ | $CH_3$ | H | 3-$OCH_3$ | H | H |
| $C_2H_5$ | $CH_3$ | H | 3-$OCH_3$ | 4-F | H |
| $C_2H_5$ | $CH_3$ | H | 2-F | 4-F | H |
| $C_2H_5$ | $CH_3$ | H | 2-F | 4-Cl | H |
| $C_2H_5$ | $CH_3$ | H | 4-F | 5-F | 3-F |
| $C_2H_5$ | $CH_3$ | H | 4-F | 6-F | 2-F |
| $C_2H_5$ | $CH_3$ | H | 4-Cl | 5-F | 3-F |
| $C_2H_5$ | $CH_3$ | H | 2-F | 4-F | 5-F |
| $C_2H_5$ | $CH_3$ | H | 2-F | 4-F | 5-Cl |
| $CH_3$ | $C_2H_5$ | H | 4-F | H | H |
| $CH_3$ | $C_2H_5$ | H | 4-Cl | H | H |
| $CH_3$ | $C_2H_5$ | H | 4-$CF_3$ | H | H |
| $CH_3$ | $C_2H_5$ | H | 4-$CH_3$ | H | H |
| $CH_3$ | $C_2H_5$ | H | 4-$OCH_3$ | H | H |
| $CH_3$ | $C_2H_5$ | H | 4-F | 3-F | H |
| $CH_3$ | $C_2H_5$ | H | 4-F | 3-Cl | H |
| $CH_3$ | $C_2H_5$ | H | 4-Cl | 3-F | H |
| $CH_3$ | $C_2H_5$ | H | 4-Cl | 3-Cl | H |
| $CH_3$ | $C_2H_5$ | H | 4-$CH_3$ | 3-F | H |
| $CH_3$ | $C_2H_5$ | H | 4-$CH_3$ | 3-Cl | H |
| $CH_3$ | $C_2H_5$ | H | 4-$OCH_3$ | 3-F | H |
| $CH_3$ | $C_2H_5$ | H | 4-$OCH_3$ | 3-Cl | H |
| $CH_3$ | $C_2H_5$ | H | 4-$CF_3$ | 3-F | H |
| $CH_3$ | $C_2H_5$ | H | 4-$CF_3$ | 3-Cl | H |
| $CH_3$ | $C_2H_5$ | H | 3-F | H | H |
| $CH_3$ | $C_2H_5$ | H | 3-Cl | H | H |
| $CH_3$ | $C_2H_5$ | H | 3-$CH_3$ | H | H |
| $CH_3$ | $C_2H_5$ | H | 3-$CH_3$ | 4-F | H |
| $CH_3$ | $C_2H_5$ | H | 3-$OCH_3$ | H | H |

TABLE 1-continued

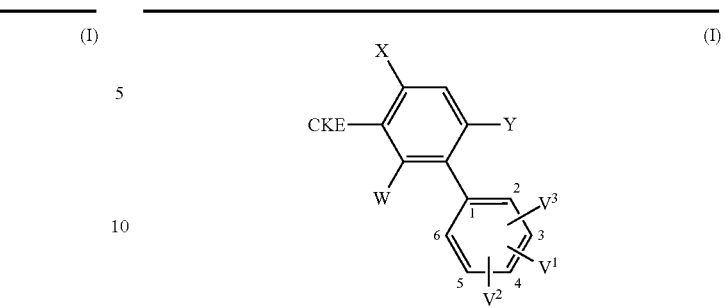

| W | X | Y | $V^1$ | $V^2$ | $V^3$ |
|---|---|---|---|---|---|
| $CH_3$ | $C_2H_5$ | H | 3-$OCH_3$ | 4-F | H |
| $CH_3$ | $C_2H_5$ | H | 2-F | 4-F | H |
| $CH_3$ | $C_2H_5$ | H | 2-F | 4-Cl | H |
| $CH_3$ | $C_2H_5$ | H | 4-F | 5-F | 3-F |
| $CH_3$ | $C_2H_5$ | H | 4-F | 6-F | 2-F |
| $CH_3$ | $C_2H_5$ | H | 4-Cl | 5-F | 3-F |
| $CH_3$ | $C_2H_5$ | H | 2-F | 4-F | 5-F |
| $CH_3$ | $C_2H_5$ | H | 2-F | 4-F | 5-Cl |
| $C_2H_5$ | $C_2H_5$ | H | 4-F | H | H |
| $C_2H_5$ | $C_2H_5$ | H | 4-Cl | H | H |
| $C_2H_5$ | $C_2H_5$ | H | 4-$CF_3$ | H | H |
| $C_2H_5$ | $C_2H_5$ | H | 4-$CH_3$ | H | H |
| $C_2H_5$ | $C_2H_5$ | H | 4-$OCH_3$ | H | H |
| $C_2H_5$ | $C_2H_5$ | H | 4-F | 3-F | H |
| $C_2H_5$ | $C_2H_5$ | H | 4-F | 3-Cl | H |
| $C_2H_5$ | $C_2H_5$ | H | 4-Cl | 3-F | H |
| $C_2H_5$ | $C_2H_5$ | H | 4-Cl | 3-Cl | H |
| $C_2H_5$ | $C_2H_5$ | H | 4-$CH_3$ | 3-F | H |
| $C_2H_5$ | $C_2H_5$ | H | 4-$CH_3$ | 3-Cl | H |
| $C_2H_5$ | $C_2H_5$ | H | 4-$OCH_3$ | 3-F | H |
| $C_2H_5$ | $C_2H_5$ | H | 4-$OCH_3$ | 3-Cl | H |
| $C_2H_5$ | $C_2H_5$ | H | 4-$CF_3$ | 3-F | H |
| $C_2H_5$ | $C_2H_5$ | H | 4-$CF_3$ | 3-Cl | H |
| $C_2H_5$ | $C_2H_5$ | H | 3-F | H | H |
| $C_2H_5$ | $C_2H_5$ | H | 3-Cl | H | H |
| $C_2H_5$ | $C_2H_5$ | H | 3-$CH_3$ | H | H |
| $C_2H_5$ | $C_2H_5$ | H | 3-$CH_3$ | 4-F | H |
| $C_2H_5$ | $C_2H_5$ | H | 3-$OCH_3$ | H | H |
| $C_2H_5$ | $C_2H_5$ | H | 3-$OCH_3$ | 4-F | H |
| $C_2H_5$ | $C_2H_5$ | H | 2-F | 4-F | H |
| $C_2H_5$ | $C_2H_5$ | H | 2-F | 4-Cl | H |
| $C_2H_5$ | $C_2H_5$ | H | 4-F | 5-F | 3-F |
| $C_2H_5$ | $C_2H_5$ | H | 4-F | 6-F | 2-F |
| $C_2H_5$ | $C_2H_5$ | H | 4-Cl | 5-F | 3-F |
| $C_2H_5$ | $C_2H_5$ | H | 2-F | 4-F | 5-F |
| $C_2H_5$ | $C_2H_5$ | H | 2-F | 4-F | 5-Cl |
| $CH_3$ | $C_2H_5$ | $CH_3$ | 4-F | H | H |
| $CH_3$ | $C_2H_5$ | $CH_3$ | 4-Cl | H | H |
| $CH_3$ | $C_2H_5$ | $CH_3$ | 4-$CF_3$ | H | H |
| $CH_3$ | $C_2H_5$ | $CH_3$ | 4-$CH_3$ | H | H |
| $CH_3$ | $C_2H_5$ | $CH_3$ | 4-$OCH_3$ | H | H |
| $CH_3$ | $C_2H_5$ | $CH_3$ | 4-F | 3-F | H |
| $CH_3$ | $C_2H_5$ | $CH_3$ | 4-F | 3-Cl | H |
| $CH_3$ | $C_2H_5$ | $CH_3$ | 4-Cl | 3-F | H |
| $CH_3$ | $C_2H_5$ | $CH_3$ | 4-Cl | 3-Cl | H |
| $CH_3$ | $C_2H_5$ | $CH_3$ | 4-$CH_3$ | 3-F | H |
| $CH_3$ | $C_2H_5$ | $CH_3$ | 4-$CH_3$ | 3-Cl | H |
| $CH_3$ | $C_2H_5$ | $CH_3$ | 4-$OCH_3$ | 3-F | H |
| $CH_3$ | $C_2H_5$ | $CH_3$ | 4-$OCH_3$ | 3-Cl | H |
| $CH_3$ | $C_2H_5$ | $CH_3$ | 4-$CF_3$ | 3-F | H |
| $CH_3$ | $C_2H_5$ | $CH_3$ | 4-$CF_3$ | 3-Cl | H |
| $CH_3$ | $C_2H_5$ | $CH_3$ | 3-F | H | H |
| $CH_3$ | $C_2H_5$ | $CH_3$ | 3-Cl | H | H |
| $CH_3$ | $C_2H_5$ | $CH_3$ | 3-$CH_3$ | H | H |
| $CH_3$ | $C_2H_5$ | $CH_3$ | 3-$CH_3$ | 4-F | H |
| $CH_3$ | $C_2H_5$ | $CH_3$ | 3-$OCH_3$ | H | H |
| $CH_3$ | $C_2H_5$ | $CH_3$ | 3-$OCH_3$ | 4-F | H |
| $CH_3$ | $C_2H_5$ | $CH_3$ | 2-F | 4-F | H |
| $CH_3$ | $C_2H_5$ | $CH_3$ | 2-F | 4-Cl | H |
| $CH_3$ | $C_2H_5$ | $CH_3$ | 4-F | 5-F | 3-F |
| $CH_3$ | $C_2H_5$ | $CH_3$ | 4-F | 6-F | 2-F |
| $CH_3$ | $C^2H_5$ | $CH_3$ | 4-Cl | 5-F | 3-F |

TABLE 1-continued (I structure with X, CKE, Y, W, V¹, V², V³ substituents on biphenyl)

| W | X | Y | V¹ | V² | V³ |
|---|---|---|-----|-----|-----|
| $CH_3$ | $C_2H_5$ | $CH_3$ | 2-F | 4-F | 5-F |
| $CH_3$ | $C_2H_5$ | $CH_3$ | 2-F | 4-F | 5-Cl |

Especially preferred active compounds according to the invention are compounds having the radical combinations for W, X, Y, V¹, V² and V³ listed in Table 1 and the radical combinations for A, B and D listed in Tables 2a and 2b.

TABLE 2a (Structure with A, B, OH, X, Y, W, V¹, V², V³ on pyrrolone-biphenyl)

CKE = (1)

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentyl | $CH_3$ | H |
| cyclohexyl | $CH_3$ | H |
| $H_3CO-CH_2-$ | $CH_3$ | H |

TABLE 2a-continued (same structure) CKE = (1)

| A | B | D |
|---|---|---|
| $H_5C_2O-CH_2-$ | $CH_3$ | H |
| $H_3CO-(CH_2)_2-$ | $CH_3$ | H |
| $H_5C_2O-(CH_2)_2-$ | $CH_3$ | H |
| 2-tetrahydrofuryl | $CH_3$ | H |
| 3-tetrahydrofuryl | $CH_3$ | H |
| $-(CH_2)_2-$ | | H |
| $-(CH_2)_4-$ | | H |
| $-(CH_2)_5-$ | | H |
| $-(CH_2)_6-$ | | H |
| $-(CH_2)_7-$ | | H |
| $-(CH_2)_2-O-(CH_2)_2-$ | | H |
| $-CH_2-O-(CH_2)_3-$ | | H |
| $-(CH_2)_2-S-(CH_2)_2-$ | | H |
| $-CH_2-CHCH_3-(CH_2)_3-$ | | H |
| $-CH_2-CHOCH_3-(CH_2)_2-$ | | H |
| $-CH_2-CHOC_2H_5-(CH_2)_2-$ | | H |
| $-CH_2-CHOC_3H_7-(CH_2)_2-$ | | H |
| $-CH_2-CHOC_4H_9-(CH_2)_2-$ | | H |
| $-CH_2-CHO(CH_2)_2OCH_3-(CH_2)_2-$ | | H |
| $-CH_2-CH(OCH_2\text{-cyclopropyl})-(CH_2)_2-$ | | H |
| $-CH_2-CHOCH_3-(CH_2)_3-$ | | H |
| $-CH_2-CHOC_2H_5-(CH_2)_3-$ | | H |
| $-CH_2-CHOC_3H_7-(CH_2)_3-$ | | H |
| $-CH_2-CHOC_4H_9-(CH_2)_3-$ | | H |
| $-CH_2-CHO(CH_2)_2OCH_3-(CH_2)_3-$ | | H |
| $-CH_2-CH(OCH_2\text{-cyclopropyl})-(CH_2)_3-$ | | H |
| $-(CH_2)_2-CHCH_3-(CH_2)_2-$ | | H |
| $-(CH_2)_2-CHC_2H_5-(CH_2)_2-$ | | H |
| $-(CH_2)_2-CHC_3H_7-(CH_2)_2-$ | | H |
| $-(CH_2)_2-CHi-C_3H_7-(CH_2)_2-$ | | H |
| $-(CH_2)_2-CHOCH_3-(CH_2)_2-$ | | H |
| $-(CH_2)_2-CHOC_2H_5-(CH_2)_2-$ | | H |
| $-(CH_2)_2-CHOC_3H_7-(CH_2)_2-$ | | H |
| $-(CH_2)_2-CHO-CH_2CF_3-(CH_2)_2-$ | | H |
| $-(CH_2)_2-CCH_3(OCH_3)-(CH_2)_2-$ | | H |
| $-(CH_2)_2-CC_2H_5(OCH_3)-(CH_2)_2-$ | | H |
| $-(CH_2)_2-CCH_3(OC_2H_5)-(CH_2)_2-$ | | H |
| $-(CH_2)_2-NOCH_3-(CH_2)_2-$ | | H |
| $-(CH_2)_2-NOC_2H_5-(CH_2)_2-$ | | H |
| $-(CH_2)_2-C(CH_3)_2-(CH_2)_2-$ | | H |
| $-CH_2-(CHCH_3)_2-(CH_2)_2-$ | | H |

TABLE 2a-continued
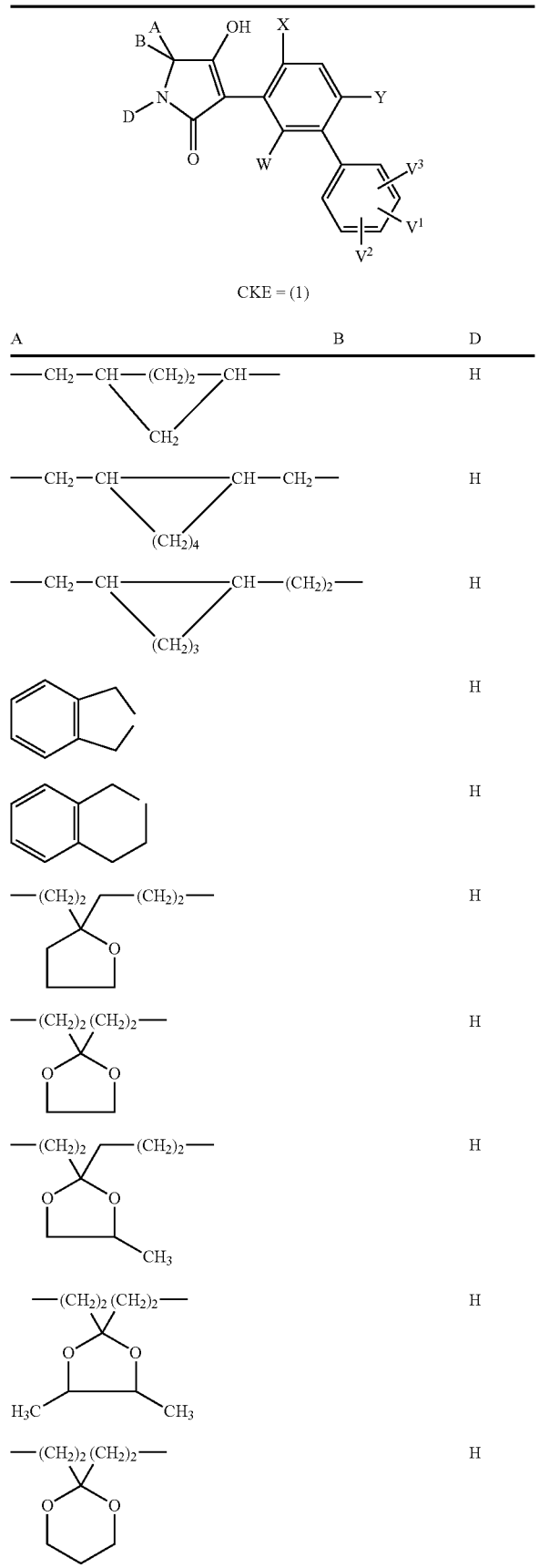
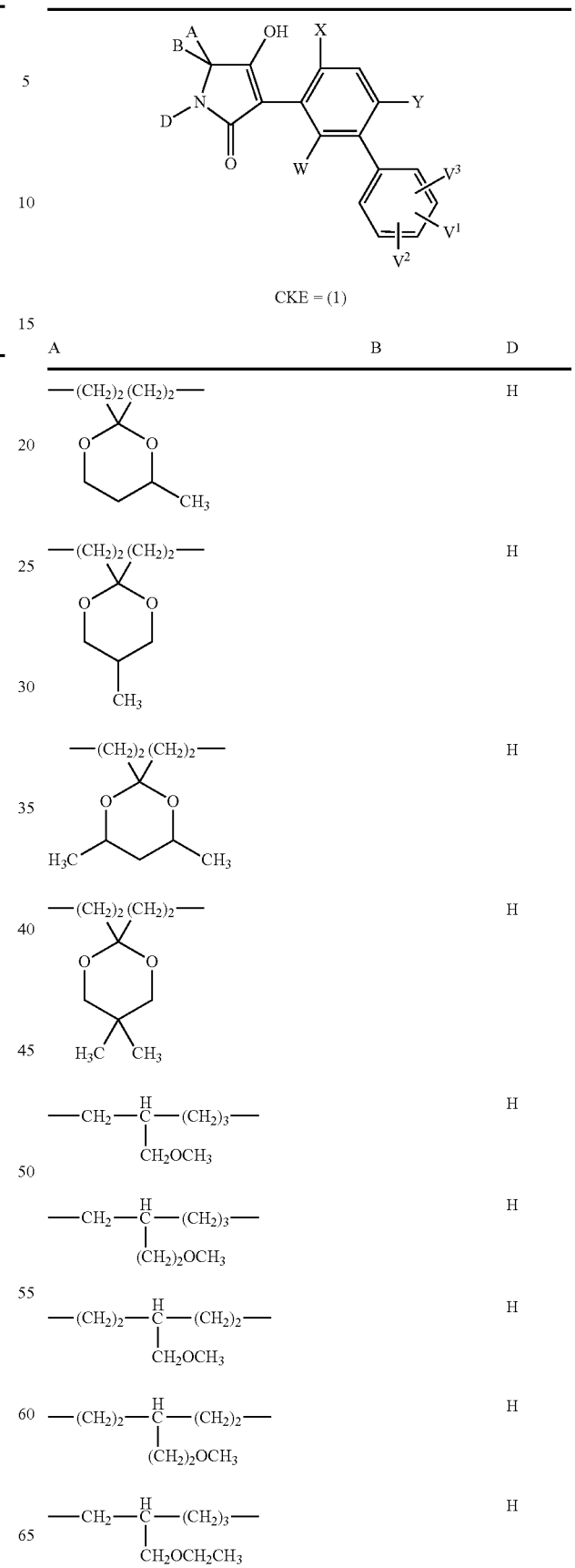

TABLE 2a-continued

CKE = (1)

Structure: pyrrolone with substituents A, B on C adjacent to N-D; OH on ring; connected to phenyl ring with X, Y, W substituents; phenyl bears another phenyl with V¹, V², V³.

| A | B | D |
|---|---|---|
| —CH₂—CH(—(CH₂)₂OCH₂CH₃)—(CH₂)₃— | | H |
| —(CH₂)₂—C(H)(CH₂OCH₂CH₃)—(CH₂)₂— | | H |
| —(CH₂)₂—C(H)(—(CH₂)₂OCH₂CH₃)—(CH₂)₂— | | H |

TABLE 2b

| A | D | B |
|---|---|---|
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—CH(OCH₃)—CH₂— | | H |
| —CH₂—CH=CH—CH₂— | | H |
| —CH₂—CH(—O—)CH—CH₂— (epoxide) | | H |
| —CH₂—S—CH₂— | | H |
| —CH₂—S—(CH₂)₂— | | H |
| —(CH₂)₂—S—CH₂— | | H |
| —CH₂—CH—CH— with —(CH₂)₃— bridge | | H |
| H | CH₃ | H |
| H | C₂H₅ | H |
| H | C₃H₇ | H |
| H | i-C₃H₇ | H |
| H | cyclopropyl | H |
| H | cyclopentyl | H |
| H | cyclohexyl | H |
| CH₃ | CH₃ | H |
| CH₃ | C₂H₅ | H |
| CH₃ | C₃H₇ | H |
| CH₃ | i-C₃H₇ | H |

TABLE 2b-continued

| A | D | B |
|---|---|---|
| CH₃ | cyclopropyl | H |
| CH₃ | cyclopentyl | H |
| CH₃ | cyclohexyl | H |
| C₂H₅ | CH₃ | H |
| C₂H₅ | C₂H₅ | H |
| H | H₃CO—(CH₂)₂— | H |
| H | H₅C₂O—(CH₂)₂— | H |
| H | H₃CO—CH₂—CH(CH₃)— | H |
| H | H₃CO—CHCH₃—CH₂— | H |
| CH₃ | H₃CO—(CH₂)₂— | H |
| CH₃ | H₅C₂O—(CH₂)₂— | H |
| CH₃ | H₃CO—CH₂—CH(CH₃)— | H |
| CH₃ | H₃CO—CHCH₃—CH₂— | H |

Noteworthy active compounds are especially preferred compounds having the radical combinations for W, X, Y, V¹, V² and V³ listed in Table 1 and the radical combinations for A, B and D listed in Tables 2a and 2b.

Suitable active compounds according to the invention are furthermore especially preferably compounds having the radical combinations for W, X, Y, V¹, V² and V³ listed in Table 1 and the radical combinations for A and B listed in Table 3.

TABLE 3

CKE = (2)

Structure: furanone with substituents A, B; OH on ring; connected to phenyl ring with X, W substituents; phenyl bears another phenyl ring (positions 1–6) with V¹, V², V³.

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |

TABLE 3-continued

[Structure: core scaffold with A, B on furanone ring; OH; X, W on phenyl; biphenyl with positions 1-6 and V¹, V², V³]

CKE = (2)

| A | B |
|---|---|
| cyclopentyl | CH₃ |
| cyclohexyl | CH₃ |
| H₃CO—CH₂— | CH₃ |
| H₅C₂O—CH₂— | CH₃ |
| H₃CO—(CH₂)₂— | CH₃ |
| H₅C₂O—(CH₂)₂— | CH₃ |
| 2-tetrahydrofuryl | CH₃ |
| 3-tetrahydrofuryl | CH₃ |

—(CH₂)₂—
—(CH₂)₄—
—(CH₂)₅—
—(CH₂)₆—
—(CH₂)₇—
—(CH₂)₂—O—(CH₂)₂—
—CH₂—O—(CH₂)₃—
—(CH₂)₂—S—(CH₂)₂—
—CH₂—CHCH₃—(CH₂)₃—
—CH₂—CHOCH₃—(CH₂)₃—
—CH₂—CHOC₂H₅—(CH₂)₃—
—CH₂—CHOC₃H₇—(CH₂)₃—
—CH₂—CHOC₄H₉—(CH₂)₃—
—CH₂—CHO(CH₂)₂OCH₃—(CH₂)₃—
—(CH₂)₂—CHCH₃—(CH₂)₂—
—(CH₂)₂—CHC₂H₅—(CH₂)₂—
—(CH₂)₂—CHC₃H₇—(CH₂)₂—
—(CH₂)₂—CHi—C₃H₇—(CH₂)₂—
—(CH₂)₂—CHOCH₃—(CH₂)₂—
—(CH₂)₂—CHOC₂H₅—(CH₂)₂—
—(CH₂)₂—CHOC₃H₇—(CH₂)₂—
—(CH₂)₂—CHO—CH₂CF₃—(CH₂)₂—
—(CH₂)₂—CCH₃(OCH₃)—(CH₂)₂—
—(CH₂)₂—CC₂H₅(OCH₃)—(CH₂)₂—
—(CH₂)₂—CCH₃(OC₂H₅)—(CH₂)₂—
—(CH₂)₂—NOCH₃—(CH₂)₂—
—(CH₂)₂—NOC₂H₅—(CH₂)₂—
—(CH₂)₂—C(CH₃)₂—(CH₂)₂—
—CH₂—(CHCH₃)₂—(CH₂)₂—

—CH₂—CH—(CH₂)₂—CH—
           |            |
           CH₂——————

—CH₂—CH————CH—CH₂—
        |        |
        (CH₂)₄

—CH₂—CH————CH—(CH₂)₂—
        |        |
        (CH₂)₃

[indane]

[tetrahydronaphthalene]

—(CH₂)₂—C(—(CH₂)₂—)(O—CH₂—CH₂—) (2,2-disubstituted tetrahydrofuran)

[2,2-bis(CH₂-linked) 1,3-dioxolane]

[2,2-bis(CH₂-linked) 4-methyl-1,3-dioxolane]

[2,2-bis(CH₂-linked) 4-CH₂—, 5-CH₃ 1,3-dioxolane]

[2,2-bis(CH₂-linked) 1,3-dioxane]

[2,2-bis(CH₂-linked) 4-methyl-1,3-dioxane]

TABLE 3-continued

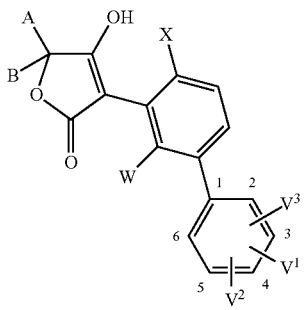

CKE = (2)

| A | B |
|---|---|
| 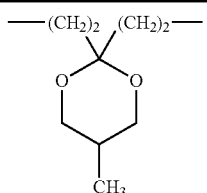 | |
| 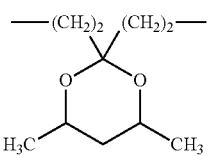 | |
| 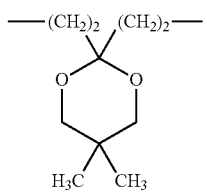 | |
| 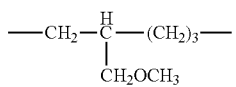 | |
| 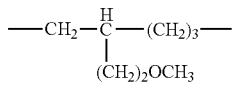 | |
| 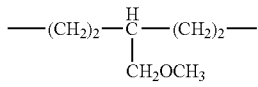 | |
| 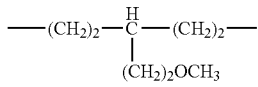 | |
| 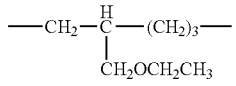 | |
| 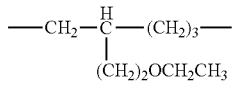 | |
| 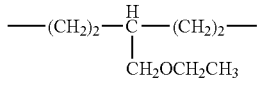 | |

TABLE 3-continued

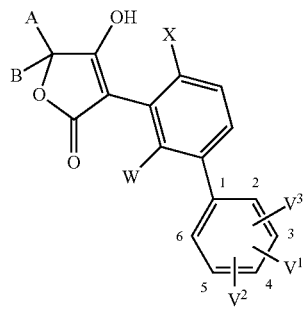

CKE = (2)

| A | B |
|---|---|
| 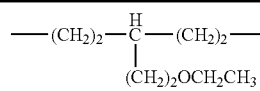 | |

Noteworthy active compounds are especially preferred compounds having the radical combinations for W, X, Y, $V^1$, $V^2$ and $V^3$ listed in Table 1 and the radical combinations for A and B listed in Table 3.

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. Nos. 4,844,734, 5,462,912, 5,538,937, US-A 03/0224939, US-A 05/0009880, US-A 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842,476). A boost of action by ammonium sulphate, for example, is described by way of example for the herbicides glyphosate, phosphinothricin and for phenyl-substituted cyclic ketoenols (U.S. Pat. No. 6,645,914, EP-A2 0 036 106, WO 07/068,427). A corresponding boost of action in insecticides has already been described in WO 07/068,428.

The use of ammonium sulphate as a formulating assistant has also been described for certain active compounds and applications (WO 92/16108), but its purpose therein is to stabilize the formulation, not to boost the action.

It has now been found, very surprisingly, that the action of insecticides and/or acaricides and/or nematicides and/or herbicides and/or fungicides from the class of the biphenyl-substituted cyclic ketoenols of the formula (I) can be boosted significantly through the addition of ammonium salts or phosphonium salts to the application solution or through the incorporation of these salts into a formulation comprising biphenyl-substituted cyclic ketoenols of the formula (I). The present invention therefore provides for the use of ammonium salts or phosphonium salts for boosting the action of crop protection compositions which comprise as their active compound insecticidal and/or acaricidal and/or nematicidal and/or herbicidal and/or fungicidal biphenyl-substituted cyclic ketoenols of the formula (I). The invention likewise provides compositions which comprise herbicidal and/or acaricidal and/or insecticidal and/or nematicidal and/or fungicidal biphenyl-substituted cyclic ketoenols of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth and/or fungi.

The compounds of the formula (I) possess a broad insecticidal and/or acaricidal and/or nematicidal and/or herbicidal and/or fungicidal activity, but in specific cases the activity and/or plant tolerance leaves something to be desired. However, some or all of these properties can be improved by adding ammonium salts or phosphonium salts.

The active compounds can be used in the compositions according to the invention in a broad concentration range. The concentration of the active compounds in the formulation is typically 0.1%-50% by weight.

The formula (III') provides a definition of the ammonium salts and phosphonium salts which, according to the invention, boost the activity of crop protection compositions comprising an active compound from the class of the biphenyl-substituted cyclic ketoenols of the formula (I)

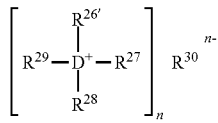
(III')

in which
D represents nitrogen or phosphorus,
D preferably represents nitrogen,
$R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26'}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26'}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26'}$, $R^{27}$, $R^{28}$ and $R^{29}$ very particularly preferably represent hydrogen,
n represents 1, 2, 3 or 4,
n preferably represents 1 or 2,
$R^{30}$ represents an organic or inorganic anion,
$R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30}$ particularly preferably represents lactate, sulphate, nitrate, thiosulphate, thiocyanate, oxalate or formate,
$R^{30}$ very particularly preferably represents sulphate.

The ammonium salts and phosphonium salts of the formula (III') can be used in a broad concentration range to boost the activity of crop protection compositions comprising biphenyl-substituted cyclic ketoenols of the formula (I). In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal and/or acaricidal and/or nematicidal and/or herbicidal and/or fungicidal biphenyl-substituted cyclic ketoenols of the formula (I) as active compound. The invention likewise provides compositions which comprise herbicidal and/or acaricidal and/or insecticidal and/or nematicidal and/or fungicidal biphenyl-substituted cyclic ketoenols of the formula (I), penetrants and ammonium salts and/or phosphonium salts, including specifically not only formulated active compounds but also ready-to-use compositions (spray liquors). The invention additionally provides, finally, for the use of these compositions for controlling harmful insects and/or spider mites and/or unwanted vegetation and/or fungi.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, *Pesticide Science* 51, 131-152) can be used for determining this property.

Examples of suitable penetrants include alkanol alkoxylates. Penetrants of the invention are alkanol alkoxylates of the formula (IV')

R—O-(-AO)$_v$—R'  (IV')

in which
R is straight-chain or branched alkyl having 4 to 20 carbon atoms,
R' is hydrogen, methyl, ethyl, n-propyl, isopropyl, n-butyl, isobutyl, tert-butyl, n-pentyl or n-hexyl,
AO is an ethylene oxide radical, a propylene oxide radical, a butylene oxide radical or is mixtures of ethylene oxide and propylene oxide radicals or butylene oxide radicals, and
v is a number from 2 to 30.

One preferred group of penetrants are alkanol alkoxylates of the formula

R—O-(-EO—)$_n$—R'  (IV'-a)

in which
R is as defined above,
R' is as defined above,
EO is —CH$_2$—CH$_2$—O—, and
n is a number from 2 to 20.

A further preferred group of penetrants are alkanol alkoxylates of the formula

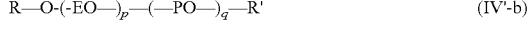
R—O-(-EO—)$_p$—(—PO—)$_q$—R'  (IV'-b)

in which
R is as defined above,
R' is as defined above,
EO is —CH$_2$—CH$_2$—O—, PO is

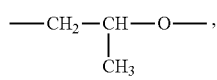

p is a number from 1 to 10, and
q is a number from 1 to 10.

A further preferred group of penetrants are alkanol alkoxylates of the formula

R—O—(—PO—)$_r$—(EO—)$_s$—R'  (IV'-c)

in which
R is as defined above,
R' is as defined above,
EO is —CH$_2$—CH$_2$—O—,
PO is

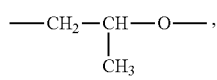

r is a number from 1 to 10, and
s is a number from 1 to 10.

A further preferred group of penetrants are alkanol alkoxylates of the formula

R—O—(-EO—)$_p$—(—BO—)$_q$—R'  (IV'-d)

in which
R and R' are as defined above,
EO is CH$_2$—CH$_2$—O—,
BO is

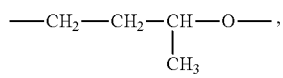

p is a number from 1 to 10 and
q is a number from 1 to 10.

A further preferred group of penetrants are alkanol alkoxylates of the formula

R—O—(—BO—)$_r$—(—EO—)$_s$—R'  (IV'-e)

in which
R and R' are as defined above,
BO is

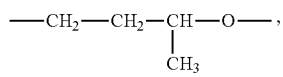

EO is CH$_2$—CH$_2$—O—,
r is a number from 1 to 10 and
s is a number from 1 to 10.

A further preferred group of penetrants are alkanol alkoxylates of the formula

CH$_3$—(CH$_2$)$_t$—CH$_2$—O—(—CH$_2$—CH$_2$—O—)$_u$—R'  (IV'-f)

in which
R' is as defined above,
t is a number from 8 to 13,
u is a number from 6 to 17.

In the formulae indicated above,
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula CH$_3$—CH$_2$—CH$_2$—CH$_2$—CH(C$_2$H$_5$)—CH$_2$—O—(PO)$_8$—(EO)$_6$—H  (IV'-c-1)

in which
EO is —CH$_2$—CH$_2$—O—,
PO is

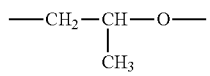

and
the numbers 8 and 6 represent average values.

As an example of an alkanol alkoxylate of the formula (IV'-d) mention may be made of the formula CH$_3$—(CH$_2$)$_{10}$—O-(-EO—)$_6$—(—BO—)$_2$—CH$_3$  (IV'-d-1)

in which
EO is CH$_2$—CH$_2$—O—,
BO is

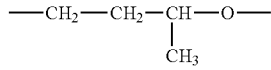

and
the numbers 10, 6 and 2 represent average values.

Particularly preferred alkanol alkoxylates of the formula (IV'-f) are compounds of this formula in which
t is a number from 9 to 12 and
u is a number from 7 to 9.

Mention may be made with very particular preference of alkanol alkoxylate of the formula (IV'-f-1)

CH$_3$—(CH$_2$)$_t$—CH$_2$—O—(—CH$_2$—CH$_2$—O—)$_u$—H  (IV'-f-1)

in which
t stands for the average value 10.5 and
u stands for the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40%, by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkyleneamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colourants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, according to process (A), ethyl N-[6-ethyl-2-methyl-3-(4-fluorophenyl)phenylacetyl]-1-aminocyclohexanecarboxylate as starting material, the course of the process according to the invention can be represented by the reaction scheme below:

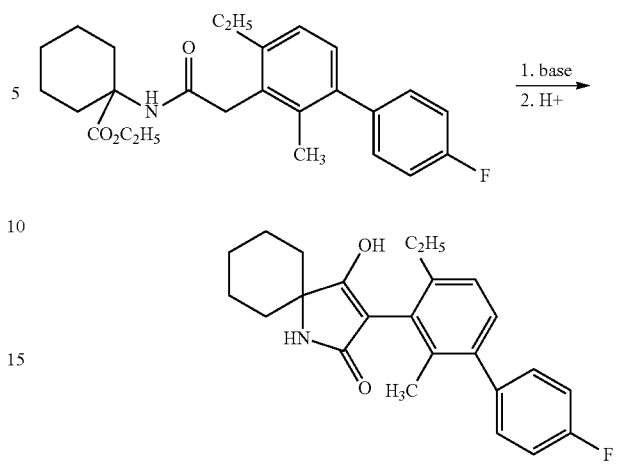

Using, according to process (B), ethyl O-[2-chloro-6-methyl-5-(4-fluorophenyl)phenylacetyl] 1-hydroxycyclopentanecarboxylate, the course of the process according to the invention can be represented by the reaction scheme below:

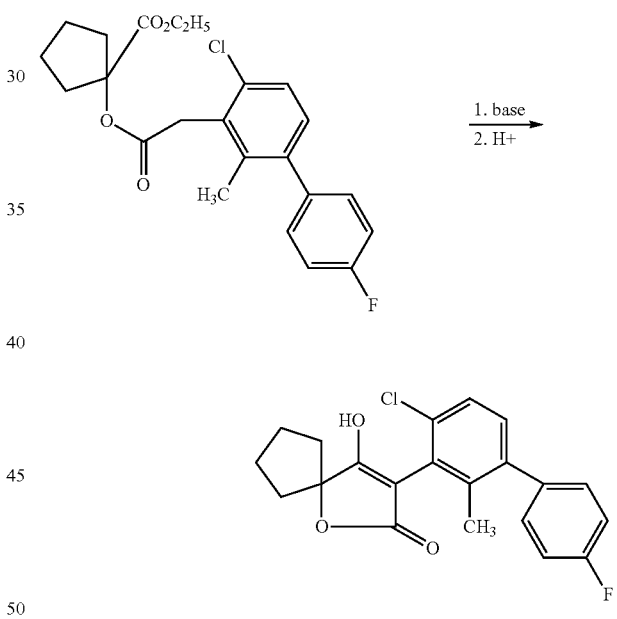

Using, according to process (C), 3-[(6-ethyl-2-methyl-3-bromo)phenyl]-4-hydroxy-1-azaspiro[4.5]-dec-3-en-2-one and 4-fluorophenylboronic acid as starting materials, the course of the reaction can be represented by the scheme below:

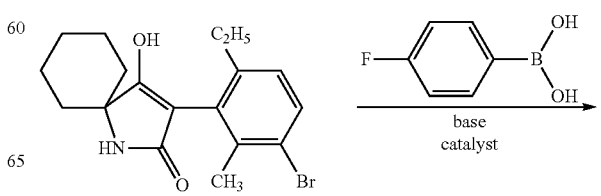

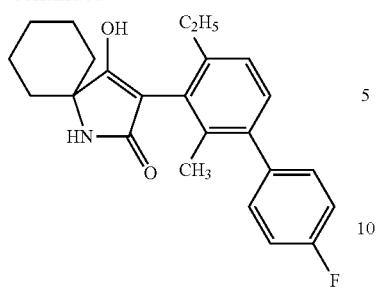

Using, according to process (Dα), 3-[(2-chloro-6-methyl-5-(4-fluorophenyl))phenyl]-4-hydroxy-1-azaspiro[5.4]dec-3-en-2-one and pivaloyl chloride as starting materials, the course of the process according to the invention can be represented by the reaction scheme below:

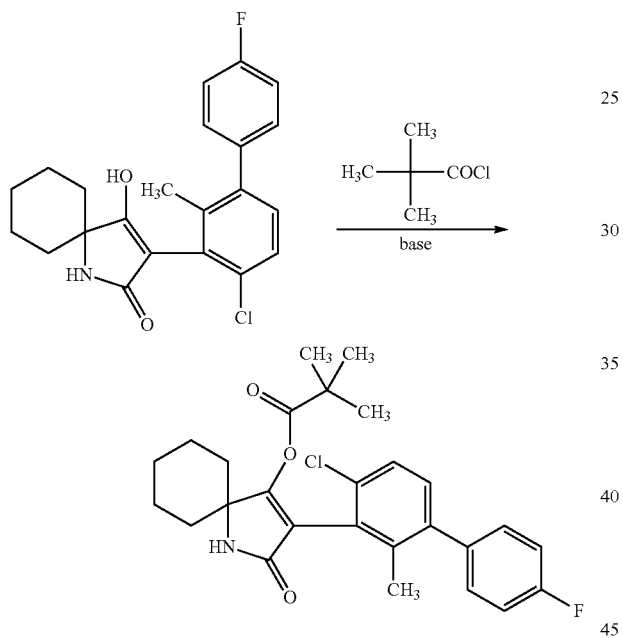

Using, according to process (D) (variant β), 3-[(6-ethyl-2-methyl-3-(4-fluorophenyl))phenyl]-4-hydroxy-1-oxaspiro[5.4]dec-3-en-2-one and acetic anhydride as starting materials, the course of the process according to the invention can be represented by the reaction scheme below:

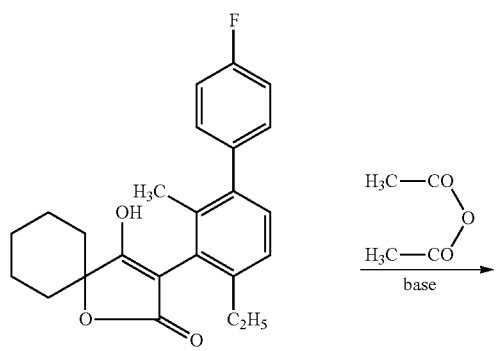

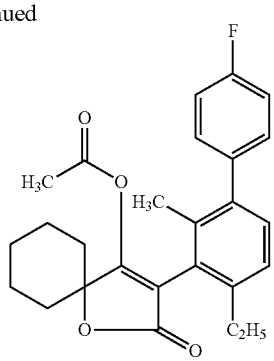

Using, according to process (E), 3-[2,6-diethyl-3-(4-fluorophenyl)phenyl]-4-hydroxy-1-azaspiro[5.4]dec-3-en-2-one and ethyl chloroformate as starting materials, the course of the process according to the invention can be represented by the reaction scheme below:

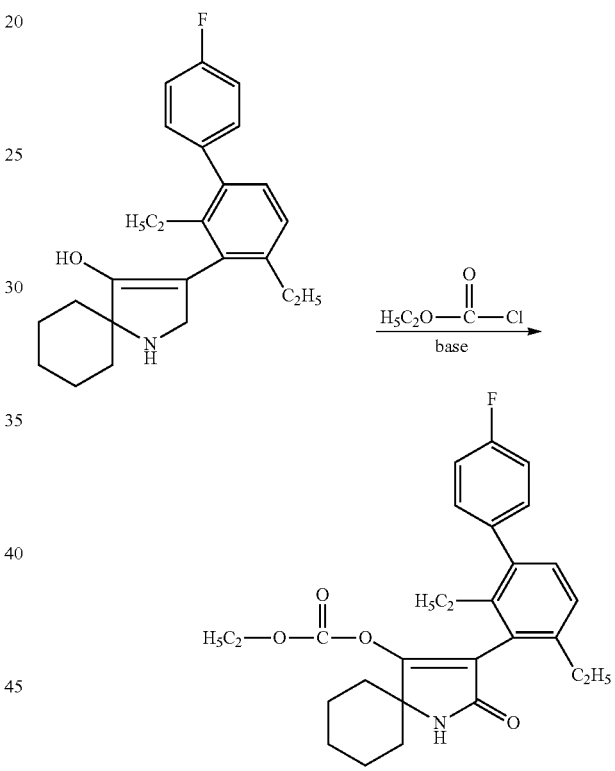

Using, according to process (F), 3-[2-chloro-6-methyl-5-(4-fluorophenyl)phenyl]-4-hydroxy-1-oxaspiro[4.4]non-3-en-2-one and methyl chloromonothioformate as starting materials, the course of the reaction can be represented as follows:

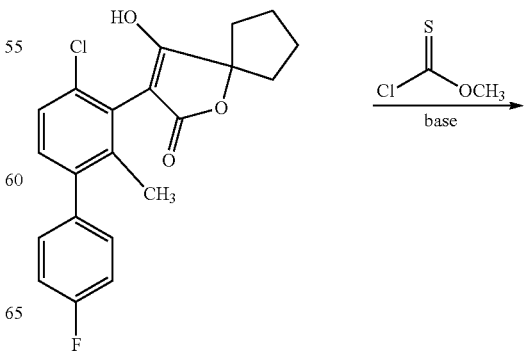

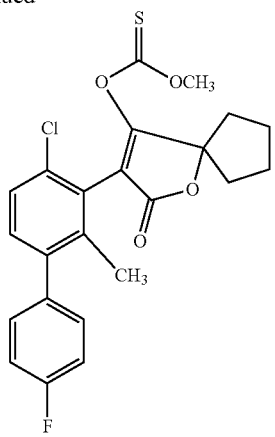

Using, according to process (G), 2-[(6-ethyl-2,4-dimethyl-3-(4-fluorophenyl))phenyl]-4-hydroxy-1-azaspiro[5.4]dec-3-en-2-one and methanesulphonic chloride as starting materials, the course of the reaction can be represented by the reaction scheme below:

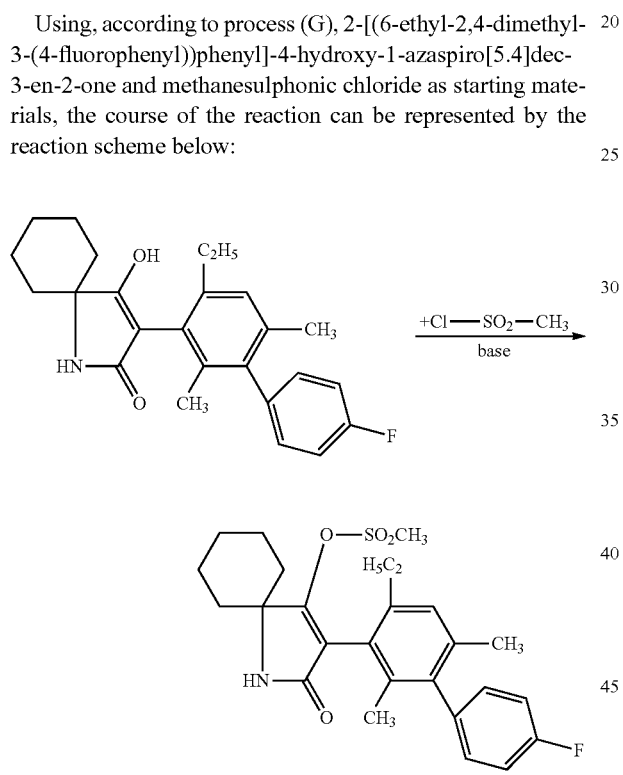

Using, according to process (H), 3-[6-ethyl-2-methyl-3-(4-fluorophenyl)phenyl]-4-hydroxy-1-oxaspiro[4.4]non-3-en-2-one and 2,2,2-trifluoroethyl methanethiophosphonic chloride as starting materials, the course of the reaction can be represented by the reaction scheme below:

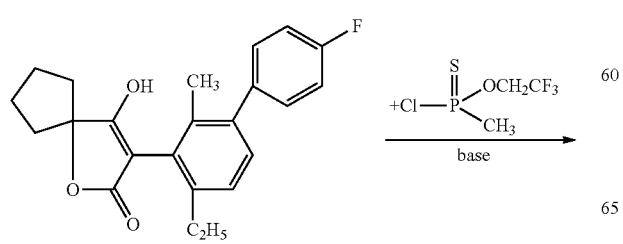

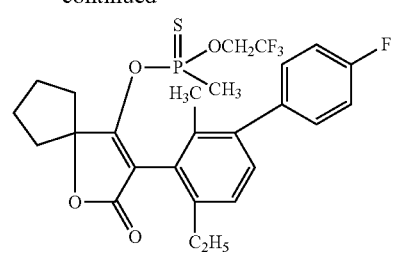

Using, according to process (I), 3-[2,6-diethyl-3-(3,4-difluorophenyl)-phenyl]-4-hydroxy-1-azaspiro[5.4]dec-3-en-2-one and NaOH as components, the course of the process according to the invention can be represented by the reaction scheme below:

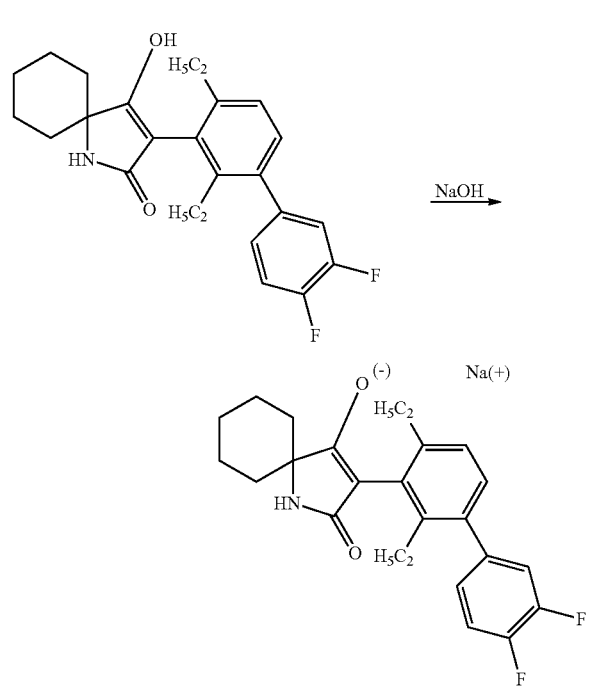

Using, according to process (J) (variant α), 3-[6-ethyl-2-methyl-3-(4-fluorophenyl)phenyl]-4-hydroxy-1-oxaspiro[4.4]non-3-en-2-one and ethyl isocyanate as starting materials, the course of the reaction can be represented by the reaction scheme below:

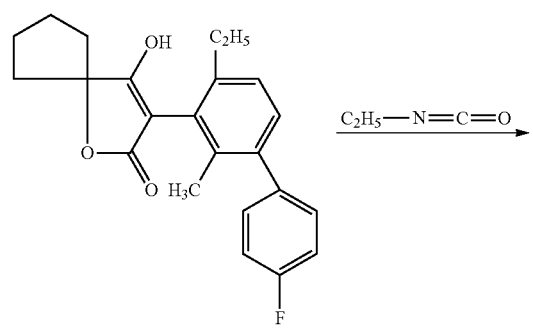

-continued

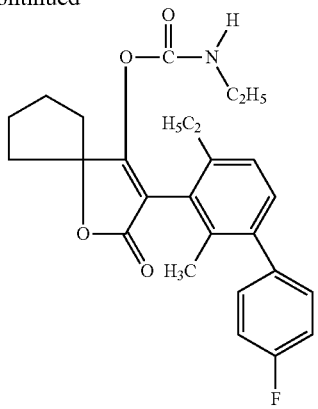

Using, according to process (J) (variant β), 3-[2-chloro-6-methyl-5-(4-fluorophenyl)phenyl]-4-hydroxy-1-azaspiro[5.4]dec-3-en-2-one and dimethylcarbamoyl chloride as starting materials, the course of the reaction can be represented by the scheme below:

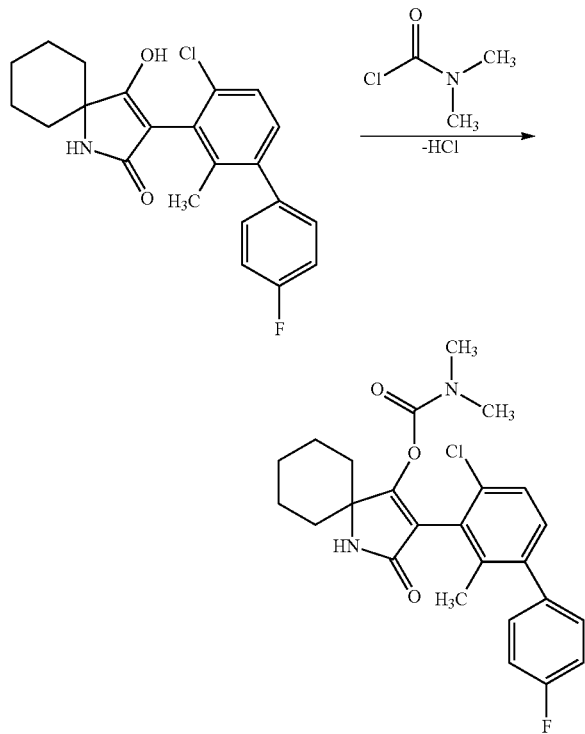

The compounds, required as starting materials in the process (A) according to the invention, of the formula (II)

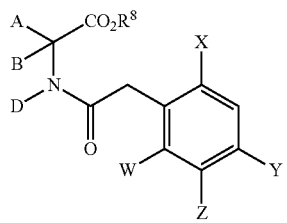

(II)

in which
A, B, D, W, X, Y, Z and $R^8$ have the meanings given above are novel.

The acylamino acid esters of the formula (II) are obtained, for example, when amino acid derivatives of the formula (XV)

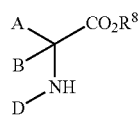

(XV)

in which
A, B, D and $R^8$ have the meanings given above
are acylated with substituted phenyl acetic acid derivatives of the formula (XVI)

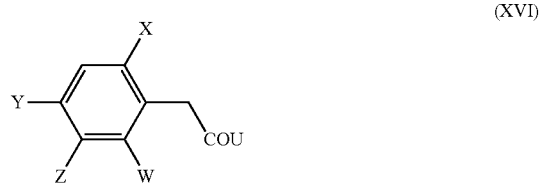

(XVI)

in which
W, X, Y and Z have the meanings given above and
U represents a leaving group introduced by reagents for activating carboxylic acids, such as carbonyldiimidazole, carbonyldiimides (such as, for example, dicyclohexylcarbodiimide), phosphorylating reagents (such as, for example, $POCl_3$, BOP—Cl), halogenating agents, such as, for example, thionyl chloride, oxalyl chloride, phosgene or chloroformic esters
(Chem. Reviews 52, 237-416 (1953); Bhattacharya, Indian J. Chem. 6, 341-5, 1968)
or when acylamino acids of the formula (XVII)

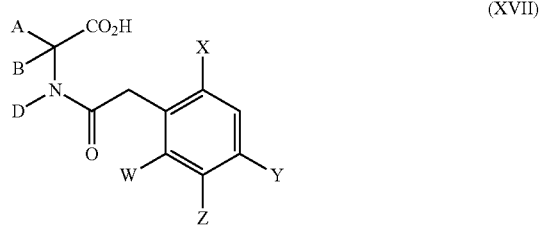

(XVII)

in which
A, B, D, W, X, Y and Z have the meanings given above are esterified (Chem. Ind. (London) 1568 (1968)).
The compounds of the formula (XVII)

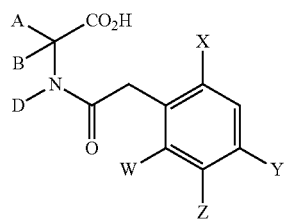

(XVII)

in which
A, B, D, W, X, Y and Z have the meanings given above are novel.

The compounds of the formula (XVII) are obtained when amino acids of the formula (XVIII)

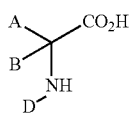

(XVIII)

in which
A, B and D have the meanings given above
are acylated with substituted phenylacetyl halides of the formula (XVI)

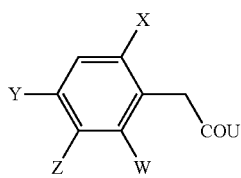

(XVI)

in which
U, W, X, Y and Z have the meanings given above,
for example according to Schotten-Baumann (Organikum, VEB Deutscher Verlag der Wissen-schaften, Berlin 1977, p. 505).

The compounds of the formula (XVI) are novel. They can be prepared by processes known in principle (see, for example, H. Henecka, Houben-Weyl, Methoden der Organischen Chemie [Methods of Organic Chemistry], Vol. 8, pp. 467-469 (1952), or according to the patent applications cited at the outset).

The compounds of the formula (XVI) are obtained, for example, when substituted phenylacetic acids of the formula (XIX)

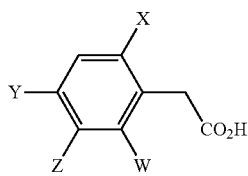

(XIX)

in which
W, X, Y and Z have the meanings given above
are reacted with halogenating agents (for example thionyl chloride, thionyl bromide, oxalyl chloride, phosgene, phosphorus trichloride, phosphorus tribromide or phosphorus pentachloride) or phosphorylating agents (for example $POCl_3$, BOP—Cl), if appropriate in the presence of a diluent (for example optionally chlorinated aliphatic or aromatic hydrocarbons, such as toluene or methylene chloride), at temperatures of from $-20°$ C. to $150°$ C., preferably from $-10°$ C. to $100°$ C.

Some of the compounds of the formulae (XV) and (XVIII) are known from the patent applications cited at the outset, and/or they can be prepared by known processes (see, for example, Compagnon, Miocque Ann. Chim. (Paris) [14] 5, pp. 11-22, 23-27 (1970)).

The substituted cyclic aminocarboxylic acids of the formula (XVIIIa) in which A and B form a ring can generally be obtained by the Bucherer-Bergs synthesis or by the Strecker synthesis, where they are in each case obtained in different isomeric forms. Thus, the conditions of the Bucherer-Bergs synthesis yield predominantly the isomers (hereinbelow, for the sake of simplicity, referred to as β) in which the radicals R and the carboxyl group are in equatorial positions, whereas the conditions of the Strecker synthesis yield predominantly the isomers (hereinbelow, for the sake of simplicity, referred to as α) in which the amino group and the radicals R are in equatorial positions.

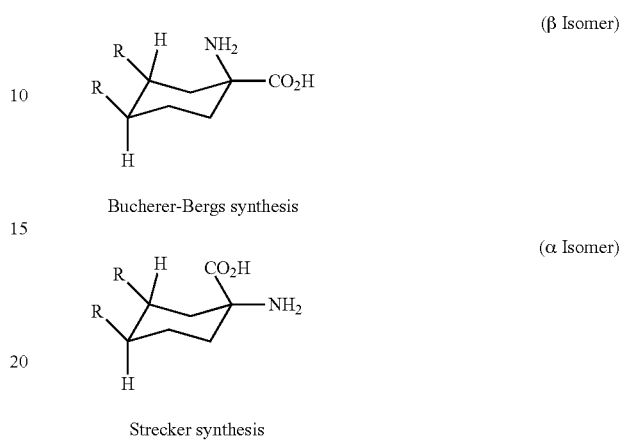

(β Isomer)

Bucherer-Bergs synthesis (α Isomer)

Strecker synthesis (L. Munday, J. Chem. Soc. 4372 (1961); J. T. Eward, C. Jitrangeri, Can. J. Chem. 53, 3339 (1975).

Furthermore, the starting materials, employed in the above process (A), of the formula (II)

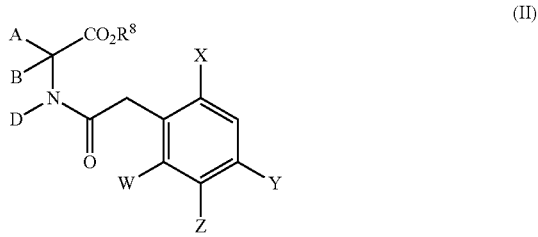

(II)

in which
A, B, D, W, X, Y, Z and $R^8$ have the meanings given above
can be prepared by reacting aminonitriles of the formula (XX)

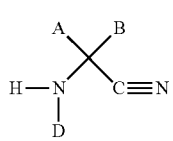

(XX)

in which
A, B and D have the meanings given above
with substituted phenylacetyl halides of the formula (XVI)

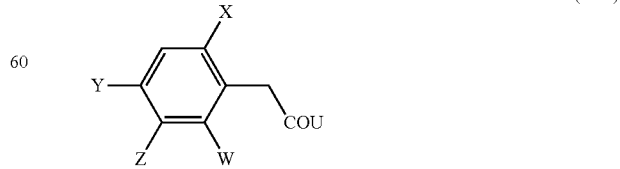

(XVI)

in which
W, X, Y and Z have the meanings given above to give compounds of the formula (XXI)

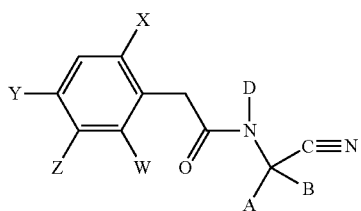
(XXI)

in which
A, B, D, W, X, Y and Z have the meanings given above,
and then subjecting these to an acidic alcoholysis (EP-A-595130).

The compounds of the formula (XXI) are likewise novel.

The compounds of the formula (XX) are known from the patent applications cited at the outset and/or can be prepared by the methods given therein.

The compounds, required as starting materials in the process (B) according to the invention, of the formula (III)

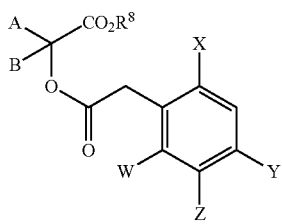
(III)

in which
A, B, W, X, Y, Z and $R^8$ have the meanings given above
are novel.

They can be prepared from methods known in principle.

Thus, the compounds of the formula (III) are obtained, for example, when 2-hydroxycarboxylic esters of the formula (XXII)

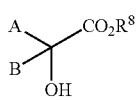
(XXII)

in which
A, B and $R^8$ have the meanings given above
are acylated with substituted phenylacetyl halides of the formula (XVI)

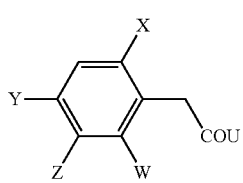
(XVI)

in which
W, X, Y and U have the meanings given above
Chem. Reviews 52, 237-416 (1953) and the applications cited at the outset).

The compounds of the formula (XXII) are likewise known from the applications cited at the outset.

The compounds of the formula (XIX) are novel.

For example, the compounds of the formula (XIX),

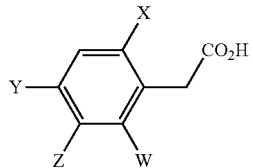
(XIX)

in which
W, X, Y and Z have the meanings given above
are obtained
α) when compounds of the formula (XIX-a)

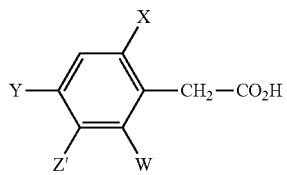
(XIX-a)

in which
X and Y have the meaning given above,
Z' represents chlorine, bromine or iodine, preferably bromine,
are reacted with boronic acids or boronic acid derivatives of the formula (IV)

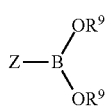
(IV)

in which
Z and $R^9$ have the meaning given above
in the presence of a solvent, a base and a catalyst (preferably a palladium salt or palladium complex, such as, for example, palladiumtetrakis(triphenylphosphine)) or
β) when phenylacetic esters of the formula (XXIII)

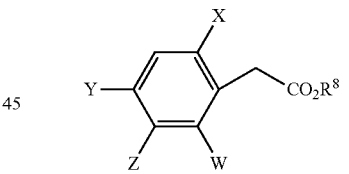
(XXIII)

in which
W, X, Y, Z and $R^8$ have the meaning given above
are hydrolysed in the presence of acids or bases, in the presence of a solvent under generally known standard conditions
or
γ) when phenylacetic acids of the formula (XIX-b)

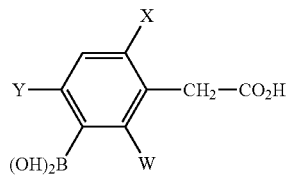
(XIX-b)

in which
W, X and Z have the meaning given above
are reacted with halogen compounds of the formula (XXIV), Z-Hal (XXIV)

in which
Z has the meaning given above
Hal represents chlorine, bromine or iodine, preferably bromine or iodine,
in the presence of a solvent, a base and a catalyst (preferably a palladium salt or one of the palladium complexes mentioned above).

Some of the compounds of the formulae (IV) and (XXIV) are known, some are commercially available, or they can be prepared by processes known in principle. Some of the phenylacetic acids of the formula (XIX-a) are novel, and they can be prepared in principle by the processes described in WO 97/01 535, WO 97/36 868 and WO 98/05 638. Some of the compounds of the formula (XIX-b) are known from WO 05/016873, or they can be prepared by the processes described therein.

The compounds of the formula (XXIII) are novel.
The compounds of the formula (XXIII)

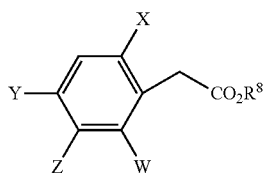

(XXIII)

in which
W, X, Y, Z and $R^8$ have the meaning given above
are obtained, for example,
when phenylacetic esters of the formula (XXIII-a)

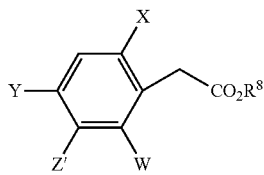

(XXIII-a)

in which
$R^8$, W, X, Y and Z' have the meaning given above
are reacted with boronic acids or boronic acid derivatives of the formula (IV)

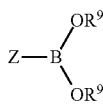

(IV)

in which
Z and $R^9$ have the meaning given above
in the presence of a solvent, a base and a catalyst (preferably a palladium salt or one of the palladium complexes mentioned above).

Some of the phenylacetic esters of the formula (XXIII-a) are novel, and they can be prepared in principle by the processes described in the applications WO 97/01535, WO 97/36868 and WO 98/05638.

Some of the compounds required as starting materials in the above process (C), of the formulae (I-1'-a) to (I-2'-g), in which A, B, D, W, X and Y have the meaning given above and Z' represents chlorine, bromine or iodine, preferably bromine, are novel and some are known, or they can be prepared according to the processes described at the outset.

The acid halides of the formula (V), carboxylic anhydrides of the formula (VI), chloroformic esters or chloroformic thioesters of the formula (VII), chloromonothioformic esters or chlorodithioformic esters of the formula (VIII), sulphonyl chlorides of the formula (IX), phosphorus compounds of the formula (X) and metal hydroxides, metal alkoxides or amines of the formulae (XI) and (XII) and isocyanates of the formula (XIII) and carbamoyl chlorides of the formula (XIV) furthermore required as starting materials for carrying out the processes (D), (E), (F), (G), (H), (I) and (J) according to the invention are generally known compounds of organic or inorganic chemistry.

The process (A) is characterized in that compounds of the formula (II) in which A, B, D, W, X, Y, Z and $R^8$ have the meanings given above are subjected to an intramolecular condensation in the presence of a base.

Suitable diluents for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures may be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in about doubly equimolar amounts. However, it is also possible to use a relatively large excess (up to 3 mol) of one component or the other.

The process (B) is characterized in that compounds of the formula (III) in which A, B, W, X, Y, Z and $R^8$ have the meanings given above are subjected to an intramolecular condensation in the presence of a diluent and in the presence of a base.

Suitable diluents which can be used for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperatures may be varied within a relatively wide range. In general, the process is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in about equimolar amounts. However, it is also possible to use a relatively large excess (up to 3 mol) of one component or the other.

Suitable catalysts for carrying out the process (C) according to the invention are palladium(0) complexes. Preference is given, for example, to tetrakis(triphenylphosphine)palladium. If appropriate, it is also possible to use palladium(II) salts, for example $PdCl_2$, $Pd(NO_3)_2$.

Suitable acid acceptors for carrying out the process (C) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, cesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (C) according to the invention are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature in the process (C) according to the invention can be varied within a relatively wide range. In general, the process is carried out at temperatures between 0° C. and +140° C., preferably between 50° C. and +100° C.

When carrying out the process (C) according to the invention, the boronic acid derivatives of the formula (IV) in which Z has the meaning given above and the compounds of the formulae (I-1'-a) to (I-2'-g) in which A, B, D, W, X, Y and Z' have the meaning given above are employed in a molar ratio of from 1:1 to 3:1, preferably from 1:1 to 2:1. In general, from 0.005 to 0.5 mol, preferably from 0.01 mol to 0.1 mol, of catalyst are employed per mole of the compounds of the formulae (I-1'-a) to (I-2'-g). The base is generally employed in excess.

The process (D-α) is characterized in that compounds of the formulae (I-1-a) to (I-2-a) are reacted with carbonyl halides of the formula (V), if appropriate in the presence of a diluent and if appropriate in the presence of an acid binder.

Suitable diluents for use in the process (D-α) according to the invention are all solvents inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. If the acid halide is sufficiently stable to hydrolysis, the reaction can also be carried out in the presence of water.

Suitable acid binders for the reaction according to the process (D-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (D-α) according to the invention can be varied within a relatively wide range. In general, the process is carried out at temperatures between −20° C. and +150° C., preferably between 0° C. and 100° C.

When carrying out the process (D-α) according to the invention, the starting materials of the formulae (I-1-a) to (I-2-a) and the carbonyl halide of the formula (V) are generally each employed in approximately equivalent amounts. However, it is also possible to use a relatively large excess (up to 5 mol) of the carbonyl halide. Work-up is carried out by customary methods.

The process (D-β) is characterized in that compounds of the formulae (I-1-a) to (I-2-a) are reacted with carboxylic anhydrides of the formula (VI), if appropriate in the presence of a diluent and if appropriate in the presence of an acid binder.

Suitable diluents for use in the process (D-β) according to the invention are, preferably, the diluents which are also preferred when using acid halides. Besides, excess carboxylic anhydride may also simultaneously act as diluent.

Suitable acid binders, which are added, if appropriate, for process (D-β) are, preferably, the acid binders which are also preferred when using acid halides.

The reaction temperatures in the process (D-β) according to the invention may be varied within a relatively wide range. In general, the process is carried out at temperatures between −20° C. and +150° C., preferably between 0° C. and 100° C.

When carrying out the process (D-β) according to the invention, the starting materials of the formulae (I-1-a) to (I-2-a) and the carboxylic anhydride of the formula (VI) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (E) is characterized in that compounds of the formulae (I-1-a) to (I-2-a) are in each case reacted with chloroformic esters or chloroformic thioesters of the formula (VII), if appropriate in the presence of a diluent and if appropriate in the presence of an acid binder.

Suitable acid binders for the reaction according to the process (E) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (E) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (E) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (E) according to the invention is generally carried out under atmospheric pressure.

When carrying out the process (E) according to the invention, the starting materials of the formulae (I-1-a) to (I-2-a) and the appropriate chloroformic ester or chloroformic thioester of the formula (VII) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (F) according to the invention is characterized in that compounds of the formulae (I-1-a) to (I-2-a) are in each case reacted with compounds of the formula (VIII) in the presence of a diluent and, if appropriate, in the presence of an acid binder.

In preparation process (F), about 1 mol of chloromonothioformic ester or chlorodithioformic ester of the formula (VIII) is reacted per mole of the starting material of the formulae (I-1-a) to (I-2-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-1-a) to (I-2-a) is prepared by addition of strong deprotonating agents, such as, for example, sodium hydride or potassium tert-butoxide, the further addition of acid binders may be dispensed with.

If acid binders are used, these are customary inorganic or organic bases; sodium hydroxide, sodium carbonate, potassium carbonate, pyridine and triethylamine may be mentioned by way of example.

The reaction may be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are in each case reacted with sulphonyl chlorides of the formula (IX), if appropriate in the presence of a diluent and if appropriate in the presence of an acid binder.

In preparation process (G), about 1 mol of sulphonyl chloride of the formula (IX) is reacted per mole of the starting material of the formulae (I-1-a) to (I-2-a) at from −20 to 150° C., preferably from 20 to 70° C.

Suitable diluents which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-2-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be carried out at atmospheric pressure or under elevated pressure and is preferably carried out at atmospheric pressure. Work-up is carried out by customary methods.

The process (H) according to the invention is characterized in that compounds of the formulae (I-1-a) to (I-2-a) are in each case reacted with phosphorus compounds of the formula (X), if appropriate in the presence of a diluent and if appropriate in the presence of an acid binder.

In preparation process (H), to obtain compounds of the formulae (I-1-e) to (I-2-e), from 1 to 2, preferably from 1 to 1.3, mol of the phosphorus compound of the formula (X) are reacted per mole of the compounds (I-1-a) to (I-2-a), at temperatures between −40° C. and 150° C., preferably between −10 and 110° C.

Suitable diluents which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethyl-formamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The resulting end products are preferably purified by crystallization, chromatographic purification or "incipient distillation", i.e. removal of the volatile components under reduced pressure.

The process (I) is characterized in that compounds of the formulae (I-1-a) to (I-2-a) are reacted with metal hydroxides or metal alkoxides of the formula (XI) or amines of the formula (XII), if appropriate in the presence of a diluent.

Suitable diluents for use in the process (I) according to the invention are, preferably, ethers, such as tetrahydrofuran, dioxane, diethyl ether, or else alcohols, such as methanol, ethanol, isopropanol, and also water.

The process (I) according to the invention is generally carried out under atmospheric pressure.

The reaction temperatures are generally between −20° C. and 100° C., preferably between 0° C. and 50° C.

The process (J) according to the invention is characterized in that compounds of the formulae (I-1-a) to (I-2-a) are in each case reacted with (J-α) compounds of the formula (XIII), if appropriate in the presence of a diluent and if appropriate in the presence of a catalyst, or (J-β) with compounds of the formula (XIV), if appropriate in the presence of a diluent and if appropriate in the presence of an acid binder.

In preparation process (J-α), about 1 mol of isocyanate of the formula (XIII) is reacted per mole of starting material of the formulae (I-1-a) to (I-2-a), at from 0 to 100° C., preferably from 20 to 50° C.

Suitable diluents which are added, if appropriate, are all inert organic solvents, such as ethers, amides, nitriles, sulphones or sulphoxides.

If appropriate, catalysts may be added to accelerate the reaction. Suitable for use as catalysts are, very advantageously, organotin compounds, such as, for example, dibutyltin dilaurate. The reaction is preferably carried out at atmospheric pressure.

In preparation process (J-β), about 1 mol of carbamoyl chloride of the formula (XIV) is reacted per mole of starting compound of the formulae (I-1-a) to (I-2-a), at from −20 to 150° C., preferably at from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-2-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp.,

*Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control Protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Athalia* spp., *Diprion* spp., *Hoplocampa* spp., *Lasius* spp., *Monomorium pharaonic*, *Vespa* spp.

From the order of the Isopoda, for example, *Armadillidium vulgare*, *Oniscus asellus* and *Porcellio scaber*.

From the order of the Isoptera, for example, *Acromyrmex* spp., *Atta* spp., *Cornitermes cumulans*, *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp. *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta americana*, *Schistocerca gregaria*.

From the order of the *Siphonaptera*, for example, *Ceratophyllus* spp. and *Xenopsylla cheopis*.

From the order of the Symphyla, for example, *Scutigerella* spp.

From the order of the Thysanoptera, for example, *Anaphothrips obscurus, Baliothrips Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

The compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). They can also be used as intermediates or precursors for the synthesis of other active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers. The formulations are prepared either in suitable facilities or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic, organic or inorganic substance which may be solid or liquid and with which the active compounds are mixed or bonded for better applicability, in particular for application to plants or plant parts. The solid or liquid carrier is generally inert and should be suitable for use in agriculture.

Suitable solid carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colourants such as inorganic pigments, for example iron oxide, titanium oxide and Prussian Blue, and organic colourants such as alizarin colourants, azo colourants and metal phthalocyanine colourants, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compounds according to the invention may be used as they are or in their formulations, including a mixture with one or more suitable fungicides, bactericides, acaricides, nematicides, insecticides, microbicides, fertilizers, attractants, sterilants, synergists, safeners, semiochemicals and/or plant growth regulators, in order thereby, for example, to broaden the activity spectrum, to prolong the duration of action, to increase the rate of action, to prevent repulsion or to prevent development of resistance. Furthermore, active compound combinations of this kind may improve plant growth, raise tolerance towards high or low temperatures, against drought or against increased levels of water and/or soil salt. It is also possible to improve the flowering and fruiting performance, to facilitate harvesting and increase yields, to accelerate ripening, to increase the quality and/or nutritional value of the harvested products, to prolong storage life and/or to improve the manageability of the harvested products. Combining the active compounds of the invention and co-components produces synergistic effects—that is, the activity of the mixture in question is greater than was to be expected based on the activity of the individual components. In general it is possible to use the combinations not only in premixes, tank-mixes or ready-made mixes but also in seed applications.

Each additional active compound may be mixed with the active compounds according to the invention in a wide range, preferably in a ratio of from 100:1 to 1:100, particularly preferably from 5:1 to 1:5.

Particularly favourable co-components are, for example, those listed below.

Insecticides/Acaricides/Nematicides:

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example
carbamates, for example alanycarb, aldicarb, bendiocarb, benfuracarb, butocarboxim, butoxy-carboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example
organochlorines, for example chlordane and endosulfan (alpha-); or
fiproles (phenylpyrazoles), for example ethiprole, fipronil, pyrafluprole and pyriprole.

(3) Sodium channel modulators/voltage-dependent sodium channel blockers, for example
pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or
DDT; or methoxychlor.

(4) Nicotinergic acetylcholine receptor agonists, for example
neonicotinoids, for example acetamiprid, clothianidin, dinotefuran, imidacloprid, nitenpyram, thiacloprid, thiamethoxam; or
nicotine.

(5) Allosteric acetylcholine receptor modulators (agonists), for example
spinosyns, for example spinetoram and spinosad.

(6) Chloride channel activators, for example
avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active compounds with unknown or non-specific mechanisms of action, for example
fumigants, for example methyl bromide and other alkyl halides; or
chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or
organotin compounds, for example azocyclotin, cyhexatin, fenbutatin oxide; or
propargite; tetradifon.

(13) Oxidative phoshorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example
diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or
rotenone (Derris).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(28) Ryanodine receptor effectors, for example diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

Further active compounds with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, fluopyram, pyridalyl and pyrifluquinazon; and also products based on *Bacillus firmus* (I-1582, BioNeem, Votivo) and also the known active compounds below:

4-{[(6-bromopyrid-3-yl)methyl](2-fluoroethyl)
  amino}furan-2(5H)-one (known from WO 2007/115644),
4-{[(6-fluoropyrid-3-yl)methyl](2,2-difluoroethyl)
  amino}furan-2(5H)-one (known from WO 2007/115644),
4-{[(2-chloro-1,3-thiazol-5-yl)methyl](2-fluoroethyl)
  amino}furan-2(5H)-one (known from WO 2007/115644),
4-{[(6-chloropyrid-3-yl)methyl](2-fluoroethyl)
  amino}furan-2(5H)-one (known from WO 2007/115644),
4-{[(6-chloropyrid-3-yl)methyl](2,2-difluorethyl)
  amino}furan-2(5H)-one (known from WO 2007/115644),
4-{[(6-chloro-5-fluoropyrid-3-yl)methyl] (methyl)
  amino}furan-2(5H)-one (known from WO 2007/115643),
4-{[(5,6-dichloropyrid-3-yl)methyl](2-fluoroethyl)
  amino}furan-2(5H)-one (known from WO 2007/115646),
4-{[(6-chloro-5-fluoropyrid-3-yl)methyl](cyclopropyl)
  amino}furan-2(5H)-one (known from WO 2007/115643),
4-{[(6-chloropyrid-3-yl)methyl](cyclopropyl)
  amino}furan-2(5H)-one (known from EP-A-0 539 588),
4-{[(6-chloropyrid-3-yl)methyl](methyl)amino}furan-2(5H)-one (known from EP-A-0 539 588), [(6-chloropyridin-3-yl)methyl](methyl)oxido-λ⁴-sulphanylidenecyanamide (known from WO 2007/149134), [1-(6-chloropyridin-3-yl)ethyl](methyl)oxido-λ⁴-sulphanylidenecyanamide (known from WO 2007/149134) and its diastereomers (A) and (B)

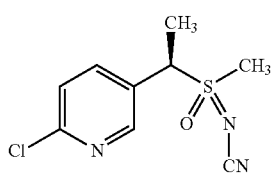

(A)

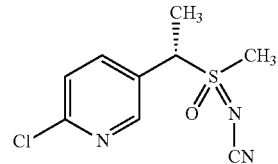

(B)

(also known from WO 2007/149134), [(6-trifluoromethylpyridin-3-yl)methyl](methyl)oxido-λ⁴-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2006/129714), 2-cyano-3-(difluoromethoxy)-N,N-dimethylbenzenesulphonamide (known from WO 2006/056433), 2-cyano-3-(difluoromethoxy)-N-methylbenzenesulphonamide (known from WO 2006/100288), 2-cyano-3-(difluoromethoxy)-N-ethylbenzenesulphonamide (known from WO 2005/035486), 4-(difluoromethoxy)-N-ethyl-N-methyl-1,2-benzothiazol-3-amine 1,1-dioxide (known from WO 2007/057407) and N-[1-(2,3-dimethylphenyl)-2-(3,5-dimethylphenyl)ethyl]-4,5-dihydro-1,3-thiazol-2-amine (known from WO 2008/104503).

In a preferred embodiment of the invention, to boost the activity, a penetrant is additionally added to the crop protection compositions. Suitable penetrants also include, for example, substances which promote the availability of the compounds of the formula (I) in the spray coating. These include, for example, mineral or vegetable oils. Suitable oils are all mineral or vegetable—optionally modified—oils which are usually used in agrochemical compositions. Mention may be made, by way of example of, sunflower oil, rapeseed oil, olive oil, castor oil, colza oil, maize seed oil, cotton seed oil and soya bean oil, or the esters of said oils. Preference is given to rapeseed oil, sunflower oil and their methyl and ethyl esters, in particular to rapeseed oil methyl esters.

The concentration of penetrant in the compositions according to the invention can be varied within a wide range. In the case of a formulated crop protection composition it is generally from 1 to 95% by weight, preferably from 1 to 55% by weight, particularly preferably 15-40% by weight. In the ready-to-use compositions (spray liquors), the concentration is generally between 0.1 and 10 g/l, preferably between 0.5 and 5 g/l.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

Application occurs in a customary manner, suitable for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Examples which may be mentioned are the important crop plants, such as cereals (wheat, rice), maize, soya beans, potatoes, sugar beet, tomatoes, peas and other vegetable species, cotton, tobacco, oilseed rape and also fruit plants (with the fruits apples, pears, citrus fruits and grapes). Plant parts are to be understood as meaning all above-ground and below-ground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing them to act on the surroundings, environment or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, biotypes or genotypes.

Depending on the plant species or plant cultivars, their location and growth conditions (soils, climate, vegetation period, nutrition), the treatment according to the invention may also result in superadditive ("synergistic") effects. Thus possible are, for example, reduced application rates and/or a widening of the activity spectrum and/or an increase of the activity of the compounds and compositions usable according to the invention, better plant growth, increased tolerance to high or low temperatures, increased tolerance to drought or to water or soil salt content, increased flowering, easier harvesting, accelerated maturation, higher harvest yields, higher quality and/or higher nutritional value of the harvested products, increased storability and/or processability of the harvested products, which exceed the effects normally to be expected.

The preferred transgenic plants or plant cultivars (i.e. those obtained by genetic engineering) which are to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering, easier harvesting, accelerated maturation, higher harvest yields, higher quality and/or a higher nutritional value of the harvested products, better storability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (with the fruits apples, pears, citrus fruits and grapes), with particular emphasis being given to maize, soya beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance against glyphosate, for example maize, cotton, soya beans), Liberty Link® (tolerance against phosphinothricin, for example oilseed rape), IMI® (tolerance against imidazolinones) and STS® (tolerance against sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants stated can be treated particularly advantageously in accordance with the invention with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., (*Ctenocephalides canis, Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention also have a strong insecticidal action against insects which destroy industrial materials.

The following insects may be mentioned as examples and as preferred—but without a limitation:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus*;

dermapterans, such as *Sirex juvencus, Urocerus gigas, Urocerus gigas taignus, Urocerus augur*; termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootennopsis nevadensis, Coptotermes formosanus*;

bristletails, such as *Lepisma saccharina*.

Industrial materials in the present connection are to be understood as meaning non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

With respect to possible additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Derrnanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the *Dermaptera*, for example, *Forficula auricularia.*

From the order of the *Isoptera*, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The compounds of the formula (I) according to the invention (active compounds) have excellent herbicidal activity against a broad spectrum of economically important monocotyledonous and dicotyledonous annual harmful plants. The active compounds also act efficiently on perennial harmful plants which produce shoots from rhizomes, root stocks or other perennial organs and which are difficult to control.

The amount of active compound used may vary within a relatively wide range. It depends essentially on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably from 0.05 to 20 parts by weight, of one of the crop plant compatibility-improving compounds (antidotes/safeners) mentioned above under (b') are present per part by weight of active compound of the formula (I).

The active compound combinations according to the invention are generally applied in the form of finished formulations. However, the active compounds present in the active compound combinations can, as individual formulations, also be mixed during use, i.e. be applied in the form of tank mixtures.

For certain applications, in particular in the post-emergence method, it may furthermore be advantageous to include in the formulations, as further additives, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. The application is in the customary manner, for example by watering, spraying, atomizing, dusting or broadcasting.

The application rates of the active compound combinations according to the invention can be varied within a certain range; they depend, inter alia, on the weather and on soil factors. In general, the application rates are from 0.001 to 5 kg per ha, preferably from 0.005 to 2 kg per ha, particularly preferably from 0.01 to 0.5 kg per ha.

Depending on their properties, the safeners to be used according to the invention can be used for pretreating the seed of the crop plant (seed dressing) or can be introduced into the seed ferrules prior to the seed or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beet, sugar cane and also fruit plants (with the fruits apples, pears, citrus fruits and grapevines), greater emphasis being given to cereals, maize, soya beans, potatoes, cotton and oilseed rape.

All plants and plant parts can be treated with the active compounds according to the invention. Here, plants are to be understood as meaning all plants and plant populations such as wanted and unwanted wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seed and also roots, tubers and rhizomes. The plant parts also include harvested material, and also vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, broadcasting, painting on or injection and, in the case of propagation material, in particular in the case of seed, also by applying one or more coats.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or unwanted crop plants), to the seed (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated according to the invention in a particularly advantageous manner with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active compounds are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

Owing to their herbicidal and plant-growth-regulatory properties, the active compounds can also be employed for controlling harmful plants in crops of known genetically modified plants or genetically modified plants which are still to be developed. As a rule, the transgenic plants are distinguished by especially advantageous properties, for example by resistances to certain pesticides, mainly certain herbicides, resistances to plant diseases or causative organisms of plant diseases, such as certain insects, nematodes or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known. Further particular properties may be tolerance or resistance to abiotic stresses, for example heat, cold, drought, salt and ultraviolet radiation. The active compounds can also be used in transgenic plants distinguished by higher yields, for example by an improved photosynthesis performance or improved nutrient uptake.

It is preferred to use the compounds of the formula (I) according to the invention or salts thereof in economically important transgenic crops of useful plants and ornamentals, for example of cereals such as wheat, barley, rye, oats, millet, rice, cassava and maize or else crops of sugar beet, cotton, soya bean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP 0221044, EP 0131624). For example, the following have been described in several cases:

recombinant modifications of crop plants for the purposes of modifying the starch synthesized in the plants (for example WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377 A) or of the sulphonylurea type (EP 0257993 A, U.S. Pat. No. 5,013,659), or against combinations or mixtures of these herbicides by "gene stacking", such as transgenic crop plants, for example maize or soya beans, having the trade name or the name Optimum™ GAT™ (Glyphosate ALS Tolerant). Furthermore, transgenic plants resistant to synthetic auxines (for example 2, 4 D) HRAC mode of action Class 0 and aryloxyphenoxy propionate (fops, HRAC, Class A) have been described (DHT, Dow Agroscience Herbicide Tolerance Trait)

transgenic crop plants, for example cotton, which is capable of producing *Bacillus thuringiensis* toxins (Bt toxins), which make the plants resistant to certain pests (EP 0142924 A, EP 0193259 A), transgenic crop plants with a modified fatty acid composition (WO 91/03972 A), Genetically modified plants having novel resistance to insects, for example based on the expression of toxins from *Photorhabdus, Xenorhabdus* Symbions from entomopathogenic nematodes and toxins from spiders, scorpions, ants, parasitic wasps, genetically modified crop plants with novel constituents or secondary materials, for example novel phytoalexins, which bring about an increased disease resistance (EP 0309862 A, EP 0464461 A), genetically modified plants with reduced photorespiration which feature higher yields and higher stress tolerance (EP 0305398 A), transgenic crop plants which produce pharmaceutically or diagnostically important proteins ("molecular pharming"), transgenic crop plants which are distinguished by higher yields or better quality, transgenic crop plants which are distinguished by increased tolerance to abiotic and biotic stress factors, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, 2,4 D, dicamba, or to herbicides which inhibit essential plant enzymes, for example acetyl CoA carboxylases, acetolactate synthases (ALS), EPSP synthases, glutamine synthases (GS) or hydroxyphenylpyruvate dioxygenases (HPPD), or to herbicides from the group of the FOPs, sulphonylureas, glyphosates, glufosinates or benzoylisoxazoles and analogous active compounds, or to any combinations of these active compounds.

It is particularly preferred to employ the compounds according to the invention in transgenic crop plants which are resistant to a combination of glyphosates and glufosinates, glyphosates and sulphonylureas or imidazolinones. It is very particularly preferred to employ the compounds according to the invention in transgenic crop plants, for example maize or soya, with the trade name or the designation Optimum™ GAT™ (Glyphosate ALS Tolerant). In addition, it is particularly preferred to employ the compounds according to the invention in transgenic plants which are resistant to synthetic auxins (e.g. 2,4 D) with "HRAC mode of action Class O" and aryloxy-phenoxy propionate (fops) with "HRAC mode of action Class A" (e.g. DHT, Dow Agroscience Herbicide Tolerance Trait).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N. J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active compounds, such as, for example, insecticides, acaracides, herbicides, fungicides, and also with safeners, fertilizers and/or growth regulators, for example in the form of a finished formulation or as a tank mix.

Combination partners which can be used for the compounds according to the invention in mixture formulations or in the tank mix are, for example, known active compounds which are based on an inhibition of, for example, acetolactate synthase, acetyl-CoA carboxylase, cellulose synthase, enolpyruvylshikimat-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or in "The Pesticide Manual", 13th Edition, The British Crop Protection Council and the Royal Soc. of Chemistry, 2003, and the literature cited therein.

The following active compounds, for example, may be mentioned as known herbicides or plant growth regulators which can be combined with the compounds according to the invention:
acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]-ethanesulphonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolatsodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

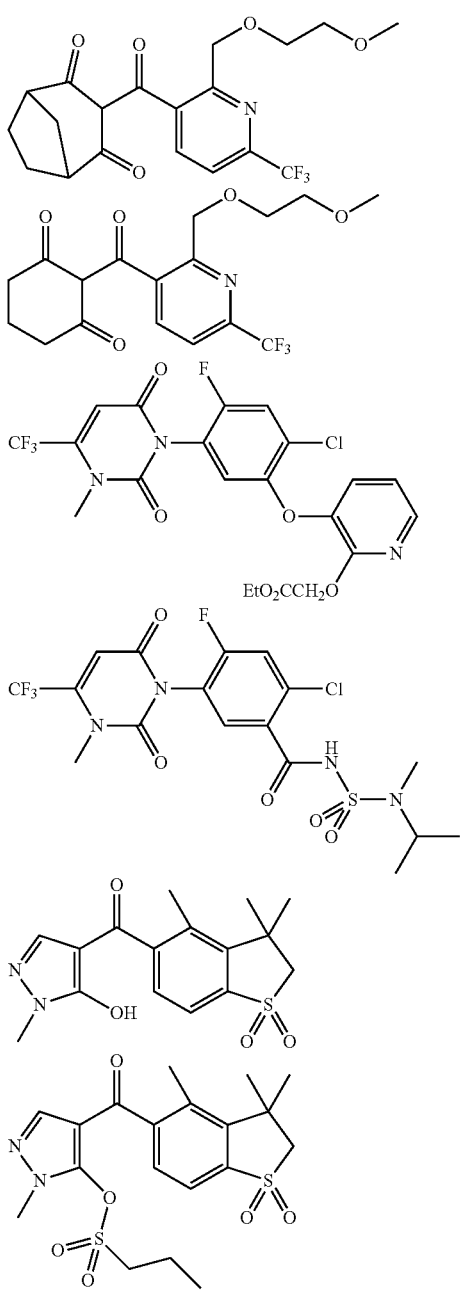

Compounds are designated either with the "common name" in accordance with the International Organization for Standardization (ISO) or with their chemical name or code number and always encompass all of the application forms, such as acids, salts, esters, or modifications, such as isomers, stereoisomers and optical isomers. One or else a plurality of application forms or modifications may be mentioned by way of example.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleylmethyltauride. To prepare the wettable powders, the active herbicidal compounds are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active compound onto adsorptive granulated inert material or by applying active compound concentrates by means of adhesives, for example polyvinyl alcohol, sodium polyacrylate or else mineral oils, onto the surface of carriers such as sand, kaolinites or of granulated inert material. It is also possible to granulate suitable active compounds in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The compounds according to the invention have a potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

diseases caused by powdery mildew pathogens, such as, for example, *Blumeria* species, such as, for example, *Blumeria graminis*;

*Podosphaera* species, such as, for example, *Podosphaera leucotricha*;

*Sphaerotheca* species, such as, for example, *Sphaerotheca fuliginea*;

*Uncinula* species, such as, for example, *Uncinula necator*;

diseases caused by rust disease pathogens, such as, for example, *Gymnosporangium* species, such as, for example, *Gymnosporangium sabinae*

*Hemileia* species, such as, for example, *Hemileia vastatrix*;

*Phakopsora* species, such as, for example, *Phakopsora pachyrhizi* and *Phakopsora meibomiae*;

*Puccinia* species, such as, for example, *Puccinia recondita*;

*Uromyces* species, such as, for example, *Uromyces appendiculatus*;

diseases caused by pathogens from the group of the Oomycetes, such as, for example, *Bremia* species, such as, for example, *Bremia lactucae*;

*Peronospora* species, such as, for example, *Peronospora pisi* or *P. brassicae*;

*Phytophthora* species, such as, for example, *Phytophthora infestans*;

*Plasmopara* species, such as, for example, *Plasmopara viticola*;

*Pseudoperonospora* species, such as, for example, *Pseudoperonospora humuli* or *Pseudoperonospora cubensis*;

*Pythium* species, such as, for example, *Pythium ultimum*;

leaf blotch diseases and leaf wilt diseases caused, for example, by *Alternaria* species, such as, for example, *Alternaria solani*;

*Cercospora* species, such as, for example, *Cercospora beticola*;

*Cladosporium* species, such as, for example, *Cladosporium cucumerinum*;

*Cochliobolus* species, such as, for example, *Cochliobolus sativus*;

(conidia form: *Drechslera*, syn: *Helminthosporium*);

*Colletotrichum* species, such as, for example, *Colletotrichum lindemuthanium*;

*Cycloconium* species, such as, for example, Cycloconium oleaginum;

*Diaporthe* species, such as, for example, *Diaporthe* citri;

*Elsinoe* species, such as, for example, *Elsinoe fawcettii*;

Gloeosporium species, such as, for example, *Gloeosporium laeticolor*;

*Glomerella* species, such as, for example, *Glomerella cingulata*;

*Guignardia* species, such as, for example, *Guignardia bidwelli*;

*Leptosphaeria* species, such as, for example, *Leptosphaeria maculans*;

*Magnaporthe* species, such as, for example, *Magnaporthe grisea*;

*Mycosphaerella* species, such as, for example, *Mycosphaerella graminicola* and *Mycosphaerella fijiensis*;

*Phaeosphaeria* species, such as, for example, *Phaeosphaeria nodorum*;

*Pyrenophora* species, such as, for example, *Pyrenophora teres*;

*Ramularia* species, such as, for example, *Ramularia collocygni*;

*Rhynchosporium* species, such as, for example, *Rhynchosporium secalis*;

*Septoria* species, such as, for example, *Septoria apii*;

*Typhula* species, such as, for example, *Typhula incarnata*;

*Venturia* species, such as, for example, *Venturia inaequalis*;

root and stem diseases caused, for example, by *Corticium* species, such as, for example, *Corticium graminearum*;

*Fusarium* species, such as, for example, *Fusarium oxysporum*;

*Gaeumannomyces* species, such as, for example, *Gaeumannomyces graminis*;

*Rhizoctonia* species, such as, for example, *Rhizoctonia solani*;

*Tapesia* species, such as, for example, *Tapesia acuformis*;

*Thielaviopsis* species, such as, for example, *Thielaviopsis basicola*;

ear and panicle diseases (including maize cobs) caused, for example, by *Alternaria* species, such as, for example, *Alternaria* spp.;

*Aspergillus* species, such as, for example, *Aspergillus flavus*;

*Cladosporium* species, such as, for example, *Cladosporium cladosporioides*;

*Claviceps* species, such as, for example, *Claviceps purpurea*;

*Fusarium* species, such as, for example, *Fusarium culmorum*;

*Gibberella* species, such as, for example, *Gibberella zeae*;

*Monographella* species, such as, for example, *Monographella nivalis*;

diseases caused by smut fungi, such as, for example, *Sphacelotheca* species, such as, for example, *Sphacelotheca reiliana*;

*Tilletia* species, such as, for example, *Tilletia caries*;

*Urocystis* species, such as, for example, *Urocystis occulta*;

*Ustilago* species, such as, for example, *Ustilago nuda*;

fruit rot caused, for example, by *Aspergillus* species, such as, for example, *Aspergillus flavus*;

*Botrytis* species, such as, for example, *Botrytis cinerea*;

*Penicillium* species, such as, for example, *Penicillium expansum* and *Penicillium purpurogenum;*
*Sclerotinia* species, such as, for example, *Sclerotinia sclerotiorum;*
*Verticilium* species, such as, for example, *Verticilium alboatrum;*
seed- and soil-borne rot and wilt diseases, and also diseases of seedlings, caused, for example, by *Alternaria* species, such as, for example, *Alternaria brassicicola;*
*Aphanomyces* species, such as, for example, *Aphanomyces euteiches;*
*Ascochyta* species, such as, for example, *Ascochyta lentis;*
*Aspergillus* species, such as, for example, *Aspergillus flavus;*
*Cladosporium* species, such as, for example, *Cladosporium herbarum;*
*Cochliobolus* species, such as, for example, *Cochliobolus sativus;*
(conidia form: *Drechslera, Bipolaris* Syn: *Helminthosporium*);
*Colletotrichum* species, such as, for example, *Colletotrichum coccodes;*
*Fusarium* species, such as, for example, *Fusarium culmorum;*
*Gibberella* species, such as, for example, *Gibberella zeae;*
*Macrophomina* species, such as, for example, *Macrophomina phaseolina;*
*Monographella* species, such as, for example, *Monographella nivalis;*
*Penicillium* species, such as, for example, *Penicillium expansum;*
*Phoma* species, such as, for example, *Phoma lingam;*
*Phomopsis* species, such as, for example, *Phomopsis sojae;*
*Phytophthora* species, such as, for example, *Phytophthora cactorum;*
*Pyrenophora* species, such as, for example, *Pyrenophora graminea;*
*Pyricularia* species, such as, for example, *Pyricularia oryzae;*
*Pythium* species, such as, for example, *Pythium ultimum;*
*Rhizoctonia* species, such as, for example, *Rhizoctonia solani;*
*Rhizopus* species, such as, for example, *Rhizopus oryzae*
*Sclerotium* species, such as, for example, *Sclerotium rolfsii;*
*Septoria* species, such as, for example, *Septoria nodorum;*
*Typhula* species, such as, for example, *Typhula incarnata;*
*Verticillium* species, such as, for example, *Verticillium dahliae*
cancerous diseases, galls and witches' broom caused, for example, by *Nectria* species, such as, for example, *Nectria galligena;*
wilt diseases caused, for example, by *Monilinia* species, such as, for example, *Monilinia laxa;*
deformations of leaves, flowers and fruits caused, for example, by *Taphrina* species, such as, for example, *Taphrina deformans;*
degenerative diseases of woody plants caused, for example, by *Esca* species, such as, for example, *Phaeomoniella chlamydospora* and *Phaeoacremonium aleophilum* and *Fomitiporia mediterranea;*
diseases of flowers and seeds caused, for example, by *Botrytis* species, such as, for example, *Botrytis cinerea;*
diseases of plant tubers caused, for example, by *Rhizoctonia* species, such as, for example, *Rhizoctonia solani;*
*Helminthosporium* species, such as, for example, *Helminthosporium solani;*
diseases caused by bacterial pathogens, such as, for example, *Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora;*
Preference is given to controlling the following diseases of soya beans:
fungal diseases on leaves, stems, pods and seeds caused, for example, by alternaria leaf spot (*Alternaria* spec. atrans tenuissima), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*).
Fungal diseases on roots and the stem base caused, for example, by
black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

In the present case, undesired microorganisms are to be understood as meaning phytopathogenic fungi, bacteria and viruses. Accordingly, the substances according to the invention can be used to protect plants for a certain period after the treatment against attack by the pathogens mentioned. The period within which protection is brought about generally extends from 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed particularly successfully for controlling cereal diseases such as, for example, against *Puccinia* species and diseases in viticulture and fruit and vegetable growing such as, for example, against *Botrytis, Venturia* or *Alternaria* species.

The active compounds according to the invention are also suitable for increasing the yield of crops. In addition, they show reduced toxicity and are well tolerated by plants.

In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
*Alternaria*, such as *Alternaria tenuis,*
*Aspergillus*, such as *Aspergillus niger,*
*Chaetomium*, such as *Chaetomium globosum,*
*Coniophora*, such as *Coniophora puetana,*
*Lentinus*, such as *Lentinus tigrinus,*
*Penicillium*, such as *Penicillium glaucum,*
*Polyporus*, such as *Polyporus versicolor,*
*Aureobasidium*, such as *Aureobasidium pullulans,*
*Sclerophoma*, such as *Sclerophoma pityophila,*
*Trichoderma*, such as *Trichoderma viride,*
*Escherichia*, such as *Escherichia coli,*
*Pseudomonas*, such as *Pseudomonas aeruginosa*, and
*Staphylococcus*, such as *Staphylococcus aureus.*

The present invention relates to a composition for controlling unwanted microorganisms which comprises at least one of the compounds according to the invention.

To this end, depending on their particular physical and/or chemical properties, the compounds according to the invention can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam-formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. As solid carriers these are suitable: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite, dolomite, and synthetic granules of inorganic and organic meals, and also granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. As dispersants there are suitable: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The formulations described above can be used in a method according to the invention for controlling unwanted microorganisms, where the compounds according to the invention are applied to the microorganisms and/or to their habitat.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after sowing or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular relates to a method for the protection of seed and germinating plants from attack by phytopathogenic fungi, by treating the seed with a composition according to the invention.

The invention also relates to the use of the compositions according to the invention for treating seed for protecting the seed and the germinating plant against phytopathogenic fungi.

Furthermore, the invention relates to seed treated with a composition according to the invention for protection against phytopathogenic fungi.

One of the advantages of the present invention is that the particular systemic properties of the compositions according to the invention mean that treatment of the seed with these compositions not only protects the seed itself, but also the resulting plants after emergence, from phytopathogenic fungi. In this manner, the immediate treatment of the crop at the time of sowing or shortly thereafter can be dispensed with.

It is likewise to be considered advantageous that the mixtures according to the invention can be used in particular also for transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soybeans, rice, potatoes, sunflowers, beans, coffee, beets (for example sugarbeets and fodder beets), peanuts, vegetables (such as tomatoes, cucumbers, onions and lettuce), lawns and ornamental plants. The treatment of the seed of cereals (such as wheat, barley, rye and oats), maize and rice is of particular importance.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds or active compound combinations with customary additives such as, for example, customary extenders and also solvents or diluents, colourants, wetting agents, dispersants, emulsifiers, antifoams, preservatives, secondary thickeners, adhesives, gibberellins and also water.

Colourants which may be present in the seed-dressing formulations which can be used in accordance with the invention are all colourants which are customary for such purposes. In this context, not only pigments, which are sparingly soluble in water, but also dyes, which are soluble in water, may be used. Examples which may be mentioned are the colourants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Preference is given to using cellulose derivatives, acrylic acid derivatives, xanthan, modified clays and finely divided silica.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schällingsbekampfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, either directly or after previously having been diluted with water. Thus, the concentrates or the preparations obtainable therefrom by dilution with water may be used to dress the seed of cereals, such as wheat, barley, rye, oats, and triticale, and also the seed of maize, rice, oilseed rape, peas, beans, cotton, sunflowers, and beets, or else vegetable seed of any of a very wide variety of kinds. The seed-dressing formulations which can be used according to the invention or their dilute preparations may also be used to dress seed of transgenic plants. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The application rate of the seed-dressing formulations which can be used according to the invention may be varied within a relatively wide range. It depends on the respective content of the active compounds in the formulations and on the seed. The active compound combination application rates are generally between 0.001 and 50 g per kilogram of seed, preferably between 0.01 and 15 g per kilogram of seed.

The compounds according to the invention can be used as such or in their formulations, also in a mixture with known fungicides, bactericides, acaricides, nematicides or insecticides, to broaden, for example, the activity spectrum or to prevent development of resistances.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means limits the mycotic spectrum covered, but is only for illustration.

Accordingly, the compounds according to the invention can be used both in medical and in non-medical applications.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil.

It is also possible to treat the seed of the plants.

When using the compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. In the treatment of the soil, the application rates of active compound are generally between 0.1 and 10 000 g/ha, preferably between 1 and 5000 g/ha.

The method of treatment according to the invention is preferably applied to genetically modified organisms, such as, for example, plants or parts of plants.

Genetically modified plants (or transgenic plants) are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNA interference RNAi technology). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant species which are preferably treated according to the invention include all plants that have genetic material which imparts particularly advantageous, useful traits on these plants (regardless of whether this is achieved by cultivation and/or biotechnology).

Plants which are also preferably treated in accordance with the invention are resistant to one or more biotic stress factors, i.e. said plants have an improved defence against animal and microbial pests, such as nematodes, insects, mites, phytopathogenic fungi, bacteria, viruses and/or viroids.

In addition to the aforementioned plants and plant varieties, it is also possible in accordance with the invention to treat those which are resistant to one or more abiotic stress factors.

Abiotic stress conditions may include, for example, drought, cold exposure, heat exposure, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant varieties which may also be treated in accordance with the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated in accordance with the invention are hybrid plants that already express the characteristics of heterosis, or hybrid vigour, which generally results in higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated in accordance with the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant of the glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme of prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Further herbicide-resistant plants are plants which have been made tolerant to ACCase inhibitors.

Further plants tolerant to imidazolinone and/or sulphonylurea can be obtained by induced mutagenesis, selection in cell cultures in the presence of the herbicide or mutation breeding.

Plants or plant varieties (obtained by plant biotechnology methods such as genetic engineering) which may also be treated in accordance with the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g. proteins of the Cry protein classes Cry1Ab, Cry1Ac, Cry1F, Cry2Ab, Cry3Ae, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in corn events MON863 or MON88017, or the Cry3A protein in corn event MIR 604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated in accordance with the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants.

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may likewise be treated in accordance with the invention have an altered quantity, quality and/or storage stability of the harvested product and/or altered properties of specific ingredients of the harvested product, for example:

1) transgenic plants which synthesize a modified starch whose physicochemical characteristics, in particular the amylose content or the amylose/amylopectin ratio, the degree of branching, the average chain length, the side chain distribution, the viscosity behaviour, the gelling strength, the starch grain size and/or the starch grain morphology, is altered compared to the synthesized starch in wild type plant cells or plants, such that this modified starch is better suited for certain applications.
2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.
3) transgenic plants which produce hyaluronan.

Plants or plant cultivars (which are obtained by plant biotechnology methods such as genetic engineering) which may likewise be treated in accordance with the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (that can be obtained by plant biotechnology methods such as genetic engineering) which may also be treated in accordance with the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated in accordance with the invention are plants which comprise one or more genes which encode one or more toxins, are the following which are sold under the trade names: YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated in accordance with the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The term "active compounds" or "compounds" always also includes the active ingredient combinations mentioned here too.

PREPARATION EXAMPLES

Example I-1-a-1

Process A

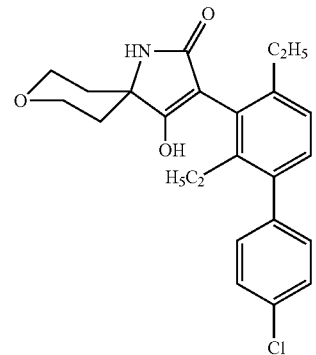

At 50° C., 2.35 g of the compound according to Ex. II-1 in 10 ml of N,N-dimethylacetamide are added dropwise to 1.29 g (10.9 mmol) of potassium tert-butoxide in 10 ml N,N-dimethylacetamide, and the mixture is stirred at 60° C. for 1 hour.

The reaction is checked by thin-layer chromatography and the reaction mixture is then added to 80 ml of ice-water and, at 0-10° C. and using 1N hydrochloric acid, adjusted to pH 2. The precipitate is filtered off with suction, washed and dried.

Chromatographic purification on silica gel using ethyl acetylate as mobile phase gives the product in a
yield of: 666 mg (30% of theory) m.p. 247° C.

$^1$H-NMR (400 MHz, d$_6$-DMSO): δ=0.80 (t, 3H, CH$_2$CH$_3$), 1.07 (t, 3H, CH$_2$CH$_3$), 1.24-1.31 (m, 2H, CH$_2$), 2.04-2.17 (m, 2H, CH$_2$), 2.3-2.41 (m, 2H, CH$_2$CH$_3$), 3.67-3.73 (m, 2H, OCH$_2$), 3.84-3.89 (m, 2H, OCH$_2$), 6.99-7.01 (d, 1H, Ar—H), 7.09-7.11 (d, 1H, Ar—H), 7.26-7.30 (m, 2H, Ar—H), 7.44-7.47 (m, 2H, Ar—H), 7.94 (br, 1H, NH) ppm.

Example I-1-a-2

Process C

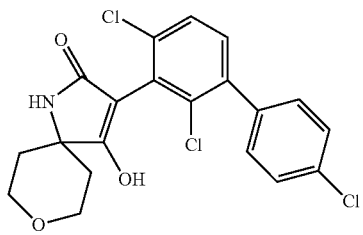 [SMILES: O=C1NC2(CCOCC2)C(O)=C1c1c(Cl)ccc(-c2ccc(Cl)cc2)c1Cl]

0.61 g (1.5 mmol) of the compound according to Ex. I-1'-a-1 is initially charged in 6.4 ml of ethylene glycol monomethyl ether and 22 ml of a 1 M solution of sodium carbonate. 7 mg of bis(triphenylphosphine)palladium(II) chloride and 0.3 g (1.9 mmol) of 4-chlorophenylboronic acid are added at room temperature, and the mixture is stirred under reflux overnight. After cooling, the mixture is extracted with ethyl acetate and the extract is washed with saturated ammonium chloride solution, dried and concentrated under reduced pressure.

This is followed by an isocratic RP separation using 25% water and 75% methanol as elution gradient.

Yield: 0.24 g (37% of theory), m.p. 273° C.

$^1$H-NMR (400 MHz, d$_6$-DMSO): δ=1.29-1.40 (m, 2H, CH$_2$), 2.02-2.12 (m, 2H, CH$_2$), 3.65-3.72 (m, 2H, OCH$_2$), 3.84-3.87 (m, 2H, OCH$_2$), 7.36-7.38 (d, 1H, Ar—H), 7.42-7.45 (m, 2H, Ar—H), 7.52-7.56 (m, 3H, Ar—H), 8.36 (br, 1H, NH) ppm.

Analogously to Examples (I-1-a-1) and (I-1-a-2) and in accordance with the general statements on the preparation, the following compounds of the formula (I-1-a) are obtained:

(I-1-a)

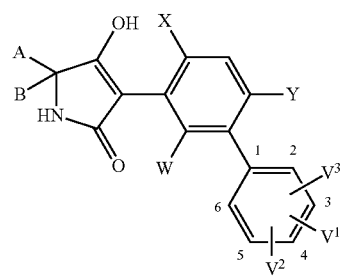

| Ex. No. | W | X | Y | V$^1$ | V$^2$ | V$^3$ | A B | M.p. ° C. | Isomer |
|---|---|---|---|---|---|---|---|---|---|
| I-1-a-3 | CH$_3$ | C$_2$H$_5$ | H | 4-Cl | H | H | —(CH$_2$)$_2$—O—(CH$_2$)$_2$— | 77 | — |
| I-1-a-4 | CH$_3$ | C$_2$H$_5$ | H | 4-F | H | H | —(CH$_2$)$_2$—CHOCH$_3$—(CH$_2$)$_2$— | 255 | β |
| I-1-a-5 | CH$_3$ | C$_2$H$_5$ | H | 4-F | H | H | —(CH$_2$)$_2$—O—(CH$_2$)$_2$— | 177 | — |
| I-1-a-6 | Cl | Cl | H | 4-F | H | H | —(CH$_2$)$_2$—O—(CH$_2$)$_2$— | 129 | — |
| I-1-a-7 | CH$_3$ | C$_2$H$_5$ | CH$_3$ | 4-Cl | H | H | —(CH$_2$)$_2$—CHOCH$_3$—(CH$_2$)$_2$— | 271-277 | β |
| I-1-a-8 | CH$_3$ | C$_2$H$_5$ | CH$_3$ | 4-Cl | H | H | —(CH$_2$)$_2$—O—(CH$_2$)$_2$— | 192 | — |
| I-1-a-9 | C$_2$H$_5$ | CH$_3$ | H | 4-F | H | H | —(CH$_2$)$_2$—CHOCH$_3$—(CH$_2$)$_2$— | *$^1$ | β |
| I-1-a-10 | C$_2$H$_5$ | CH$_3$ | H | 4-F | H | H | —(CH$_2$)$_2$—O—(CH$_2$)$_2$— | *$^2$ | — |
| I-1-a-11 | Cl | CH$_3$ | H | 4-Cl | H | H | —(CH$_2$)$_2$—O—(CH$_2$)$_2$— | 253 | — |
| I-1-a-12 | Cl | CH$_3$ | H | 4-F | H | H | —(CH$_2$)$_2$—O—(CH$_2$)$_2$— | *$^3$ | — |
| I-1-a-13 | CH$_3$ | Cl | H | 4-F | H | H | —(CH$_2$)$_2$—O—(CH$_2$)$_2$— | 208-212 | — |
| I-1-a-14 | CH$_3$ | Cl | H | 4-F | H | H | —(CH$_2$)$_2$—CHOCH$_3$—(CH$_2$)$_2$— | 335 | β |
| I-1-a-15 | CH$_3$ | Cl | H | 4-Cl | H | H | —(CH$_2$)$_2$—O—(CH$_2$)$_2$— | 73 | — |
| I-1-a-16 | C$_2$H$_5$ | CH$_3$ | H | 4-Cl | H | H | —(CH$_2$)$_2$—CHOCH$_3$—(CH$_2$)$_2$— | 289*$^4$ | β |
| I-1-a-17 | C$_2$H$_5$ | CH$_3$ | H | 4-Cl | H | H | —(CH$_2$)$_2$—O—(CH$_2$)$_2$— | 245*$^5$ | — |
| I-1-a-18 | C$_2$H$_5$ | C$_2$H$_5$ | H | 4-F | H | H | —(CH$_2$)$_2$—CHOCH$_3$—(CH$_2$)$_2$— | 247*$^6$ | β |
| I-1-a-19 | C$_2$H$_5$ | C$_2$H$_5$ | H | 4-Cl | H | H | —(CH$_2$)$_2$—CHOCH$_3$—(CH$_2$)$_2$— | 252*$^7$ | β |
| I-1-a-20 | C$_2$H$_5$ | C$_2$H$_5$ | H | 4-F | H | H | —(CH$_2$)$_2$—O—(CH$_2$)$_2$— | 97*$^8$ | — |
| I-1-a-21 | CH$_3$ | C$_2$H$_5$ | H | 4-Cl | H | H | —(CH$_2$)$_2$—CHOCH$_3$—(CH$_2$)$_2$— | 251*$^9$ | β |
| I-1-a-22 | CH$_3$ | C$_2$H$_5$ | H | 4-Cl | H | H | —(CH$_2$)$_2$—NOC$_2$H$_5$—(CH$_2$)$_2$— | 151*$^{10}$ | — |
| I-1-a-23 | CH$_3$ | C$_2$H$_5$ | H | 4-Cl | H | H | —(CH$_2$)$_2$—NOCH$_3$—(CH$_2$)$_2$— | *$^{11}$ | — |

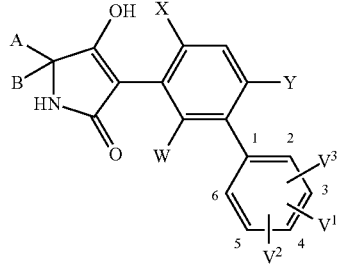

(I-1-a)

| Ex. No. | W | X | Y | V¹ | V² | V³ | A | B | M.p. °C. | Isomer |
|---|---|---|---|---|---|---|---|---|---|---|
| I-1-a-24 | C₂H₅ | C₂H₅ | H | 4-Cl | H | H | —(CH₂)₂—NOCH₃—(CH₂)₂— | | 137*[12] | — |
| I-1-a-25 | C₂H₅ | C₂H₅ | H | 4-Cl | H | H | —(CH₂)₂—NOC₂H₅—(CH₂)₂— | | 242*[13] | — | m = multiplet,
br = broad,
cm = centred multiplet

*[1] ¹H-NMR (400 MHz, d₆-DMSO): δ = 0.79 (t, 3H, CH₂CH₃), 1.38-1.59 (m, 4H, CH₂), 1.87-2.07 (m, 2H, CH₂), 2.10 (s, 3H, Ar—CH₃), 2.27-2.39 (m, 2H, CH₂CH₃), 3.11-3.16 (m, 1H, CHOCH₃), 3.26 (s, 3H, OCH₃), 6.96-6.98 (d, 1H, Ar—H), 7.08-7.10 (d, 1H, Ar—H), 7.21-7.30 (m, 4H, Ar—H), 8.07 (br, 1H, NH) ppm.

*[2] ¹H-NMR (400 MHz, d₆-DMSO): δ = 0.80 (t, 3H, CH₂CH₃), 1.22-1.32 (m, 2H, CH₂), 2.10 (s, 3H, Ar—CH₃), 3.65-3.73 (m, 2H, OCH₂), 3.84-3.87 (m, 2H, OCH₂), 6.97-6.99 (d, 1H, Ar—H), 7.09-7.11 (d, 1H, Ar—H), 7.22-7.31 (m, 4H, Ar—H), 8.36 (br, 1H, NH) ppm.

*[3] ¹H-NMR (400 MHz, d₆-DMSO): δ = 1.28-1.31 (m, 2H, CH₂), 2.09 (s, 3H, Ar—CH₃), 3.68-3.71 (m, 1H, OCH₂), 3.84-3.87 (m, 3H, OCH₂), 7.21-7.29 (m, 4H, Ar—H), 7.41-7.44 (m, 2H, Ar—H), 8.28 (br, 1H, NH) ppm.

*[4] ¹H-NMR (600 MHz, d₆-DMSO): δ = 0.79 (t, 3H, CH₂CH₃), 1.38-1.47 (dm, 2H), 1.51-1.55 (cm, 2H), 1.88-2.00 (2m, 4H), 2.10 (s, 3H, Ar—CH₃), 2.26-2.31, 2.35-2.38 (2m, 2H, CH₂CH₃), 3.12-3.16 (m, 1H, CHOCH₃), 3.26 (s, 3H, OCH₃), 6.98-6.99 (d, 1H, ArH), 7.11-7.12 (d, 1H, ArH), 7.26-7.29 (m, 2H, ArH), 7.47-7.50 (m, 2H, ArH), 8.17 (br, 1H, NH), 10.75 (s, 1H, OH) ppm.

*[5] ¹H-NMR (400 MHz, d₆-DMSO): δ = 0.79 (t, 3H, CH₂CH₃), 1.22-1.32 (m, 2H), 2.07-2.17 (m, 2H), 2.27-2.40 (m, 2H, CH₂CH₃), 3.66-3.73 (m, 2H, O—CH₂), 3.85-3.88 (m, 2H, O—CH₂), 6.98-7.00 (d, 1H, ArH), 7.11-7.13 (d, 1H, ArH), 7.27-7.29 (m, 2H, ArH), 7.47-7.49 (m, 2H, ArH), 8.36 (br, 1H, NH), 10.84 (s, 1H, OH) ppm.

*[6] ¹H-NMR (600 MHz, CD₃CN): δ = 0.81 (t, 3H, CH₂CH₃), 1.10 (t, 3H, CH₂CH₃), 1.41-1.45 (m, 2H), 1.55-1.62 (m, 2H), 2.08-2.12 (m, 2H), 2.32-2.35, 2.38-2.42 (2m, 2H, Ar—CH₂CH₃), 2.48 (q, 2H, ArCH₂CH₃), 3.21 (cm, 1H, CHOCH₃), 3.32 (s, 3H, OCH₃), 5.45 (br, 1H, NH), 7.08-7.09 (d, 1H, ArH), 7.14-7.17 (m, 3H, ArH), 7.30-7.32 (m, 2H, ArH), 7.85-8.35 (br, 1H, OH) ppm.

*[7] ¹H-NMR (400 MHz, d₆-DMSO): δ = 0.79 (t, 3H, CH₂CH₃), 1.06 (t, 3H, CH₂CH₃), 1.38-1.48 (cm, 2H), 1.51-1.58 (m, 2H), 1.87-1.99 (m, 4H), 2.26-2.39 (m, 2H, CH₂CH₃), 2.40-2.46 (q, 2H, CH₂CH₃), 3.11-3.16 (cm, 1H, CHOCH₃), 3.27 (s, 3H, OCH₃), 7.01-7.03 (d, 1H, ArH), 7.11-7.13 (d, 1H, ArH), 7.28-7.30 (m, 2H, ArH), 7.47-7.49 (m, 2H, ArH), 8.12 (br, 1H, NH), 10.67 (s, 1H, OH) ppm.

*[8] ¹H-NMR (400 MHz, d₆-DMSO): δ = 0.79 (t, 3H, CH₂CH₃), 1.07 (t, 3H, CH₂CH₃), 1.22-1.30 (cm, 2H), 2.08-2.17 (m, 2H), 2.27-2.38 (m, 2H, CH₂CH₃), 2.41-2.46 (q, 2H, CH₂CH₃), 3.66-3.73 (m, 2H, OCH₂), 3.84-3.89 (m, 2H, OCH₂), 7.02-7.04 (d, 1H, ArH), 7.11-7.13 (d, 1H, ArH), 7.22-7.32 (m, 4H), 8.38 (br, 1H, NH), 10.81 (s, 1H, OH) ppm.

*[9] ¹H-NMR (400 MHz, d₆-DMSO): δ = 1.06 (t, 3H, CH₂CH₃), 1.43-1.46 (dm, 2H), 1.48-1.58 (m, 2H), 1.88-1.96 (m, 4H), 1.97 (s, 3H, ArCH₃), 2.45 (q, 2H, ArCH₂CH₃), 3.12-3.17 (cm, 1H, CHOCH₃), 3.27 (s, 3H, OCH₃), 7.07-7.09 (d, 1H, ArH), 7.12-7.14 (d, 1H, ArH), 7.29-7.32 (m, 2H, ArH), 7.47-4.49 (m, 2H, ArH), 8.10 (br, 1H, NH), 10.65 (s, 1H, OH) ppm.

*[10] ¹H-NMR (400 MHz, d₆-DMSO): δ = 0.79 (t, 3H, CH₂CH₃), 1.10 (t, 3H, CH₂CH₃), 1.41-1.44 (mbr, 2H), 2.10 (s, 3H, ArCH₃), 2.14-2.16 (mbr, 2H), 2.26-2.35 (m, 2H, CH₂CH₃), 2.72 (cm, 2H), 3.64-3.69 (q, 2H, OCH₂CH₃), 7.08-7.10 (d, 1H, ArH), 7.13-7.15 (d, 1H, ArH), 7.26-7.32 (m, 2H, ArH), 7.46-7.50 (m, 2H, ArH), 8.22 (br, 1H, NH), 10.79 (br, 1H, OH) ppm.

*[11] ¹H-NMR (400 MHz, d₆-DMSO): δ = 0.79 (t, 3H, CH₂CH₃), 1.06 (t, 3H, CH₂CH₃), 1.43-1.46 (mbr, 2H), 2.10 (s, 3H, Ar—CH₃), 2.12-2.14 (mbr, 2H), 2.26.2.40 (m, 2H, CH₂CH₃), 2.67-2.70 (cm, 2H), 3.27-3.29 (cm, 2H), 3.44 (s, 3H, OCH₃), 7.08-7.10 (d, 1H, ArH), 7.13-7.15 (d, 1H, ArH), 7.27-7.32 (m, 2H, ArH), 7.46-7.50 (m, 2H, ArH), 8.24 (br, 1H, NH), 10.79 (br, 1H, OH) ppm.

*[12] ¹H-NMR (400 MHz, d₆-DMSO): δ = 0.79 (t, 3H, CH₂CH₃), 1.11 (t, 3H, CH₂CH₃), 1.40-1.44 (mbr, 2H), 2.15 (cmbr, 2H), 2.26-2.38 (m, 2H, CH₂CH₃), 2.40-2.45 (q, 2H, CH₂CH₃), 2.66-2.70 (mbr, 2H), 3.26-3.29 (cm, 2H), 3.44 (s, 3H, OCH₃), 7.02-7.04 (d, 1H, ArH), 7.12-7.14 (d, 1H, ArH), 7.27-7.30 (m, 2H, ArH), 7.46-7.49 (m, 2H, ArH), 8.24 (br, 1H, NH), 10.78 (br, 1H, OH) ppm.

*[13] ¹H-NMR (400 MHz, d₆-DMSO): δ = 0.79, 1.06, 1.10 (3t, 3H each, CH₂CH₃), 1.37-1.44 (cmbr, 2H), 2.16 (cmbr, 2H), 2.26-2.38 (m, 2H, CH₂CH₃), 2.40-2.45 (q, 2H, CH₂CH₃), 2.67-2.77 (cmbr, 2H), 3.21 (cmbr, 2H), 3.64-3.69 (qbr, 2H, OCH₂CH₃), 7.02-7.04 (d, 1H, ArH), 7.12-7.14 (d, 1H, ArH), 7.27-7.31 (m, 2H, ArH), 7.46-7.50 (m, 2H, ArH), 8.23 (br, 1H, NH), 10.78 (br, 1H, OH) ppm.

Example (I-1-b-1)

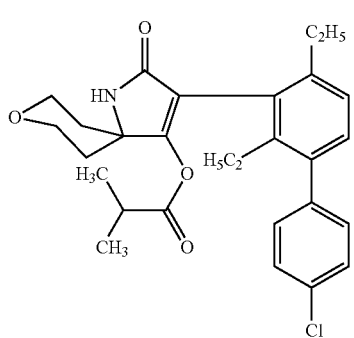

0.07 ml (0.47 mmol) of triethylamine is added to 0.15 g (0.36 mmol) of the compound according to Example (I-1-a-1) in 2 ml of methylene chloride. At room temperature, 0.04 ml (0.4 mmol) of 2-methylpropionyl chloride in 2 ml of methylene chloride are added dropwise, and the mixture is stirred overnight. The reaction mixture is added to 10 ml of water, the organic phase is separated off and concentrated under reduced pressure and the residue is purified by reversed-phase chromatography using the mobile phase system water/acetonitrile. This gives 28 mg (≙ 15% of theory).

¹H-NMR (400 MHz, CDCl₃): δ=1.00 (dd, 6H, CH(CH₃)₂), 3.63 (m, 2H, O—CH₂), 4.04 (m, 2H, OCH₂), 7.08 (d, 2H, Ar—H), 7.18 (m, 2H, Ar—H), 7.33 (d, 2H, Ar—H) ppm.

Analogously to Example (I-1-b-1) and in accordance with the general statements on the preparation, the following compounds of the formula (I-1-b) are obtained (I-1-b)

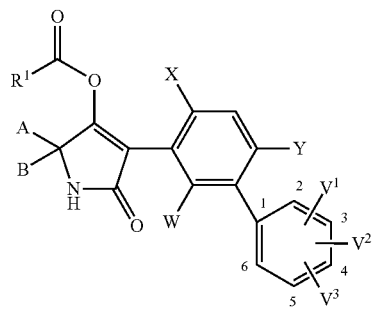

| Ex. No. | W | X | Y | V¹ | V² | V³ | A | B | R¹ | M.p. °C. | Isomer |
|---|---|---|---|---|---|---|---|---|---|---|---|
| I-1-b-2 | C$_2$H$_5$ | CH$_3$ | H | 4-F | H | H | —(CH$_2$)$_2$—CHOCH$_3$—(CH$_2$)$_2$— | | i-C$_3$H$_7$ | *1 | β |
| I-1-b-3 | CH$_3$ | C$_2$H$_5$ | H | 4-F | H | H | —(CH$_2$)$_2$—CHOCH$_3$—(CH$_2$)$_2$— | | i-C$_3$H$_7$ | *2 | β |
| I-1-b-4 | CH$_3$ | C$_2$H$_5$ | H | 4-Cl | H | H | —(CH$_2$)$_2$—CHOCH$_3$—(CH$_2$)$_2$— | | i-C$_3$H$_7$ | 93*3 | β |

I-1-b-2
*1 $^1$H-NMR (600 MHz, CDCl$_3$): δ = 0.86 (t, 3H, CH$_2$CH$_3$), 0.97, 1.02 (2d, 3H each, CH(CH$_3$)$_2$), 1.39-1.41 (m, 2H), 1.73-1.82 (m, 3H), 1.89-1.92 (m, 1H), 2.20-2.24 (m, 2H), 2.29 (s, 3H, ArCH$_3$), 2.37-2.45 (m, 2H, CH$_2$CH$_3$), 2.57 (sep, 1H, CH(CH$_3$)$_2$), 3.23 (cm, 1H, CHOCH$_3$), 3.40 (s, 3H, OCH$_3$), 6.42 (br, 1H, NH), 7.00-7.09 (m, 4H, ArH), 7.15-7.18 (m, 2H, ArH) ppm.

I-1-b-3
*2 $^1$H-NMR (400 MHz, d$_6$-DMSO): δ = 0.96, 1.01 (2d, 3H each, CH(CH$_3$)$_2$), 1.19 (t, 3H, CH$_2$CH$_3$), 1.37-1.42 (m, 2H), 1.80-1.82 (m, 3H), 1.87-1.90 (m, 1H), 2.08 (s, 3H, ArCH$_3$), 2.21-2.28 (cm, 2H), 2.49-2.60 (m, 3H, CH$_2$CH$_3$, CH(CH$_3$)$_2$), 3.23 (cm, 1H, CHOCH$_3$), 3.40 (s, 3H, OCH$_3$), 6.42 (br, 1H, NH), 7.05-7.08 (m, 2H, ArH), 7.11 (s, 2H, ArH), 7.20-7.22 (m, 2H, ArH) ppm.

I-1-b-4
*2 $^1$H-NMR (400 MHz, d$_6$-DMSO): δ = 0.87, 0.92 (2d, 3H each, CH(CH$_3$)$_2$), 1.09 (t, 3H, CH$_2$CH$_3$), 1.52-1.59 (m, 4H), 1.73-1.84 (m, 2H), 1.97-2.00 (m + s, 2H + 3H), 2.43-2.52 (m, 2H, CH$_2$CH$_3$), 2.60 (cm, 1H, CH(CH$_3$)$_2$), 3.18 (cm, 1H, CHOCH$_3$), 3.26 (s, 3H, OCH$_3$), 7.10-7.15 (m, 2H, ArH), 7.22-7.26 (m, 2H, ArH), 7.48-7.51 (m, 2H, ArH), 8.96 (br, 1H, NH) ppm.

Example (I-1-c-1)

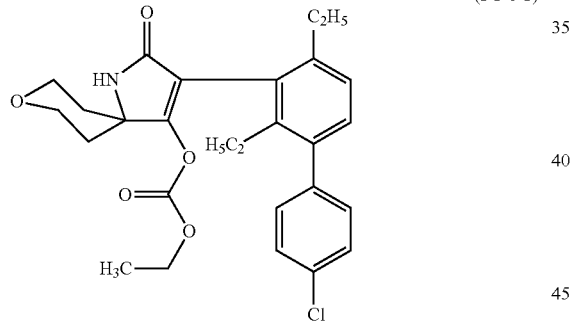

(I-1-c-1)

0.07 ml (0.47 mmol) of triethylamine are added to 0.15 g (0.36 mmol) of the compound according to Example (I-1-a-1) in 2 ml of dichloromethane. At room temperature, 0.04 ml (0.4 mmol) of ethyl chloroformate in 2 ml of dichloromethane are added dropwise, and the mixture is stirred at room temperature for 2 h. After the reaction has ended (HPLC), the reaction mixture is added to 10 ml of water, the organic phase is separated off and concentrated under reduced pressure and the residue is purified by reversed-phase chromatography using the mobile phase system water/acetonitrile. This gives 0.142 g ($\hat{=}$ 76% of theory).

$^1$H-NMR (400 MHz, CDCl$_3$): δ=3.63 (m, 2H, O—CH$_2$), 4.08 (m, 4H, OCH$_2$, O—CH$_2$CH$_3$), 7.12 (d, 2H, Ar—H), 7.19 (m, 2H, Ar—H), 7.37 (d, 2H, Ar—H) ppm.

Analogously to Example (I-1-c-1) and in accordance with the general statements on the preparation, the following compounds of the formula (I-1-c-1) are obtained

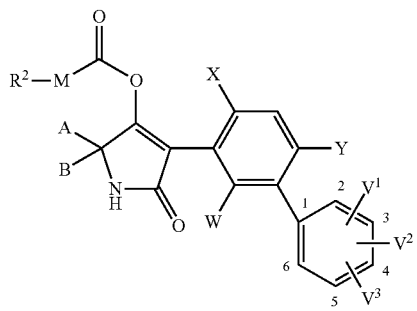

(I-1-c)

| Ex. No. | W | X | Y | V¹ | V² | V³ | A | B | M | R² | M.p. °C | Isomer |
|---|---|---|---|---|---|---|---|---|---|---|---|---|
| I-1-c-2 | CH₃ | C₂H₅ | H | 4-Cl | H | H | —(CH₂)₂—CHOCH₃—(CH₂)₂— | | O | C₂H₅ | 91 *¹ | β |
| I-1-c-3 | CH₃ | C₂H₅ | H | 4-F | H | H | —(CH₂)₂—CHOCH₃—(CH₂)₂— | | O | C₂H₅ | 80 *² | β |

I-1-c-2
*¹ ¹H-NMR (400 MHz, d₆-DMSO): δ = 0.98, 1.09 (2t, 3H each, CH₂CH₃), 1.53-1.56 (m, 4H), 1.78-1.88 (m, 2H), 1.98-2.03 (m + s, 2H + 3H), 2.42-2.48 (m, 2H, CH₂CH₃), 3.17-3.22 (cm, 1H, CHOCH₃), 3.26 (s, 3H, OCH₃), 4.00 (q, 2H, OCH₂CH₃), 7.12-7.18 (m, 2H, ArH), 7.25-7.28 (m, 2H, ArH), 7.48-7.51 (m, 2H, ArH), 9.02 (br, 1H, NH) ppm.
I-1-c-3
*¹ ¹H-NMR (400 MHz, d₆-DMSO): δ = 0.76, 0.98, 1.00, 1.09 (4t, 6H, CH₂CH₃), 1.52-1.60 (m, 4H), 1.79-1.89 (m, 2H), 1.99-2.02, 2.16 (m + 2s, 2H + 3H), 2.32-2.35, 2.43-2.48 (2m, 2H, CH₂CH₃), 3.18-3.20 (cm, 1H, CHOCH₃), 3.26 (s, 3H, OCH₃), 3.97-4.05 (m, 2H, OCH₂CH₃), 7.01-7.03, 7.10-7.12 (m, 1H, ArH), 7.14-7.15 (d, 2H, ArH), 7.24-7.28 (m, 4H, ArH), 9.02 (br, 1H, NH) ppm.

Example (I-1-f-1)

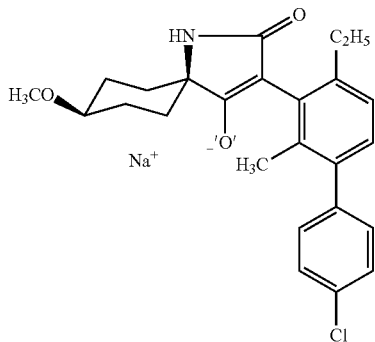

1 ml of 1N aqueous sodium hydroxide solution was diluted with 4 ml of water, and 426 mg (1 mmol) of the compound (I-1-a-21) were then introduced a little at a time. The mixture is stirred at room temperature for 30 min and concentrated to dryness. This gives 484 mg (=99% of theory).

¹H-NMR (400 MHz, d₆-DMSO): δ=1.03 (t, 3H, CH₂CH₃), 1.25-1.30 (m, 2H), 1.37-1.41 (m, 2H), 1.67-1.74 (m, 2H), 1.89-1.99 (dm, 2H), 1.99 (s, 3H, Ar—CH₃), 2.52-2.59 (m, 2H, CH₂CH₃), 3.04-3.09 (m, 1H, CH—OCH₃), 3.24 (s, 3H, OCH₃), 5.75 (br, 1H, NH), 6.83-6.84 (d, 1H, ArH), 6.93-6.95 (d, 1H, ArH), 7.24-7.27 (m, 2H, ArH), 7.42-7.45 (m, 2H, ArH) ppm.

Example II-1

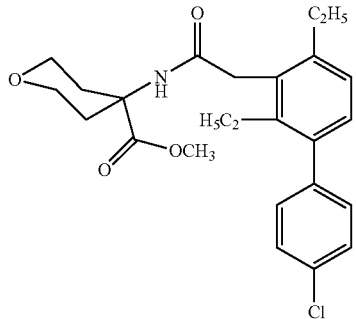

Under argon, 2.35 g of methyl 4-aminotetrahydropyran-4-carboxylate hydrochloride (12 mmol) and 50 ml of anhydrous tetrahydrofuran are initially charged.

At 20° C., 3 ml (22 mmol) of triethylamine are added dropwise.

The mixture is stirred for 5 minutes, and 4.2 g of 2,6-diethyl-5-(4-chlorophenyl)phenylacetic acid (10 mmol) are added at 20° C. After 15 minutes, 2.3 ml of triethylamine (16.5 mmol) are added dropwise, followed immediately by 0.58 ml of phosphorus oxychloride (6.2 mmol); the solution should be boiling gently. The mixture is stirred under reflux for 30 minutes.

The reaction is checked by thin-layer chromatography, the solvent is then removed using a rotary evaporator and the product is purified by column chromatography on silica gel (n-hexane:ethyl acetate=2:1)

Yield: 2.39 g (50% of theory),

¹H-NMR (400 MHz, d₆-DMSO): δ=0.88 (t, 3H, CH₂CH₃), 1.16 (t, 3H, CH₂CH₃), 1.83-1.96 (m, 4H, CH₂, 2.57-2.62 (q, 2H, Ar—CH₂CH₃), 3.54 (s, 3H, OCH₃), 3.57-3.63 (m, 2H, OCH₂), 3.70 (s, 2H, CH₂CO), 6.92-6.94 (d, 1H, Ar—H), 7.06-7.08 (d, 1H, Ar—H), 7.25-7.30 (m, 2H, Ar—H), 7.45-7.48 (m, 2H, ArH), 8.50 (s, 1H, NH) ppm.

The following compounds of the formula (II) are obtained analogously to Example (II-1) and in accordance with the general statements on the preparation:

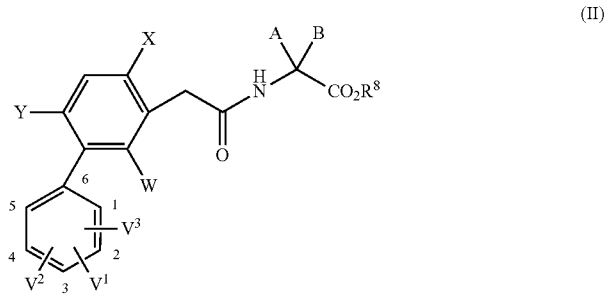

(II)

| Ex. No. | W | X | Y | $V^1$ | $V^2$ | $V^3$ | A | B | $R^8$ | M.p. °C | Isomer |
|---|---|---|---|---|---|---|---|---|---|---|---|
| II-2 | Cl | Cl | H | 4-$CF_3$ | H | H | —$(CH_2)_2$—CHCH$_3$—$(CH_2)_2$— | | $CH_3$ | 187 | β |
| II-3 | $C_2H_5$ | $C_2H_5$ | H | 4-Cl | H | H | —$(CH_2)_2$—O—$(CH_2)_2$— | | $CH_3$ | 64 | — |
| II-4 | $CH_3$ | $C_2H_5$ | H | 4-Cl | H | H | —$(CH_2)_2$—O—$(CH_2)_2$— | | $CH_3$ | *1 | — |
| II-5 | $CH_3$ | $C_2H_5$ | H | 4-F | H | H | —$(CH_2)_2$—O—$(CH_2)_2$— | | $CH_3$ | 144-145 | — |
| II-6 | $CH_3$ | $C_2H_5$ | H | 4-F | H | H | —$(CH_2)_2$—CHOCH$_3$—$(CH_2)_2$— | | $CH_3$ | *2 | β |
| II-7 | $CH_3$ | $C_2H_5$ | $CH_3$ | 4-Cl | H | H | —$(CH_2)_2$—CHOCH$_3$—$(CH_2)_2$— | | $CH_3$ | 137-138 | β |
| II-8 | $CH_3$ | Cl | H | 4-Cl | H | H | —$(CH_2)_2$—O—$(CH_2)_2$— | | $CH_3$ | *3 | — |
| II-9 | $CH_3$ | Cl | H | 4-F | H | H | —$(CH_2)_2$—O—$(CH_2)_2$— | | $CH_3$ | 247 | — |
| II-10 | $CH_3$ | $C_2H_5$ | $CH_3$ | 4-Cl | H | H | —$(CH_2)_2$—O—$(CH_2)_2$— | | $CH_3$ | 175 | — |
| II-11 | $CH_3$ | $C_2H_5$ | H | 4-Cl | H | H | —$(CH_2)_2$—CHOCH$_3$—$(CH_2)_2$— | | $CH_3$ | 60-61 | β |
| II-12 | $C_2H_5$ | $C_2H_5$ | H | 4-Cl | H | H | —$(CH_2)_2$—CHOCH$_3$—$(CH_2)_2$— | | $CH_3$ | 149 | β |
| II-13 | $C_2H_5$ | $CH_3$ | H | 4-Cl | H | H | —$(CH_2)_2$—O—$(CH_2)_2$— | | $CH_3$ | *4 | — |
| II-14 | $C_2H_5$ | $CH_3$ | H | 4-Cl | H | H | —$(CH_2)_2$—CHOCH$_3$—$(CH_2)_2$— | | $CH_3$ | 180 | β |
| II-15 | Cl | $CH_3$ | H | 4-F | H | H | —$(CH_2)_2$—O—$(CH_2)_2$— | | $CH_3$ | 159 | — |
| II-16 | Cl | $CH_3$ | H | 4-Cl | H | H | —$(CH_2)_2$—O—$(CH_2)_2$— | | $CH_3$ | *5 | — |
| II-17 | $CH_3$ | Cl | H | 4-F | H | H | —$(CH_2)_2$—CHOCH$_3$—$(CH_2)_2$— | | $CH_3$ | 182 | β |
| II-18 | $C_2H_5$ | $C_2H_5$ | H | 4-F | H | H | —$(CH_2)_2$—CHOCH$_3$—$(CH_2)_2$— | | $CH_3$ | 131 | β |
| II-19 | $C_2H_5$ | $C_2H_5$ | H | 4-F | H | H | —$(CH_2)_2$—O—$(CH_2)_2$— | | $CH_3$ | *6 | — |
| II-20 | $C_2H_5$ | $C_2H_5$ | H | 4-Cl | H | H | —$(CH_2)_2$—NOCH$_3$—$(CH_2)_2$— | | $CH_3$ | 172 | — |
| II-21 | $C_2H_5$ | $C_2H_5$ | H | 4-Cl | H | H | —$(CH_2)_2$—NOC$_2H_5$—$(CH_2)_2$— | | $CH_3$ | 166 | — |
| II-22 | $CH_3$ | $C_2H_5$ | H | 4-Cl | H | H | —$(CH_2)_2$—NOC$_2H_5$—$(CH_2)_2$— | | $CH_3$ | decomp. | — |
| II-23 | $CH_3$ | $C_2H_5$ | H | 4-Cl | H | H | —$(CH_2)_2$—NOCH$_3$—$(CH_2)_2$— | | $CH_3$ | 131 | — |

*1 $^1$H-NMR (400 MHz, $d_6$-DMSO): δ = (t, 3H), 1.17-1.9, 1.16 (t + m, 5H), 1.83-1.96 (m, 4H), 2.47, 2.59 (2q, 2H each), 3.54 (s, 3H), 3.57-2.63 (m, 2H), 1.67-3.72 (m, 2H), 3.70 (s, 2H), 6.92-6.94 (d, 1H), 7.04-7.06 (d, 1H), 7.21-7.29 (m, 4H), 8.48 (s, br, 1H) ppm.

*2 $^1$H-NMR (400 MHz, $d_6$-DMSO): δ = 1.15 (t, 3H, CH$_2$CH$_3$), 2.09 (s, 3H, Ar—CH$_3$), 2.60-2.65 (q, 2H, Ar—CH$_2$CH$_3$), 3.13-3.18 (m, 1H, CHOCH$_3$), 3.23 (s, 3H, OCH$_3$), 3.51 (s, 2H, CO$_2$CH$_3$), 3.67 (s, 2H, CH$_2$CO), 8.21 (s, 1H, NH) ppm.

*3 $^1$H-NMR (600 MHz, $d_6$-DMSO): δ = 1.85-1.94 (m, 4H, CH$_2$), 2.14 (m, 3H, Ar—CH$_3$), 3.55 (s, 3H, CO$_2$CH$_3$), 3.58-3.62 (m, 2H, OCH$_2$), 3.68-3.71 (m, 2H, OCH$_2$), 3.86 (s, 2H, CH$_2$CO), 7.10-7.11 (d, 1H, Ar—H), 7.29-7.31 (m, 2H, Ar—H), 7.33-7.35 (d, 1H, Ar—H), 7.50-7.52 (m, 2H, ArH), 8.62 (s, 1H, NH) ppm.

*4 $^1$H-NMR (400 MHz, $d_6$-DMSO): δ = 0.9 (t, 3H, CH$_2$CH$_3$), 1.85-1.99 (m, 4H, CH$_2$), 2.26 (s, 3H, Ar—CH$_3$), 3.56 (s, 3H, CO$_2$CH$_3$), 3.68 (s, 2H, CH$_2$CO), 6.87-6.88 (d, 1H, ArH), 6.98-7.08 (m, 1H, Ar—H), 7.22-7.27 (m, 2H, Ar—H), 7.43-7.46 (m, 2H, Ar—H), 8.24 (s, 1H, NH) ppm.

*5 $^1$H-NMR (600 MHz, $d_6$-DMSO): δ = 1.85-1.93 (m, 4H, CH$_2$), 2.32 (s, 3H, Ar—CH$_3$), 3.56 (s, 3H, CO$_2$CH$_3$), 3.57-3.62 (m, 2H, OCH$_2$), 3.68-3.71 (m, 2H, OCH$_2$), 3.85 (s, 2H, COCH$_2$), 7.16-7.17 (d, 1H, Ar—H), 7.22-7.24 (d, 1H, Ar—H), 7.37-7.39 (m, 2H, Ar—H), 7.50-7.52 (m, 2H, Ar—H), 8.60 (s, 1H, NH) ppm.

*6 $^1$H-NMR (400 MHz, $d_6$-DMSO): δ = 0.88 (t, 3H), 1.17-1.19, 1.16 (t + m, 5H), 1.83-1.96 (m, 4H), 2.47, 2.59 (2q, 2H each), 3.54 (s, 3H), 3.57-3.63 (m, 2H), 3.67-3.72 (m, 2H), 3.70 (s, 2H), 6.92-6.94 (d, 1H), 7.04-7.06 (d, 1H), 7.21-7.29 (m, 4H), 8.48 (sbr, 1H), ppm.

Example (I-1'-a-1)

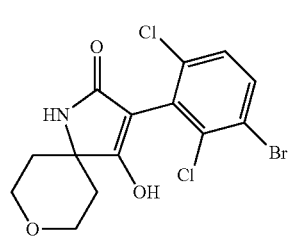 [SMILES: O=C1NC2(CCOCC2)C(O)=C1c1c(Cl)ccc(Br)c1Cl]

1.61 g of potassium tert-butoxide are initially charged in 5 ml of N,N-dimethylacetamide (DMA), 2.65 g of the compound according to Ex. II-1'-1, dissolved in 10 ml of DMA, are added dropwise at 10° C., and the mixture is stirred at room temperature for 1 h. The reaction mixture is poured onto 120 ml of ice-water, acidified with 1 N hydrochloric acid to pH 2 and filtered off with suction. The filtercake is initially washed repeatedly with water and then dried.

Yield: 2.4 g (96% of theory) m.p. 297-299° C.

$^1$H-NMR (400 MHz, $d_6$-DMSO): δ=1.31-1.36 (m, 2H, CH$_2$), 2.04-2.12 (m, 2H, CH$_2$), 3.67-3.73 (m, 2H, OCH$_2$), 3.84-3.88 (m, 2H, OCH$_2$), 7.38-7.41 (d, 1H, ArH), 7.71-7.73 (d, 1H, Ar—H), 8.21 (s, 1H, NH) ppm.

The following examples of the formula (I-1'-a) are obtained analogously to Example (I-1'-a-1) and in accordance with the general statements on the preparation in the literature mentioned at the outset (I-1'-a)

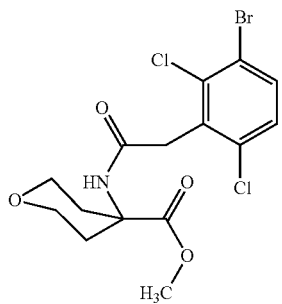 [SMILES: COC(=O)C1(NC(=O)Cc2c(Cl)ccc(Br)c2Cl)CCOCC1]

| Ex. No. | W | X | Y | Z' | A | B | M.p. °C. | Isomer |
|---|---|---|---|---|---|---|---|---|
| I-1'-a-2 | C$_2$H$_5$ | C$_2$H$_5$ | H | Br | —(CH$_2$)$_2$—CHOCH$_3$—(CH$_2$)$_2$— | | 225-228 | cis |
| I-1'-a-3 | C$_2$H$_5$ | C$_2$H$_5$ | H | Br | —(CH$_2$)$_2$—O—(CH$_2$)$_2$— | | 278 | — |

Example II-1'

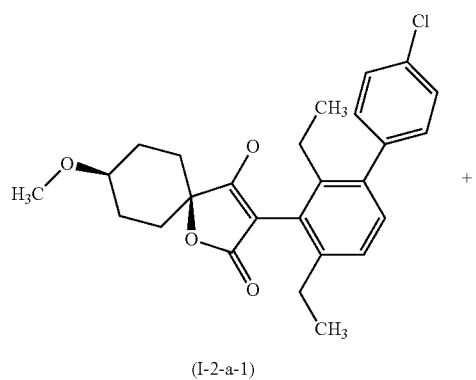

In a 100 ml three-necked flask fitted with thermometer and reflux condenser, 2.152 g (11 mmol) of methyl 4-aminotetrahydropyran-4-carboxylate hydrochloride are initially charged under argon in 50 ml of anhydrous THF. At 20° C., 3.07 ml (22 mmol) of triethylamine are added dropwise. The mixture is stirred for 5 minutes, and 2.839 g (10 mmol) of 2,6-dichloro-3-bromophenylacetic acid are added at 20° C. After 15 minutes, 2.3 ml (16.5 mmol) of triethylamine are added dropwise, followed immediately by 0.58 ml (6.2 mmol) of phosphorus oxychloride; the solution should be boiling gently. The mixture is stirred under reflux for 30 minutes, and the solvent is then distilled off. This is followed by cartridge flesh separation using the mobile phase system dichloromethane/ethyl acetate 3/1. This gives yield: 2.69 g (67.71% of theory) m.p. 209-210° C.

$^1$H-NMR (400 MHz, d$_6$-DMSO): δ=1.88-1.98 (m, 4H, CH$_2$), 3.60 (s, 3H, CO$_2$CH$_3$), 3.61-3.73 (m, 4H, OCH$_2$), 4.00 (s, 2H, COCH$_2$), 7.4-7.42 (d, 1H, ArH), 7.69-7.72 (d, 1H, Ar—H), 8.43 (br, 1H, NH) ppm.

Examples I-2-a-1 and I-2-a-2

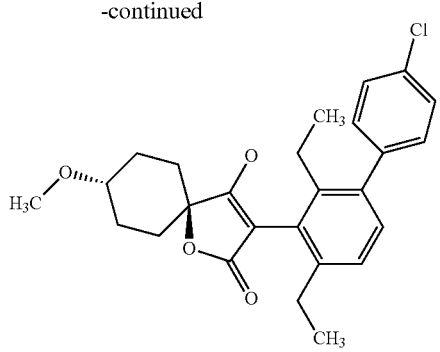

(I-2-a-1)

+

(I-2-a-2)

1.80 g (3.69 mmol) of the compound according to Example (III-1) are initially charged in 6 ml of dimethylformamide, 5.54 ml (5.54 mmol) of a 1M solution of potassium t-butoxide in tetrahydrofuran are added dropwise at 10° C. and the mixture is stirred at room temperature for 16 h. For work-up, the mixture is concentrated using a rotary evaporator and separated between water and methyl t-butyl ether, the aqueous phase is acidified with hydrochloric acid and the product is extracted with dichloromethane, dried and concentrated. This gives 750 mg of crude product.

For further purification, the crude product is separated by preparative HPLC (silica gel RP-18, acetonitrile/water/formic acid).

This gives 86 mg (11% of theory) of the cis isomer and 128 mg (16% of theory) of the transisomer.:

(I-2-a-1) cis isomer $^1$H-NMR (d$_6$-DMSO): 0.8 (t, 3H), 1.09 (t, 3H), 1.49 (m, 2H), 1.65 (m, 2H), 2.05 (m, 4H), 2.30 (m, 2H), 2.42 (m, 2H), 3.20 (s, 3H), 3.22 (m, 1H), 7.09 (m, 1H), 7.18 (m, 1H), 7.30 (m, 2H), 7.49 (m, 2H) ppm.

(I-2-a-2) trans isomer $^1$H-NMR (d$_6$-DMSO): 0.8 (t, 3H), 1.10 (t, 3H), 1.39 (m, 2H), 1.72 (m, 2H), 1.98 (m, 2H), 2.19 (m, 2H), 2.32 (m, 2H), 2.42 (m, 2H), 3.23 (s, 3H), 3.55 (m, 1H), 7.09 (m, 1H), 7.18 (m, 1H), 7.29 (m, 2H), 7.49 (m, 2H)

The following compounds of the formula (I-2-a) are obtained analogously to Examples (I-2-a-1) and (I-2-a-2) and in accordance with the general statements on the preparation:

(I-2-a)

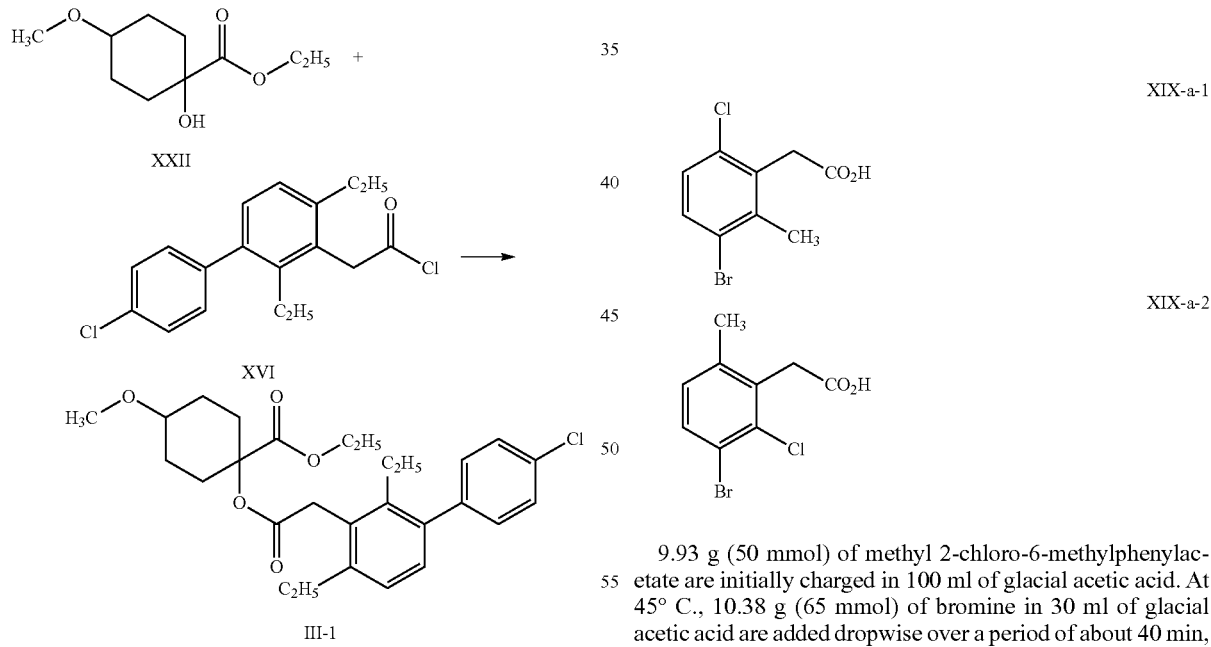

| Ex. No | W | X | Y | V¹ | V² | V³ | A | B | Analytic | Isomer |
|---|---|---|---|---|---|---|---|---|---|---|
| I-2-a-3 | $C_2H_5$ | $C_2H_5$ | H | 4-Cl | H | H | —$(CH_2)_2$—O—$(CH_2)_2$— | | *1 | — |
| I-2-a-4 | $CH_3$ | $C_2H_5$ | H | 4-Cl | H | H | —$(CH_2)_2$—C(—O—$(CH_2)_3$—)—$(CH_2)_2$)— | | *2 | trans |
| I-2-a-5 | $CH_3$ | $C_2H_5$ | H | 4-Cl | H | H | —$(CH_2)_2$—$CHOCH_3$—$(CH_2)_2$— | | *3 | trans |
| I-2-a-6 | $CH_3$ | $C_2H_5$ | H | 4-Cl | H | H | —$(CH_2)_2$—$CHOCH_3$—$(CH_2)_2$— | | *4 | cis |
| I-2-a-7 | $CH_3$ | $C_2H_5$ | H | 4-Cl | H | H | —$(CH_2)_2$—O—$(CH_2)_2$— | | *5 | — |
| I-2-a-8 | $CH_3$ | $C_2H_5$ | H | 4-Cl | H | H | —$(CH_2)_2$—C(—O—$(CH_2)_3$—)—$(CH_2)_2$)— | | *6 | cis |

*1 $^1$H-NMR (400 MHz, $d_6$-DMSO): δ = 0.80 (t, 3H), 1.09 (t, 3H), 1.5 (m, 2H), 2.12-2.52 (m, 6H), 3.62 (m, 2H), 3.95 (m, 2H), 7.08 (m, 1H), 7.15 (m, 1H), 7.30 (m, 2H), 7.50 (m, 2H) ppm.
*2 $^1$H-NMR (400 MHz, $d_6$-DMSO): δ = 1.08 (t, 3H), 1.45 (m, 2H), 1.60-2.10 (m, 12H), 1.97 (s, 3H), 3.75 (m, 2H), 7.15 (m, 2H), 7.30 (m, 2H) 7.48 (m, 2H) ppm.
*3 $^1$H-NMR (400 MHz, $d_6$-DMSO): δ = 1.08 (t, 3H), 1.40 (m, 2H), 1.54 (m, 2H), 1.90-2.20 (m, 6H), 1.99 (s, 3H), 3.28 (s, 3H), 3.55 (m, 1H), 7.15 (m, 2H), 7.30 (m, 2H), 7.49 (m, 2H) ppm.
*4 $^1$H-NMR (400 MHz, $d_6$-DMSO): δ = 1.08 (t, 3H), 1.45 (m, 2H), 1.55 (m, 2H), 1.90-2.10 (m, 6H), 2.00 (s, 3H), 3.25 (m, 1H), 3.30 (s, 3H), 7.15 (m, 2H), 7.30 (m, 2H), 7.48 (m, 2H) ppm.
*5 $^1$H-NMR (400 MHz, $d_6$-DMSO): δ = 1.09 (t, 3H), 1.52 (m, 2H), 2.00 (s, 3H), 2.19 (m, 4H), 3.65 (m, 2H), 3.95 (m, 2H), 7.18 (m, 2H), 7.32 (m, 2H), 7.50 (m, 2H) ppm.
*6 $^1$H-NMR (400 MHz, $d_6$-DMSO): δ = 1.09 (t, 3H), 1.60-2.10 (m, 12H), 1.95 (s, 3H), 3.75 (m, 2H), 7.15 (m, 2H), 7.30 (m, 2H), 7.48 (m, 2H) ppm.

Example (III-1)

0.94 g (466 mmol) of ethyl 1-hydroxy-4-methoxy-cyclohexanecarboxylate and 1.50 g (4.66 mmol) of (4'-chloro-2,6-dimethylbiphenyl-3-yl)acetyl chloride in 30 ml of toluene are boiled at reflux for 16 h. For work-up, the mixture is concentrated using a rotary evaporator, the residue is partitioned between dilute aqueous sodium hydroxide solution and methyl t-butyl ether and the organic phase is dried and concentrated using a rotary evaporator. Yield: 1.8 g of crude product which is used directly further in the next step for preparing the compounds (I-2-a-1) and (I-2-a-2).

Examples XIX-a-1 and XIX-a-2

9.93 g (50 mmol) of methyl 2-chloro-6-methylphenylacetate are initially charged in 100 ml of glacial acetic acid. At 45° C., 10.38 g (65 mmol) of bromine in 30 ml of glacial acetic acid are added dropwise over a period of about 40 min, and the mixture is stirred at 45° C. overnight. After evaporation of the glacial acetic acid under reduced pressure, the residue is taken up in saturated sodium chloride solution and dichloromethane, extracted, dried and concentrated under reduced pressure. The residue is purified by flash column chromatography on silica gel using ethyl acetate. 11.4 g of the mixture of isomers obtained are dissolved in 55 ml of ethanol, and 35 ml of 2 N aqueous sodium hydroxide solution are then added dropwise. The mixture is stirred at 50° C. for 2 h, the ethanol is evaporated, the residue is diluted with about 100 ml of water, the mixture is acidified with concentrated hydrochloric acid and the product is filtered off with suction. This gives yield: 8.79 g (74% of theory) of the isomeric acids in a ratio of about 2.5:1.

XIX-a-1: $^1$H-NMR (400 MHz, $d_6$-DMSO): δ=2.38 (s, 3H, Ar—CH$_3$), 3.87 (s, 2H, C$\underline{H_2}$CO), 7.23-7.25 (d, 1H, ArH), 7.51-7.53 (d, 1H, Ar—H) ppm.

XIX-a-2: $^1$H-NMR (400 MHz, $d_6$-DMSO): δ=2.27 (s, 3H, Ar—CH$_3$), 3.83 (s, 2H, C$\underline{H_2}$CO), 7.11-7.13 (d, 1H, ArH), 7.53-7.55 (d, 1H, Ar—H) ppm.

The following examples of the formula (XIX-a) are obtained analogously to Examples (XIX-a-1) and (XIX-a-2)

XIX-a

| Ex. No. | W | X | Y | $^1$H-NMR 400 MHz, $d_6$-DMSO |
|---|---|---|---|---|
| XIX-a-3 | C$_2$H$_5$ | C$_2$H$_5$ | H | δ = 1.08, 1.12 (2t, 3H each, CH$_2$—CH$_3$), 2.54-2.60 (q, 2H, CH$_2$CH$_3$), 2.76-2.81 (q, 2H, CH$_2$CH$_3$), 3.70 (s, 2H, CH$_2$CO), 6.98, 7.41 (2d, 1H each, Ar—H) ppm. |

Example XIX-1

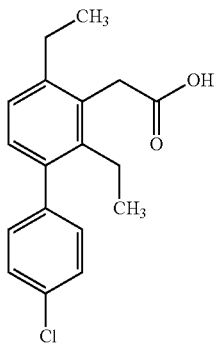 [SMILES: CCc1ccc(-c2ccc(Cl)cc2)c(CC)c1CC(=O)O]

Under an atmosphere of protective gas, 27 g (60 mmol) of the compound according to Example XIX-a-3 are initially charged in 420 ml of ethylene glycol dimethyl ether at room temperature. 126 ml of a 1 M solution of sodium carbonate are added dropwise, and 0.3 g (0.427 mmol) of bis(triphenylphosphine)palladium(II) chloride is then metered in at room temperature, followed by 11.728 g (75 mmol) of 4-chlorophenylboronic acid, likewise at room temperature.

The reaction mixture is stirred under reflux overnight. The mixture is then extracted with water and ethyl acetate, the organic phase is washed with saturated ammonium chloride solution, water and brine and dried and the solvent is distilled off. The product is recrystallized from MTB ether/n-hexane.

This gives 16.3 g (89.7% of theory).

$^1$H-NMR (400 MHz, $d_6$-DMSO): δ=0.88 (t, 3H, CH$_2$C$\underline{H_3}$), 1.17 (t, 3H, CH$_2$C$\underline{H_3}$), 2.56-2.67 (m, 4H, C$\underline{H_2}$CH$_3$), 3.71 (s, 2H, C$\underline{H_2}$CO), 6.96-6.98 (d, 1H, Ar—H), 7.11-7.13 (d, 1H, ArH), 7.26-7.30 (m, 2H, Ar—H), 7.45-7.49 (m, 2H, ArH) ppm.

Examples XIX-2 and XIX-3

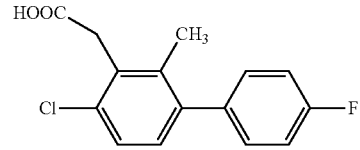

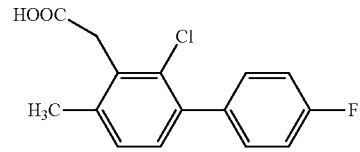

4.3 g (15 mmol) of the isomer mixture of the compounds (XIX-a-3) and (XIX-a-4) are initially charged in 60 ml of ethylene glycol dimethyl ether at room temperature. 105 ml of a 2 N solution of sodium carbonate are then added dropwise, 0.0749 g (0.105 mmol) of bis(triphenylphosphine)palladium(II) chloride is metered in at room temperature, followed by 2.938 g (21 mmol) of 4-fluorophenylboronic acid at room temperature. The reaction mixture is stirred under reflux overnight. The mixture is extracted with water and ethyl acetate, and the organic solution is extracted with saturated ammonium chloride solution, washed with water and brine, dried and concentrated on a rotary evaporator. The residue is titrated with acetonitrile and filtered off with suction. This gives 2.278 g (94.06% pure) of 2 isomers ($\hat{=}$ 51% of theory) in a ratio of about 1:6. The isomers are separated by HPLC on an RP phase using water/methanol.

XIX-2: $^1$H-NMR (400 MHz, $d_6$-DMSO): δ=2.15 (s, 3H, ArCH$_3$), 3.86 (s, 2H, COC$\underline{H_2}$), 7.13-7.14 (d, 1H, Ar—H), 7.27-7.37 (m, 5H, ArH) ppm.

XIX-3: $^1$H-NMR (400 MHz, $d_6$-DMSO): δ=2.33 (s, 3H, ArCH$_3$), 3.84 (s, 2H, C$\underline{H_2}$CO), 7.18-7.20 (d, 1H, Ar—H), 7.25-7.48 (m, 5H, ArH) ppm.

The following compounds of the formula (XIX) are obtained analogously to Examples (XIX-1), (XIX-2) and (XIX-3):

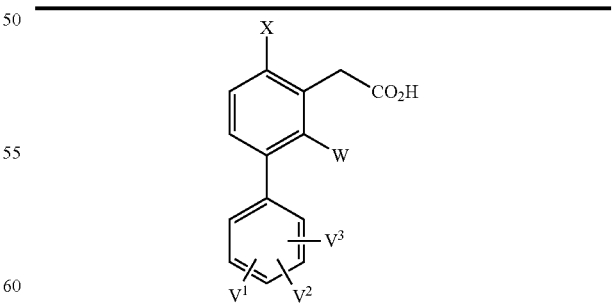

| Ex. No. | W | X | Y | V$^1$ | V$^2$ | V$^3$ | $^1$H-NMR (400 MHz, $d_6$-DMSO) δ: in ppm |
|---|---|---|---|---|---|---|---|
| XIX-5 | C$_2$H$_5$ | CH$_3$ | H | 4-F | H | H | *1 |
| XIX-6 | CH$_3$ | C$_2$H$_5$ | H | 4-F | H | H | *2 |
| XIX-7 | C$_2$H$_5$ | CH$_3$ | H | 4-Cl | H | H | *3 |

-continued

| | | | | | | | |
|---|---|---|---|---|---|---|---|
| XIX-8 | CH$_3$ | C$_2$H$_5$ | H | 4-Cl | H | H | *4 |
| XIX-4 | CH$_3$ | Cl | H | 4-Cl | H | H | *5 |

*1 0.88 (t, 3H, CH$_2$CH$_3$), 2.27 (s, 3H, ArCH$_3$), 3.69 (s, 2H, COCH$_2$), 6.90-6.92 (d, 1H, Ar—H), 7.05-7.07 (d, 1H, Ar—H), 7.21-7.29 (m, 4H, Ar—H) ppm.
*2 1.16 (t, 3H, CH$_2$CH$_3$), 2.10 (s, 3H, ArCH$_3$), 3.70 (s, 2H, COCH$_2$), 7.02-7.04 (d, 2H, Ar—H), 7.09-7.11 (d, 1H, Ar—H), 7.22-7.31 (m, 4H, Ar—H) ppm.
*3 0.89 (t, 3H, CH$_2$CH$_3$), 2.27 (s, 3H, ArCH$_3$), 2.48-2.51 (q, 2H, CH$_2$CH$_3$), 3.69 (s, 2H, COCH$_2$), 6.91-6.92 (d, 1H, ArH), 7.07-7.08 (d, 1H, Ar—H), 7.26-7.28 (m, 2H, Ar—H), 7.46-7.48 (m, 2H, Ar—H) ppm
*4 1.17 (t, 3H, CH$_2$CH$_3$), 2.11 (s, 3H, ArCH$_3$), 2.63-2.68 (q, 2H, CH$_2$CH$_3$), 3.70 (s, 2H, COCH$_2$), 7.01-7.03 (d, 1H, Ar—H), 7.09-7.11 (d, 1H, Ar—H), 7.24-7.29 (m, 2H, Ar—H), 7.43-7.47 (m, 2H, Ar•H) ppm.
*5 2.14 (s, 3H, ArCH$_3$), 3.85 (s, 2H, CH$_2$CO), 7.12-7.14 (d, 2H, Ar—H), 7.30-7.32 (m, 2H, Ar—H), 7.36-7.38 (d, 1H, Ar—H), 7.50-7.52 (m, 2H, Ar•H) ppm.

Use Examples

Example 1

*Phaedon* Test (PHAECO Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, one part by weight of active compound is mixed with the stated amounts of solvents and emulsifier, and the concentrate is diluted with emulsifier-containing water to the desired concentration. Discs of Chinese cabbage (*Brassica pekinensis*) are sprayed with an active compound preparation of the desired concentration and, after drying, populated with larvae of the mustard beetle (*Phaedon cochleariae*).

After 7 days, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of 83%: I-1-a-4, I-1-a-9.

In this test, for example, the following compounds of the Preparation Examples show, at an application rate of 500 g/ha, an efficacy of 100%: I-1-a-1, I-1-a-3, I-1-a-7, I-1-a-8, I-1-a-12, I-1-a-14, I-1-a-19, I-1-a-22, I-1-a-23, I-1-a-25, I-2-a-1, I-2-a-5, I-2-a-6, I-2-a-8.

Example 2

*Spodoptera frugiperda* Test (SPODFR Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsified water to the desired concentration. Discs of maize leaves (*Zea mays*) are sprayed with an active compound preparation of the desired concentration and, after drying, populated with caterpillars of the armyworm (*Spodoptera frugiperda*).

After 7 days, the effect in % is determined. 100% means that all caterpillars have been killed; 0% means that none of the caterpillars have been killed.

In this test, for example, the following compounds of the Preparation Examples show, at an application rate of 500 g/ha, an efficacy of 80%: I-1-a-3.

In this test, for example, the following compounds of the Preparation Examples show, at an application rate of 500 g/ha, an efficacy of 83%: I-1-a-11, I-1-a-15, I-1-b-1.

In this test, for example, the following compounds of the Preparation Examples show, at an application rate of 500 g/ha, an efficacy of 100%: I-1-a-2, I-1-a-12, I-1-a-13, I-1-a-14, I-1-a-16, I-1-b-4, I-2-a-7.

Example 3

*Myzus* Test (MYZUPE Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of Chinese cabbage (*Brassica pekinensis*) which are infested by all stages of the green peach aphid (*Myzus persicae*) are sprayed with an active compound preparation of the desired concentration. After 6 days, the effect in % is determined. 100% means that all aphids have been killed; 0% means that none of the aphids have been killed.

In this test, for example, the following compounds of the Preparation Examples show, at an application rate of 500 g/ha, an efficacy of 90%: I-1-a-4, I-1-a-9, I-1-b-2, I-1-b-3, I-1-c-1, I-2-a-1, I-2-a-2, I-2-a-3, I-2-a-4, I-2-a-5.

In this test, for example, the following compounds of the Preparation Example show, at an application rate of 500 g/ha, an efficacy of 100%: I-1-a-1, I-1-a-2, I-1-a-3, I-1-a-5, I-1-a-6, I-1-a-8, I-1-a-10, I-1-a-11, I-1-a-12, I-1-a-13, I-1-a-14, I-1-a-15, I-1-a-16, I-1-a-17, I-1-a-18, I-1-a-20, I-1-a-21, I-1-a-22, I-1-a-23, I-1-a-25, I-1-b-4, I-1-c-2, I-1-c-3, I-2-a-6, I-2-a-7.

In this test, for example, the following compounds of the Preparation Examples show, at an application rate of 100 g/ha, an efficacy of 90%: I-1-a-7.

Example 4

*Tetranychus* Test; OP-Resistant (TETRUR Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of bean leaves (*Phaseolus vulgaris*), which are infested by all stages of the greenhouse red spider mite (*Tetranychus urticae*) are sprayed with an active compound preparation of the desired concentration.

After 6 days, the effect in % is determined. 100% means that all spider mites have been killed; 0% means that none of the spider mites have been killed.

In this test, for example, the following compounds of the Preparation Examples show, at an application rate of 100 g/ha, an efficacy of 70%: I-1-a-9

In this test, for example, the following compounds of the Preparation Examples show, at an application rate of 100 g/ha, an efficacy of 100%: I-1-a-4, I-1-a-6, I-1-a-10, I-1-a-11, I-1-a-12, I-1-a-13, I-1-a-17, I-1-a-18, I-1-a-20, I-1-a-21, I-1-a-24, I-1-a-25, I-1-b-3, I-1-c-2, I-2-a-1, I-2-a-3, I-2-a-6, I-2-a-7.

In this test, for example, the following compounds of the Preparation Examples show, at an application rate of 100 g/ha, an efficacy of 90%: I-1-a-3, I-1-a-5, I-1-a-7, I-1-a-8, I-1-a-14, I-1-a-15, I-1-a-16, I-1-a-19, I-1-a-22, I-1-a-23, I-1-b-4, I-1-c-3, I-2-a-8.

In this test, for example, the following compounds of the Preparation Examples show, at an application rate of 100 g/ha, an efficacy of 80%: I-1-a-1, I-1-b-1.

Example 5

*Meloidogyne incognita* Test (MELGIN)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with water to the desired concentration. Containers are filled with sand, solution of active compound, *Meloidogyne incognita* egg/larvae suspension and lettuce seeds. The lettuce seeds germinate and the plants develop. On the roots, galls are formed. After 14 days, the nematicidal activity is determined in % by the formation of galls. 100% means that no galls are found; 0% means that the number of galls on the treated plants corresponds to that of the untreated controls.

In this test, for example, the following compounds of the Preparation Examples show, at an application rate of 20 ppm, an efficacy of >80%: I-1-a-11

Example 6

*Boophilus microplus* Test (BOOPMI Injection)
Solvent: Dimethyl sulphoxide

To produce a suitable preparation of active compound, 10 mg of active compound are mixed with 0.5 ml of solvent and the concentrate is diluted with solvent to the desired concentration. The solution of active compound is injected into the abdomen (*Boophilus microplus*) and the animals are transferred into dishes and stored in a climatized room. The efficacy is monitored for deposition of fertile eggs.

After 7 days, the effect in % is determined. 100% means that none of the ticks has laid any fertile eggs.

In this test, for example, the following compounds of the Preparation Examples show, at an application rate of 20 µg/animal, an efficacy of 80%: I-1-a-3, I-1-a-10, I-1-a-13.

In this test, for example, the following compounds of the Preparation Examples show, at an application rate of 20 µg/animal, an efficacy of 90%: I-1-a-6, I-1-a-11.

In this test, for example, the following compounds of the Preparation Examples show, at an application rate of 20 µg/animal, an efficacy of 95%: I-1-a-2, I-1-a-12, I-1-a-14.

In this test, for example, the following compounds of the Preparation Examples show, at an application rate of 20 µg/animal, an efficacy of 100%: I-1-a-9.

Example 7

*Lucilia cuprina* test (LUCICU)
Solvent: Dimethyl sulphoxide

To produce a suitable preparation of active compound, 10 mg of active compound are mixed with 0.5 ml of dimethyl sulphoxide and the concentrate is diluted with water to the desired concentration. Containers containing horse meat treated with the active compound preparation of the desired concentration are populated with about 20 *Lucilia cuprina* larvae.

After 2 days, the kill in % is determined. 100% means that all larvae have been killed; 0% means that none of the larvae have been killed.

In this test, for example, the following compounds of the Preparation Examples show, at an application rate of 100 ppm, an efficacy of 90%: I-1-a-10, I-1-a-13.

In this test, for example, the following compounds of the Preparation Examples show, at an application rate of 100 ppm, an efficacy of 100%: I-1-a-2, I-1-a-11, I-1-a-12, I-1-a-14, I-1-a-15.

Example 8

1. Herbicidal Pre-Emergence Action
   Seeds of monocotyledonous and dicotyledonous weed and crop plants are placed in sandy loam in wood fibre pots and covered with soil. The test compounds, formulated in the form of wettable powders (WP), are then, as aqueous suspension with a water application rate of 600 l/ha (converted), with 0.2% of wetting agent added, applied in various dosages to the surface of the covering soil.
   After the treatment, the pots are placed in a greenhouse and kept under good growth conditions for the test plants. The visual assessment of the emergence damage on the test plants is carried out after a trial period of about 3 weeks by comparison with the untreated controls (herbicidal effect in %: 100% effect=the plants have died, 0% effect=like control plants).
   In addition to the compounds mentioned above, the following compounds, applied by the pre-emergence method at 320 g of a.i./ha, show an efficacy of 80-100% against *Alopecurus myosuroides, Echinocloa crus-galli, Lolium multiflorum* and *Setaria viridis*: I-1-a-3, I-1-a-4, I-1-a-7, I-1-a-11, I-1-a-14, I-1-a-16, I-1-a-18, I-1-a-19, I-1-a-21, I-1-a-22, I-1-a-25, I-1-b-3, I-1-b-4, I-1-c-1, I-1-c-2, I-1-c-3.
2. Herbicidal Post-Emergence Action
   Seeds of monocotyledonous and dicotyledonous weed and crop plants are placed in sandy loam in wood fibre pots, covered with soil and cultivated in a greenhouse under good growth conditions. 2-3 weeks after sowing, the test plants are treated at the one-leaf stage. The test compounds, formulated as wettable powders (WP), are, in various dosages at a water application rate of 600 l/ha (converted), with 0.2% wetting agent added, sprayed onto the green parts of the plants. After the test plants have been kept in the greenhouse under optimum growth conditions for about 3 weeks, the effect of the preparations is rated visually in comparison to the untreated controls (herbicidal effect in %: 100% effect=the plants have died, 0% effect=like control plants).
   In addition to the compounds mentioned above, the following compounds, applied by the post-emergence method at 80 g/ha, show an efficacy of 80-100% against *Alopecurus myosuroides, Avena fatua, Echinocloa crus-galli, Lolium multiflorum* and *Setaria viridis*: I-1-a-1, I-1-a-3, I-1-a-11, I-1-a-18, I-1-a-22, I-1-a-24.
   In addition to the compounds mentioned above, the following compounds, applied by the post-emergence method at 80 g/ha, show an efficacy of 90-100% against *Alopecurus myosuroides, Echinocloa crus-galli, Lolium multiflorum* and *Setaria viridis*: I-1-a-4, I-1-a-8, I-1-a-19, I-1-b-4, I-1-c-3, I-2-a-6.

Example 9

Increase of Penetration into the Plant by Ammonium or Phosphonium Salts and Synergistic Increase of Penetration into the Plant by Ammonium/Phosphonium Salts in Combination with Penetrants In this test, the penetration of active compounds through enzymatically isolated cuticles of apple tree leaves is measured.

Use is made of leaves which, fully developed, are cut from apple trees of the cultivar Golden Delicious. The cuticles are isolated by initially filling leaf discs punched out and stained with dye on the underside by vacuum infiltration with a pectinase solution (0.2 to 2% strength) buffered to a pH between 3 and 4, then sodium azide is added and the leaf discs treated in this manner are allowed to stand until the original leaf structure has dissolved and the non-cellular cuticles have detached.

Only the cuticles, free from hairs and stoma, of the upper sides of the leaves are then used. They are washed repeatedly alternating with water and a buffer solution of pH 7. The clean cuticles obtained are then mounted on Teflon plates and smoothed and dried with a gentle stream of air.

In the next step, the cuticle membranes obtained in this manner are placed into stainless steel diffusion cells (=transport chambers) for membrane transport studies. To this end, the cuticles are placed with a pincette into the centre of the edges, coated with silicone fat, of the diffusion cells and closed with a ring, which is also treated with fat. The arrangement is chosen such that the morphological outside of the cuticles is facing outwards, i.e. exposed to air, whereas the original inside is facing the interior of the diffusion cell.

The diffusion cells are filled with a 30% strength ethylene glycol/water solution. To determine the penetration, in each case 10 μl of the spray liquor of the composition below are applied to the outside of the cuticles. The spray liquor is prepared using local tap water of medium hardness.

After the application of the spray liquors, the water is allowed to evaporate and the chambers are inverted and placed into thermostatic tubs in which temperature and atmospheric humidity over the cuticles can be adjusted using a gentle stream of air onto the cuticles with the spray coating (35° C., 60% rh). At regular intervals, an autosampler takes aliquots and the active compound content is determined by HPLC.

The test results are shown in the table below. The stated numbers are average values of 8 to 10 measurements. It is clearly evident that even ammonium sulphate on its own improves the penetration markedly, and that, together with RME, a super additive (synergistic) effect is present.

| Active compound | Penetration after 48 h/% | | | |
|---|---|---|---|---|
| | EC | EC + AS (0.7 g/l) | EC + RME (1 g/l) | EC + RME (1 g/l) + AS (0.7 g/l) |
| <br>Example I-1-a-25<br>0.2 g/l<br>500 ppm in DMF/emulsifier W 7:1 (w/w) | 0 | 2 | 4 | 10 |

RME = rapeseed oil methyl ester (use formulated as 500 EW, concentration stated in g of active compound/l)
AS = ammonium sulphate
EC = emulsifiable concentrate

The invention claimed is:

1. A compound of formula (I)

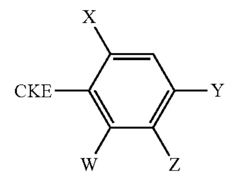

(I)

in which

W represents halogen or alkyl,

X represents halogen, alkyl or halogenalkyl,

Z represents optionally mono- or polysubstituted phenyl,

Y represents hydrogen, halogen, alkyl, alkoxy, haloalkyl or haloalkoxy, with the proviso that at least one of the radicals W or X represents halogen or ethyl, CKE represents one of the groups 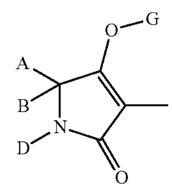 (1)

or 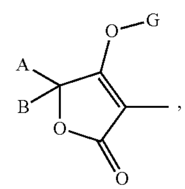 (2)

, in which

A represents hydrogen, represents in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, halogenalkyl-, alkoxy-, halogenalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, represents in each case optionally substituted arylalkyl, aryl, hetarylalkyl or hetaryl or A and D together with the atoms to which they are attached represent a saturated or unsaturated cycle which is unsubstituted or substituted in the A,D moiety and optionally contains at least one heteroatom, G represents hydrogen (a) or represents one of the groups

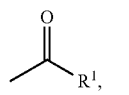
(b)

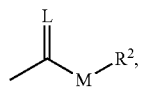
(c)

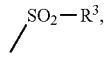
(d)

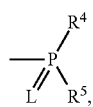
(e)

E or
(f)

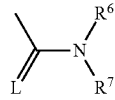
(g)

in which

E represents a metal ion or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl-or alkoxy-substituted cylcoalkyl which may be interrupted by at least one heteroatom,
  in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the nitrogen atom to which they are attached represent a ring which is optionally interrupted by oxygen or sulphur.

2. A compound of the formula (I) according to claim 1 in which

W represents halogen or $C_1$-$C_4$-alkyl,

X represents halogen, $C_1$-$C_6$-alkyl or $C_1$-$C_6$-haloalkyl,

Z represents a radical

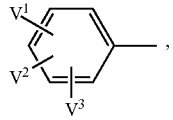

$V^1$ represents hydrogen, halogen, $C_1$-$C_6$-alkyl, $C_1$-$C_6$-alkoxy, $C_1$-$C_6$-alkylthio, $C_1$-$C_6$-alkylsulphynyl, $C_1$-$C_6$-alkylsulphonyl, $C_1$-$C_4$-haloalkyl, $C_1$-$C_4$-haloalkoxy, nitro or cyano, $V^2$ represents hydrogen, halogen, $C_1$-$C_6$-alkyl or $C_1$-$C_6$-alkoxy, V3 represents hydrogen, halogen, $C_1$-$C_6$-alkyl or $C_1$-$C_6$-alkoxy, Y represents hydrogen, halogen, $C_1$-$C_6$-alkyl, $C_1$-$C_6$-haloalkyl, $C_1$-$C_6$-alkoxy or $C_1$-$C_6$-haloalkoxy, with the proviso that at least one of the radicals W or X represents halogen or ethyl, CKE represents one of the groups

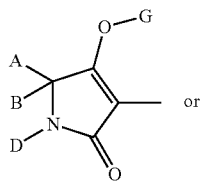
(1)

or

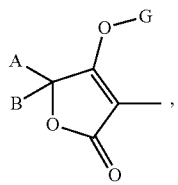
(2)

A represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio -$C_1$-$C_6$-alkyl, optionally halogen-, $C_1$-$C_6$-alkyl- or $C_1$-$C_6$-alkoxy-substituted $C_3$-$C_8$-cycloalkyl, in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 or 6 ring atoms, phenyl-$C_1$-$C_6$-alkyl or naphthyl -$C_1$-$C_6$-alkyl, B represents hydrogen, $C_1$-$C_{12}$-alkyl or $C_1$-$C_8$-alkoxy-$C_1$-$C_6$-alkyl or A, B and a carbon atom to which they are attached represent saturated $C_3$-$C_{10}$-cycloalkyl or unsaturated $C_5$-$C_{10}$-cycloalkyl, in which optionally one ring member is replaced by oxygen, nitrogen or sulphur and which are optionally mono- or disubstituted by $C_1$-$C_8$-alkyl, $C_1$-$C_8$-alkoxy, $C_3$-$C_8$-alkenyloxy, $C_1$-$C_6$-alkoxy-$C_1$-$C_6$-alkyl, $C_1$-$C_6$-alkoxy-$C_1$-$C_6$-alkoxy, $C_3$-$C_6$-cycloalkyl-$C_1$-$C_2$-alkoxy, $C_3$-$C_{10}$-cycloalkyl, $C_1$-$C_8$-haloalkyl or $C_2$-$C_6$-haloalkoxy or $C_1$-$C_6$-alkoxy-$C_1$-$C_4$-alkoxy, where the radicals mentioned above are also suitable as substituents of nitrogen, or A, B and the carbon atom to which they are attached represent $C_3$-$C_6$-cycloalkyl which is substituted by an alkylenediyl group which is optionally substituted by $C_1$-$C_4$-alkyl and optionally contains one or two not directly adjacent oxygen and/or sulphur atoms, or by an alkylenedioxyl or by an alkylenedithioyl group which, together with the carbon atom to which it is attached, forms a further five- to eight-membered ring or A, B and the carbon atom to which they are attached represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanediendiyl in which optionally one methylene group is replaced by oxygen or sulphur, D represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano-or nitro-substituted phenyl, hetaryl having 5 or 6 ring atoms, phenyl-$C_1$-$C_6$-alkyl or hetaryl-$C_1$-$C_6$-alkyl having 5or 6ring atoms or A and D together represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case:

halogen, hydroxy, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1), A and D then together with the atoms to which they are attached represent the groups AD-1 to AD-10 mentioned further below) which may contain oxygen or sulphur, or which optionally contains one of the groups below

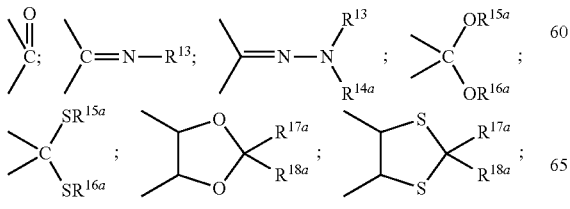

-continued

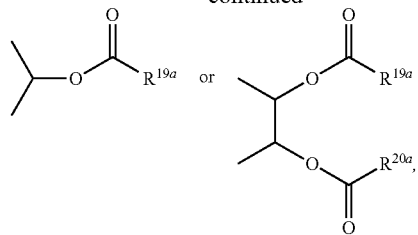

G represents hydrogen (a) or represents one of the groups (b)

(c)

(d)

(e)

(f)

E or (g)

in which

E represents a metal ion or an ammonium ion,

L represents oxygen or sulphur and

M represents oxygen or sulphur, $R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more not directly adjacent ring members are replaced by oxygen and/or sulphur, represents optionally halogen- cyano-, nitro-, $C_1$-$C_6$-alkyl-, $C_1$-$C_6$-alk-oxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alk-oxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-memberedhetaryl, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl, $R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ represents optionally halogen-substituted $C_1$-$C_8$-alkyl or represents optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen-substituted $C_1$-$C_8$-alkyl, $C_3$-$C_8$-cycloalkyl, $C_1$-$C_8$-alkoxy, $C_3$-$C_g$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one methylene group is replaced by oxygen or sulphur, $R^{13}$ represents hydrogen, represents in each case optionally halogen-substituted $C_1$-$C_8$-alkyl or $C_1$-$C_8$-alkoxy (only in the case of the C=N—$R^{13}$ group), represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl, hetaryl-$C_1$-$C_4$-alkyl, or, only in the case of the C=N—$R^{13}$ group, represents phenyl-$C_1$-$C_4$-alkoxy or hetaryl-$C_1$-$C_4$-alkoxy, $R^{14a}$ represents hydrogen or $C_1$-$C_8$-alkyl or $R^{13}$ and $R^{14a}$ together represent optionally $C_1$-$C_4$-alkyl-substituted $C_4$-$C_6$-alkanediyl which may optionally be interrupted by oxygen or sulphur, $R^{15a}$ and $R^{16a}$ are identical or different and represent $C_1$-$C_6$-alkyl or $R^{15a}$ and $R^{16a}$ together represent a $C_2$-$C_4$-alkanediyl radical or $C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ dependently of one another represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di($C_1$-$C_{10}$-alkyl)amino or di($C_3$-$C_{10}$-alkenyl)amino.

3. A compound of the formula (I) according to claim 1 in which

W represents methyl, ethyl, fluorine or chlorine,

X represents chlorine, bromine, $C_1$-$C_4$-alkyl or trifluoromethyl,

Y represents hydrogen, $C_1$-$C_4$-alkyl, fluorine, chlorine, bromine, methoxy or trifluoromethyl, Z represents the radical

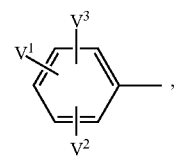

$V^1$ represents hydrogen, fluorine, chlorine, bromine, $C_1$-$C_6$-alkyl, $C_1$-$C_4$-alkoxy, $C_1$-$C_2$-haloalkyl or $C_1$-$C_2$-haloalkoxy, $V^2$ represents hydrogen, fluorine, chlorine, bromine, $C_1$-$C_4$-alkyl or $C_1$-$C_4$-alkoxy, V3 represents hydrogen, fluorine or chlorine, with the proviso that at least one of the radicals W or X represents chlorine or ethyl, CKE represents one of the groups

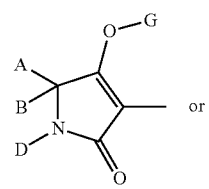 (1)

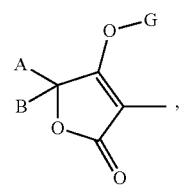 (2)

A represents hydrogen, represents $C_1$-$C_6$-alkyl, $C_1$-$C_4$-alkoxy-$C_1$-$C_2$-alkyl, each of which is optionally mono- to trisubstituted by fluorine and/or chlorine, represents $C_3$-$C_6$-cycloalkyl which is optionally mono- or disubstituted by $C_1$-$C_2$-alkyl or $C_1$-$C_2$-alkoxy and optionally interrupted by an oxygen atom or represents phenyl, pyridyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B represents hydrogen, $C_1$-$C_4$-alkyl or $C_1$-$C_2$-alkoxyl-$C_1$-$C_2$-alkyl or A, B and the carbon atom to which they are attached represent saturated or unsaturated $C_3$-$C_7$-cycloalkyl in which optionally one ring member is replaced by oxygen, nitrogen or sulphur and which is optionally mono- or disubstituted by $C_1$-$C_6$-alkyl, $C_1$-$C_4$-alkoxy-$C_1$-$C_2$-alkyl, trifluoromethyl, $C_1$-$C_6$-alkoxy, $C_3$-$C_6$-alkenyloxy, trifluoroethoxy, $C_1$-$C_3$-alkoxy-$C_1$-$C_3$-alkoxy or $C_3$-$C_6$-cycloalkylmethoxy, where the radicals mentioned above (but not trifluoromethyl) may also be suitable as substituents for nitrogen, A, B and the carbon atom to which they are attached represent $C_5$-$C_6$-cycloalkyl which is substituted by an alkylenediyl group which is optionally substituted by methyl or ethyl and optionally contains one or two not directly adjacent oxygen or sulphur atoms, or by an alkylenedioxyl or by an alkylenedithiol group which, together with the carbon atom to which it is attached, forms a further five-or six-membered ring or A, B and the carbon atom to which they are attached represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, D represents hydrogen, represents $C_1$-$C_6$-alkyl, $C_3$-$C_6$-alkenyl, $C_1$-$C_4$-alkoxy -$C_1$-$C_3$-alkyl, each of which is optionally mono- to trisubstituted by fluorine, represents $C_3$-$C_6$-cycloalkyl which is optionally mono- or disubstituted by $C_1$-$C_4$-alkyl, $C_1$-$C_4$-alkoxy or $C_1$-$C_2$-haloalkyl and in which optionally one methylene group is replaced by oxygen or A and D together represent optionally mono- or disubstituted $C_3$-$C_5$-alkanediyl in which one methylene group may be replaced by oxygen or sulphur, possible substituents being $C_1$-$C_2$-alkyl or $C_1$-$C_2$-alkoxy, or A and D (in the case of the compounds of the formula (I-1)) together with the atoms which they are attached represent one of the groups AD-1 to AD-10:

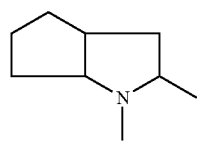

AD-1

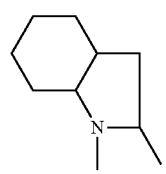

AD-2

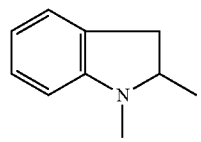

AD-3

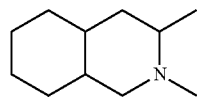

AD-4

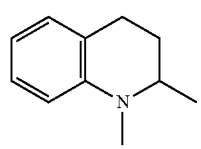

AD-5

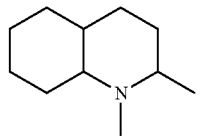

AD-6

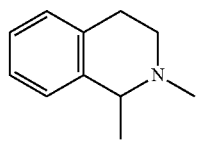

AD-7

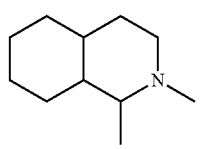

AD-8

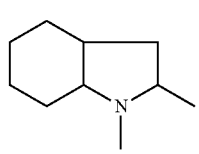

AD-9

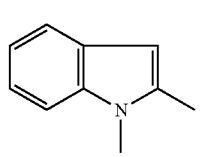

AD-10

G represents hydrogen (a) or represents one of the groups

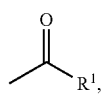

(b)

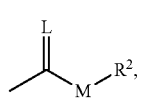

(c)

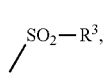

(d)

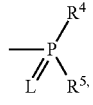

(e)

E or (f)

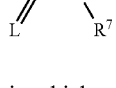

(g)

in which

E represents a metal ion equivalent or an ammonium ion,

L represents oxygen or sulphur and

M represents oxygen or sulphur, $R^1$ represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- or disubtituted by fluorine, chlorine, bromine, cyano, nitro, $C_1$-$C_4$-alkyl, $C_1$-$C_3$-alkoxy, trifluoromethyl or trifluoromethoxy, $R^3$ represents $C_1$-$C_8$-alkyl which is optionally mono- to trisubstituted by fluorine or represents phenyl which is optionally monosubstituted by fluorine, chlorine, bromine, $C_1$-$C_4$-alkyl, $C_1$-$C_4$alkoxy, trifluoromethyl, trifluoromethoxy, cyano or nitro, $R^4$ represents $C_1$-$C_6$-alkyl, $C_1$-$C_6$- alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ represents $C_1$-$C_6$-alkoxy or $C_1$-$C_6$-alkylthio, $R^6$ represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ represents $C_1$-$C_6$-alkyl, $C_3$-$C_6$-alkenyl or $C_1$-$C_6$-alkoxy-$C_1$-$C_4$-alkyl, $R^6$ and $R^7$ together represent a $C_4$-$C_5$-alkylene radical which is optionally substituted by methyl or ethyl and in which optionally one methylene group is replaced by oxygen or sulphur.

4. A compound of the formula (I) according to claim 1 in which

W represents methyl, ethyl or chlorine,
X represents chlorine, methyl or ethyl,
Y represents hydrogen, methyl, fluorine or chlorine,
Z represent the radical

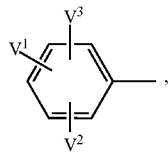

$V^1$ represents hydrogen, fluorine, chlorine, methyl, ethyl, methoxy, ethoxy, trifluoromethyl or trifluoromethoxy,
$V^2$ represents hydrogen, fluorine or chlorine,
V3 represents hydrogen or fluorine,
with the proviso that at least one of the radicals W or X represents chlorine or ethyl, CKE represents one of the groups

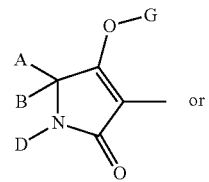 (1)

or

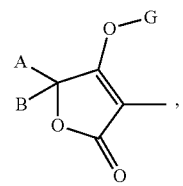 (2)

A represents hydrogen, represents $C_1$-$C_4$-alkyl or $C_1$-$C_2$-alkoxy-$C_1$-$C_2$-alkyl, each of which is optionally mono- or trisubtituted by fluorine, represents cyclopropyl, cyclopentyl or cyclohexyl, represents phenyl which is optionally mono- or disubstituted by fluorine, chlorine, bromine, methyl, ethyl, n-propyl, isopropyl, methoxy, ethoxy, trifluoromethyl, trifluoromethoxy, cyano or nitro, B represents hydrogen, methyl or ethyl or A, B and the carbon atom to which they are attached represents saturated $C_5$-$C_6$-cycloalkyl in which optionally one ring member is replaced by oxygen, nitrogen or sulphur and which is optionally monosubstituted by methyl, ethyl, methoxymethyl, ethoxymethyl, methoxyethyl, ethoxyethyl, trifluoromethyl, methoxy, ethoxy, propoxy, butoxy, methoxyethoxy, ethoxyethoxy, allyloxy, trifluoroethoxy or cyclopropylmethoxy, where the radicals mentioned above (but not trifluoromethyl) are also suitable as substituents of nitrogen, or A, B and the carbon atom to which they are attached represent $C_6$-cycloalkyl, which is optionally substituted by an alkylidenediyl group optionally interrupted by an oxygen atom or by an alkylenedioxy group which contains two not directly adjacent oxygen atoms, where a further 5- or 6-membered ring is formed (which may optionally be mono- or disubstituted by methyl), or A, B and the carbon atom to which they are attached represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, D represents hydrogen, represents $C_1$-$C_4$-alkyl, $C_3$-$C_4$-alkenyl, $C_1$-$C_4$-alkoxy-$C_1$-$C_3$-alkyl, each of which is optionally mono- to trisubstituted by fluorine, or represents cyclopropyl, cyclopentyl or cyclohexyl, or A and D together represent $C_3$-$C_5$-alkanediyl which is optionally monosubstituted by methyl or methoxy and in which optionally one carbon atom is replaced by oxygen or sulphur or represent the group AD-1, G represents hydrogen (a) or represents one of the groups

 (b)

$R^1$,

-continued

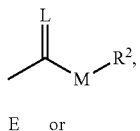

(c)

E or (f)

in which
L represents oxygen or sulphur,
M represents oxygen or sulphur and
E represents a metal ion equivalent or an ammonium ion,
$R^1$ represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy,
$R^2$ represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine.

5. A process for preparing a compound of the formula (I) according to claim 1, comprising
(A) obtaining a compound of formula (I-1-a)

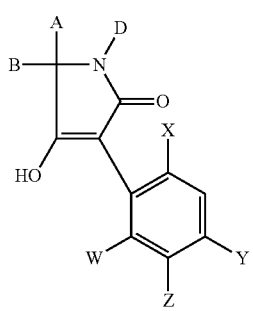

(I-1-a)

in which
A, B, D, W, X, Y and Z are as defined in claim 1,
by the intramolecular condensation of a compound of formula (II)

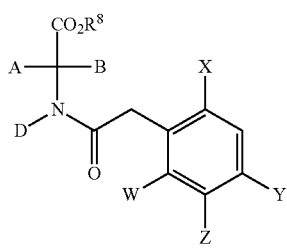

(II)

in which
A, B, D, W, X, Y and Z are as defined in claim 1
and $R^8$ represents alkyl
in the presence of a diluent and in the presence of a base, (B) obtaining a compound of formula (I-2-a)

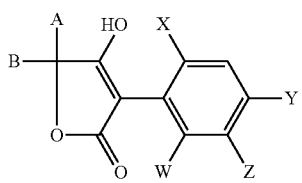

(I-2-a)

in which
A, B, W, X, Y and Z are as defined in claim 1, by the intramolecular condensation of a compound of formula (III)

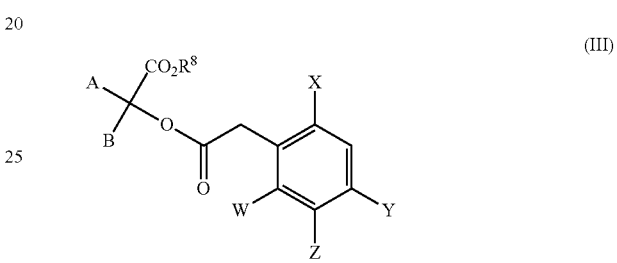

(III)

in which
A, B, W, X, Y, Z are as defined in claim 1 and $R^8$ represents alkyl
in the presence of a diluent and in the presence of a base, (C) obtaining a compound of formulae (I-1-a) to (I-2-g) in which A, B, D, G, W, X, Y and Z are as defined in claim 1

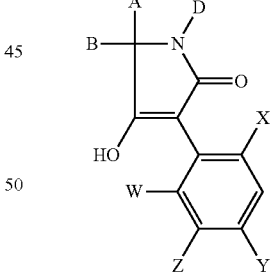

(I-1-a)

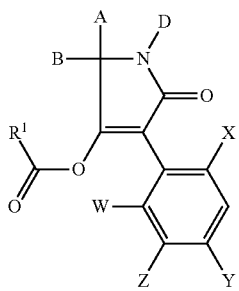

(I-1-b)

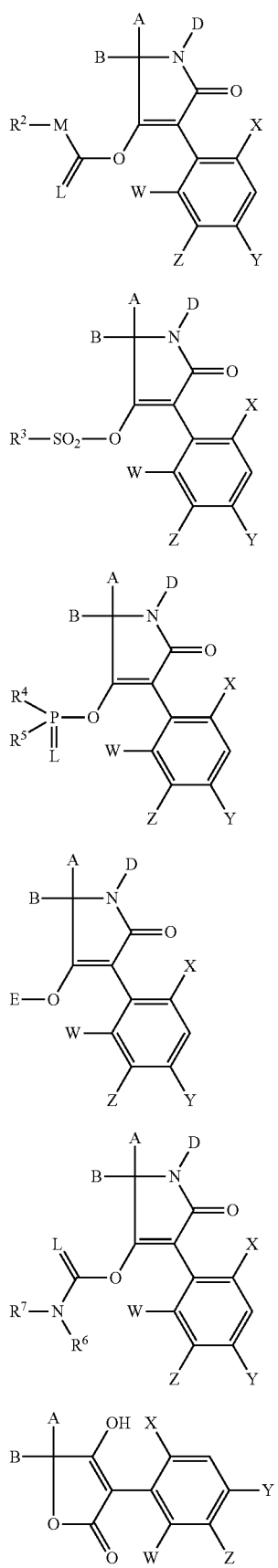
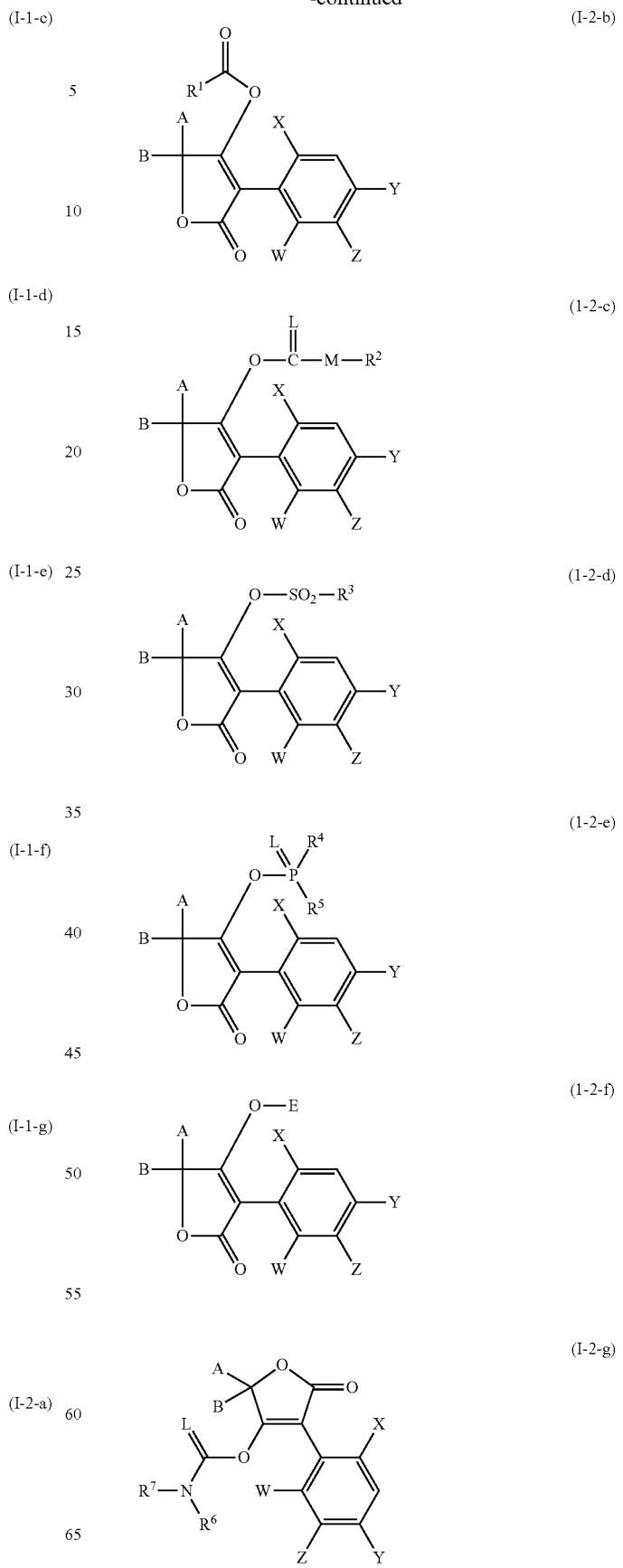

151
by reacting a corresponding compound of formula (I-1'a) to (I-2'-g)
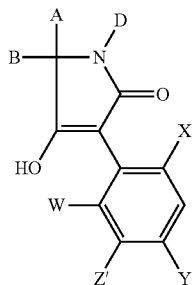
(I-1'-a)
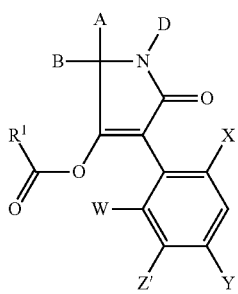
(I-1'-b)
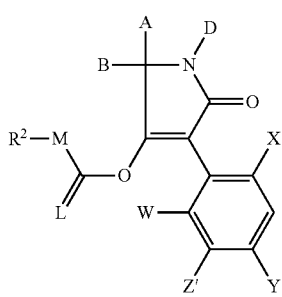
(I-1'-c)
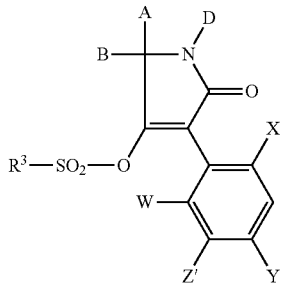
(I-1'-d)
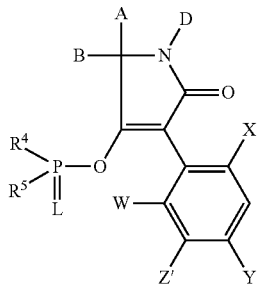
(I-1'-e)
152
-continued
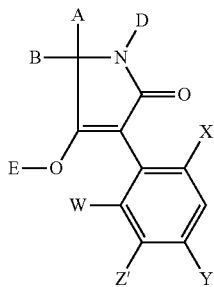
(I-1'-f)
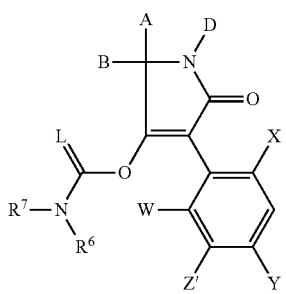
(I-1'-g)
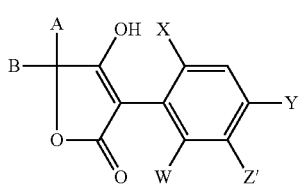
(I-2'-a)
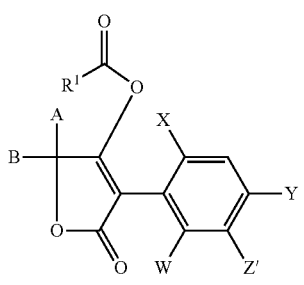
(I-2'-b)
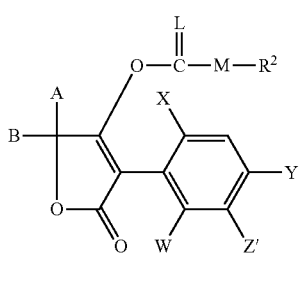
(1-2'-c)
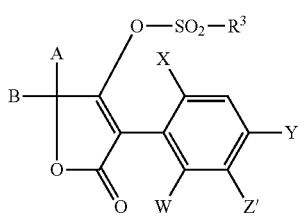
(1-2'-d)

-continued

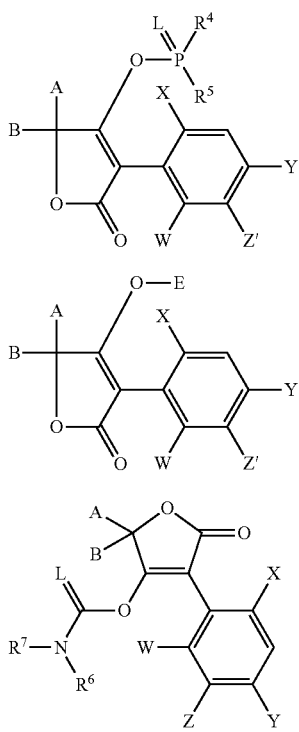

in which
A, B, D, G, W, X and Y are as defined in claim 1 and
Z' represents chlorine, bromine, iodine
with a boronic acid or a boronic acid derivative of formula (IV)

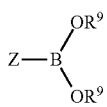

in which
$R^9$ represents hydrogen, $C_1$-$C_6$-alkyl or $C_2$-$C_6$-alkanediyl and
Z is as defined in claim 1
in the presence of a solvent, a base and a catalyst,
(D) obtaining a compound of the formulae (I-1-b) or (1-2-b), by reacting a compound of the formulae (I-1-a) or (I-2-a), respectively, in each case
(α) with an acid halide of formula (V)

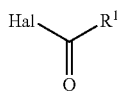

in which
$R^1$ is as defined in claim 1 and
Hal represents halogen
or
(β) with a carboxylic anhydride of formula (VI)

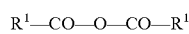

in which
$R^1$ is as defined in claim 1,
optionally in the presence of a diluent and optionally in the presence of an acid binder;
(E) obtaining a compound of the formulae (I-1-c) or (I-2-c) in which L represents oxygen, by reacting a compound of the formulae (I-1-a) or (I-2-a), respectively, in each case
with a chloraformic ester or a chloraformic thioester of formula (VII)

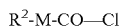

in which
$R^2$ and M are as defined in claim 1,
optionally in the presence of a diluent and optionally in the presence of an acid binder;
(F) obtaining a compound of the formulae (I-1-c) or (I-2-c) in which L represents sulphur, by reacting a compound of the formulae (I-1-a) or (I-2-a), respectively, in each case
with a chloromonothioformic ester or a chlorodithioformic ester of formula (VIII)

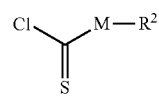

in which
M and $R^2$ are as defined in claim 1,
optionally in the presence of a diluent and optionally in the presence of an acid binder,
(G) obtaining a compound of the formulae (I-1-d) or (I-2-d), by reacting a compound of the formulae (I-1-a) or (I-2-a), respectively, in each case
with a sulphonyl chloride of formula (IX)

in which
$R^3$ is as defined in claim 1,
optionally in the presence of a diluent and optionally in the presence of an acid binder,
(H) obtaining a compound of the formulae (I-1-e) or (I-2-e), by reacting a compound of the formulae (I-1-a) or (I-2-a), respectively, in each case with a phosphorus compound of formula (X)

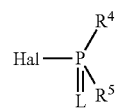

in which
L, $R^4$ and $R^5$ are as defined in claim 1 and
Hal represents halogen,
optionally in the presence of a diluent and optionally in the presence of an acid binder,
(I) obtaining a compound
of the formulae (I-1-f) or (I-2-f), by reacting a compound of the formulae (I-1-a) or (I-2-a), respectively, in each case with a metal compound or an amine of formulae (XI) or (XII),

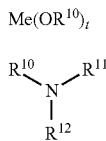

(XI)

(XII)

in which

Me represents a mono- or divalent metal, t represents the number 1 or 2 and $R^{10}$, $R^{11}$, $R^{12}$ independently of one another represent hydrogen or alkyl, optionally in the presence of a diluent, (J) obtaining a compound of the formulae (I-1-g) or (I-2-g), by reacting a compound of the formulae (I-1-a) or (I-2-a), respectively, in each case (α) with an isocyanate or an isothiocyanate of formula (XIII)

(XIII)

in which $R^6$ and L are as defined in claim 1, optionally in the presence of a diluent and optionally in the presence of a catalyst, or (β) with a carbamoyl chloride or a thiocarbamoyl chloride of formula (XIV)

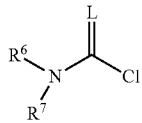

(XIV)

in which

L, $R^6$ and $R^7$ are as defined in claim 1, optionally in the presence of a diluent and optionally in the presence of an acid binder.

6. A pesticide, herbicide, fungicide, or combinations thereof, comprising at least one compound of the formula (I) according to claim 1.

7. A method for controlling animal pests, unwanted vegetation, fungi, or combinations thereof, comprising allowing a compound of the formula (I) according to claim 1 to act on pests, their habitat, or combinations thereof.

8. A process for preparing a pesticide, herbicide, fungicide, or combinations thereof, comprising mixing a compound of the formula (I) according to claim 1 with an extender, a surfactant, or combinations thereof.

9. A composition, comprising an effective amount of an active compound combination comprising, as components, a') at least one compound of the formula (I) according to claim 1 and b') at least one crop plant compatibility-improving compound selected from the following group of compounds:

(i) compounds of the formula (S1)

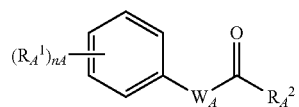

(S1)

in which:

$n_A$ is a natural number from 0 to 5;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group consisting of partially unsaturated or aromatic five-membered heterocycles having 1 to 3 hetero ring atoms selected from the group consisting of N and O, where at least one nitrogen atom and at most one oxygen atom is present in the ring, $R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, which is attached via the nitrogen atom to the carbonyl group in (S1) and which is unsubstituted or substituted by radicals selected from the group consisting of $(C_1-C_4)$-alkyl, $(C_1-C_4)$-alkoxy and optionally substituted phenyl,;

$R_A^3$ is hydrogen or an unsubstituted or substituted aliphatic hydrocarbon radical;

$R_A^4$ is hydrogen, $(C_1-C_6)$-alkyl, $(C_1-C_6)$-alkoxy or substituted or unsubstituted phenyl;

(ii) quinoline derivatives of formula (S2)

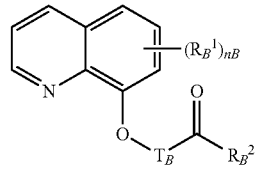

(S2)

in which:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl;

$R_B^3$ is hydrogen or an unsubstituted or substituted aliphatic hydrocarbon radical;

$R_B^4$ is hydrogen, $(C_1-C_6)$-alkyl, $(C_1-C_6)$-alkoxy or substituted or unsubstituted phenyl;

$T_B$ is a $(C_1-$ or $C_2)$-alkanediyl chain which is unsubstituted or substituted by one or two $(C_1-C_4)$-alkyl radicals or by $[(C_1-C_3)$-alkoxy]carbonyl;

(iii) compounds of the formula (S3)

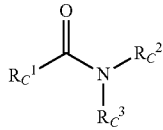

in which:
- $R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl;
- $R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring;

(iv) N-acylsulphonamides of the formula (S4) and their salts

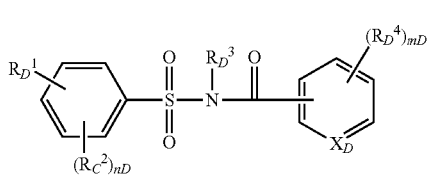

in which:
- $X_D$ is CH or N;
- $R_D^1$ is $CO-NR_D^5R_D^6$ or $NHCO-R_D^7$;
- $R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;
- $R_D^3$ is hydrogen, $(C_1-C_4)$-alkyl, $(C_2-C_4)$-alkenyl or $(C_2-C_4)$-alkynyl;
- $R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;
- $R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
- $R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or
- $R_D^5$ and $R_D^6$ together with the nitrogen atom carrying them form a pyrrolidinyl or piperidinyl radical;
- $R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
- $n_D$ is 0, 1 or 2;
- $m_D$ is 1 or 2;
- $v_D$ is 0, 1, 2 or 3;

(v) active compounds from the class of hydroxyaromatics and aromatic-aliphatic carboxylic acid derivatives of formula (S5);

(vi) active compounds from the class of 1,2-dihydroquinoxalin-2-ones of formula (S6);

(vii) compounds of formula (S7),

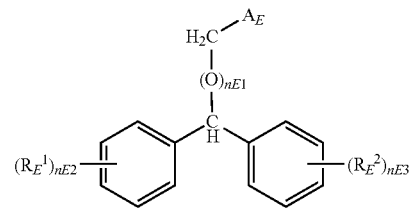

in which:
- $R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
- $A_E$ is $COOR_E^3$ or $COSR_E^4$;
- $R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium,
- $n_E^1$ is 0 or 1;
- $n_E^2$, $n_E^3$ independently of one another are 0, 1 or 2;

(viii) compounds of formula (S8),

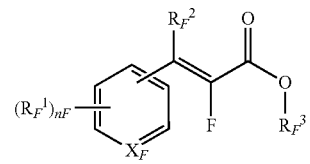

in which
- $X_F$ is CH or N,
- $n_F$ is, if $X_F=N$, an integer from 0 to 4 and is, if $X_F=CH$, an integer from 0 to 5,
- $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy,
- $R_F^2$ is hydrogen or $(C_1-C_4)$-alkyl,
- $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or moreidentical or different radicals from the group consisting of halogen and alkoxy; or salts thereof;
(ix) compounds from the class of 3-(5-tetrazolylcarbonyl)-2-quinolones of formula (S9);
(x) compounds of formula (S10$^a$) or (S10$^b$)

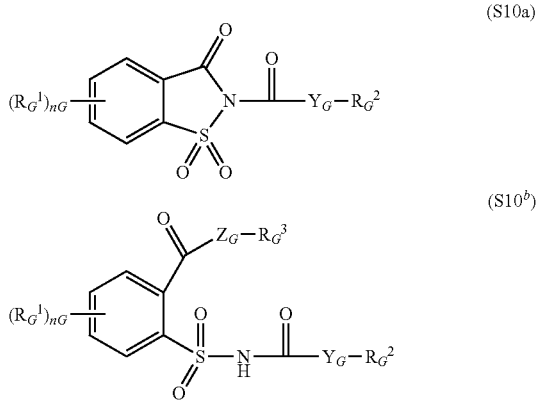

in which
$R_G^1$ is halogen, $(C_1-C_4)$-alkyl, methoxy, nitro, cyano, $CF_3$, $OCF_3$;
$Y_G$, $Z_G$ independently of one another are O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl, benzyl, halobenzyl,
$R_G^3$ is hydrogen or $(C_1-C_6)$-alkyl;
(xi) compounds of the type of oxyimino compounds of formula (S11);
(xii) compounds from class of the isothiochromanones (S12);
(xiii) a compound selected from the group consisting of naphthalic anhydride, fenclorim, flurazole, CL-304415, MG-191, MG-838, disulfoton, dietholate and mephanate;
(xiv) compounds selected from the group consisting of safeners;
(xv) a compound of formula (S15) or a tautomer thereof

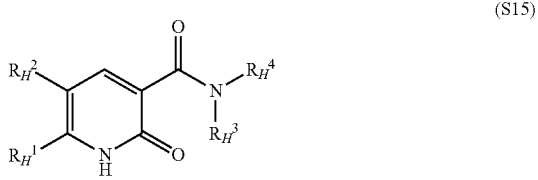

in which
$R_H^1$ represents a $(C_1-C_6)$haloalkyl radical and
$R_H^2$ represents hydrogen or halogen and
$R_H^3$, $R_H^4$ independently of one another represent hydrogen, $(C_1-C_{16})$-alkyl, $(C_2-C_{16})$-alkenyl or $(C_2-C_{16})$-alkynyl,
where each of the 3 last-mentioned radicals is unsubstituted or substituted by one or more radicals from the group consisting of halogen, hydroxy, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl, which is unsubstituted or substituted, phenyl, which is unsubstituted or substituted, and heterocyclyl, which is unsubstituted or substituted,
or $(C_3-C_6)$-cycloalkyl, $(C_4-C_6)$-cycloalkenyl, $(C_3-C_6)$-cycloalkyl which is condensed on one side of the ring to a 4- to 6-membered saturated or unsaturated carbocyclic ring, or $(C_4-C_6)$-cycloalkenyl which is condensed on one side of the ring to a 4- to 6-membered saturated or unsaturated carbocyclic ring,
where each of the 4 last-mentioned radicals is unsubstituted or substituted by one or more radicals from the group consisting of halogen, hydroxy, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl, which is unsubstituted or substituted, phenyl, which is unsubstituted or substituted, and heterocyclyl, which is unsubstituted or substituted,
or
$R_H^3$ represents $(C_1-C_4)$-alkoxy, $(C_2-C_4)$-alkenyloxy, $(C_2-C_6)$-alkinyloxy or $(C_2-C_4)$-haloalkoxy and
$R_H^4$ represents hydrogen or $(C_1-C_4)$-alkyl or
$R_H^3$ and $R_H^4$ together with the directly attached nitrogen atom represent a 4- to 8-membered heterocyclic ring which, in addition to the nitrogen atom, may also contain further hetero ring atoms, and which is unsubstituted or substituted by one or more radicals from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio; or
(xvi) compounds which are primarily used as herbicides, but also have safener effect on crop plants.

10. A method for controlling unwanted vegetation, comprising allowing a composition according to claim 9 to act on the plants or their environment.

11. A method for controlling unwanted vegetation, comprising allowing a compound of the formula (I) according to claim 1 and a crop plant compatibility-improving compound selected from
(i) compounds of the formula (S1)

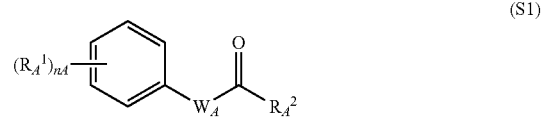

in which:
$n_A$ is a natural number from 0 to 5;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group consisting of partially unsaturated or aromatic five-membered heterocycles having 1 to 3 hetero ring atoms selected from the group consisting of N and O, where at least one nitrogen atom and at most one oxygen atom is present in the ring,
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, which is attached via the nitrogen atom to the carbonyl group in (S1) and which is unsubstituted or substituted by radicals selected from the group consisting of $(C_1-C_4)$-alkyl, $(C_1-C_4)$-alkoxy and optionally substituted phenyl,;

$R_A^3$ is hydrogen or an unsubstituted or substituted aliphatic hydrocarbon radical;

$R_A^4$ is hydrogen, $(C_1-C_6)$-alkyl, $(C_1-C_6)$-alkoxy or substituted or unsubstituted phenyl;

(ii) quinoline derivatives of formula (S2)

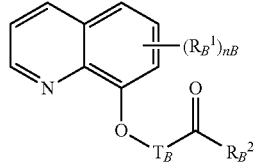

(S2)

in which:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl;

$R_B^3$ is hydrogen or an unsubstituted or substituted aliphatic hydrocarbon radical;

$R_B^4$ is hydrogen, $(C_1-C_6)$-alkyl, $(C_1-C_6)$-alkoxy or substituted or unsubstituted phenyl;

$T_B$ is a $(C_1$- or $C_2)$-alkanediyl chain which is unsubstituted or substituted by one or two $(C_1-C_4)$-alkyl radicals or by $[(C_1-C_3)$-alkoxy]carbonyl;

(iii) compounds of the formula (S3)

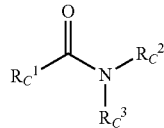

(S3)

in which:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together foul a substituted or unsubstituted heterocyclic ring;

(iv) N-acylsulphonamides of the formula (S4) and their salts

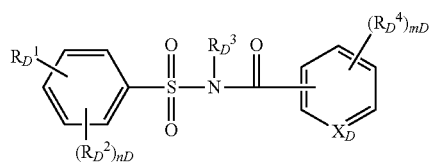

(S4)

in which:

$X_D$ is CH or N;

$R_D^1$ is $CO-NR_D^5R_D^6$ or $NHCO-R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

(v) active compounds from the class of hydroxyaromatics and aromatic-aliphatic carboxylic acid derivatives of formula (S5);

(vi) active compounds from the class of 1,2-dihydroquinoxalin-2-ones of formula (S6);

(vii) compounds of formula (S7),

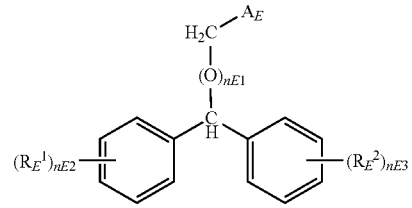

(S7)

in which:

$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ is $COOR_E^3$ or $COSR_E^4$;

$R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1;

$n_E^2$, $n_E^3$ independently of one another are 0, 1 or 2;

(viii) compounds of formula (S8),

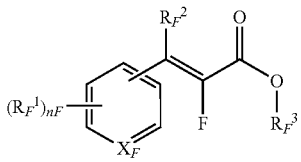
(S8)

in which $X_F$ is CH or N, $n_F$ is, if $X_F$=N, an integer from 0 to 4 and
is, if $X_F$=CH, an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or moreidentical or different radicals from the group consisting of halogen and alkoxy; or salts thereof;

(ix) compounds from the class of 3-(5-tetrazolylcarbonyl)-2-quinolones of formula (S9);

(x) compounds of formula (S10$^a$) or (S10$^b$)

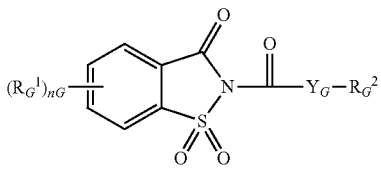
(S10a)

(S10b)

in which $R_G^1$ is halogen, $(C_1-C_4)$-alkyl, methoxy, nitro, cyano, $CF_3$, $OCF_3$;

$Y_G$, $Z_G$ independently of one another are O or S, $n_G$ is an integer from 0 to 4, $R_G^2$ is $(C_1-C_{16})$-alkyl, $(C_2-C_6)$-alkenyl, $(C_3-C_6)$-cycloalkyl, aryl, benzyl, halobenzyl, $R_G^3$ is hydrogen or $(C_1-C_6)$-alkyl;

(xi) compounds of the type of oxyimino compounds of formula (S11);

(xii) compounds from class of the isothiochromanones (S12);

(xiii) a compound selected from the group consisting of naphthalic anhydride, fenclorim, flurazole, CL-304415, MG-191, MG-838, disulfoton, dietholate and mephanate;

(xiv) compounds selected from the group consisting of safeners;

(xv) a compound of formula (S15) or a tautomer thereof

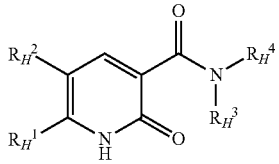
(S15)

in which $R_H^1$ represents a $(C_1-C_6)$haloalkyl radical and $R_H^2$ represents hydrogen or halogen and $R_H^3$, $R_H^4$ independently of one another represent hydrogen, $(C_1-C_{16})$-alkyl, $(C_2-C_{16})$-alkenyl or $(C_2-C_{16})$-alkynyl, where each of the 3 last-mentioned radicals is unsubstituted or substituted by one or more radicals from the group consisting of halogen, hydroxy, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl, which is unsubstituted or substituted, phenyl, which is unsubstituted or substituted, and heterocyclyl, which is unsubstituted or substituted, or $(C_3-C_6)$-cycloalkyl, $(C_4-C_6)$-cycloalkenyl, $(C_3-C_6)$-cycloalkyl which is condensed on one side of the ring to a 4- to 6-membered saturated or unsaturated carbocyclic ring, or $(C_4-C_6)$-cycloalkenyl which is condensed on one side of the ring to a 4- to 6-membered saturated or unsaturated carbocyclic ring, where each of the 4 last-mentioned radicals is unsubstituted or substituted by one or more radicals from the group consisting of halogen, hydroxy, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl, which is unsubstituted or substituted, phenyl, which is unsubstituted or substituted, and heterocyclyl, which is unsubstituted or substituted, or $R_H^3$ represents $(C_1-C_4)$-alkoxy, $(C_2-C_4)$-alkenyloxy, $(C_2-C_6)$-alkinyloxy or $(C_2-C_4)$-haloalkoxy and $R_H^4$ represents hydrogen or $(C_1-C_4)$-alkyl or $R_H^3$ and $R_H^4$ together with the directly attached nitrogen atom represent a 4- to 8-membered heterocyclic ring which, in addition to the nitrogen atom, may also contain further hetero ring atoms, and which is unsubstituted or substituted by one or more radicals from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio; or (xvi) compounds which are primarily used as herbicides, but also have safener effect on crop plants, to act separately, in close temporal succession, on the plants or their environment.

12. A composition, comprising
at least one compound of the formula (I) according to claim 1 and
at least one salt of formula (III')

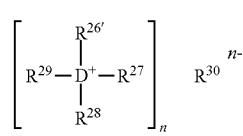
(III')

in which

D represents nitrogen or phosphorus, $R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, where the substituents may be selected from the group consisting of halogen, nitro and cyano, n represents 1, 2, 3 or 4, and $R^{30}$ represents an inorganic or organic anion.

13. A composition according to claim 12, further comprising at least one penetrant.

14. A method for enhancing the action of a pesticide, a herbicide, or a fungicide, or combinations thereof, comprising preparing a ready-to-use (spray liquor) composition comprising an active compound of the formula (I) according to claim 1 and a salt of the fonnula (III')

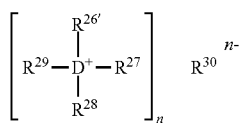

(III')

in which

D represents nitrogen or phosphorus, $R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, where the substituents may be selected from the group consisting of halogen, nitro and cyano, n represents 1, 2, 3 or 4, and $R^{30}$ represents an inorganic or organic anion.

15. A method according to claim 14, comprising preparing the spray liquor using a penetrant.

16. A compound of formula (I-1'-a)

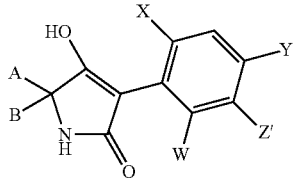

(I-1'-a)

in which W, X, Y, Z', A and B have the meanings below

| W | X | Y | Z' | A | B |
|---|---|---|----|---|---|
| $C_2H_5$ | $C_2H_5$ | H | Br | —(CH$_2$)$_2$—CHOCH$_3$—(CH$_2$)$_2$— | |
| $C_2H_5$ | $C_2H_5$ | H | Br | —(CH$_2$)$_2$—O—(CH$_2$)$_2$— | |
| Cl | Cl | H | Br | —(CH$_2$)$_2$—O—(CH$_2$)$_2$—. | |

17. A composition, comprising a composition according to claim 9 and at least one salt of formula (III')

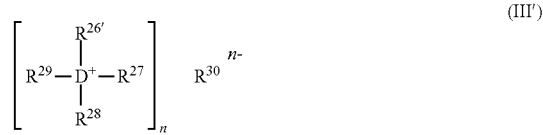

(III')

in which

D represents nitrogen or phosphorus, $R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, where the substituents may be selected from the group consisting of halogen, nitro and cyano, n represents 1, 2, 3 or 4, and $R^{30}$ represents an inorganic or organic anion.

18. A method for enhancing the action of a pesticide, a herbicide, or a fungicide, or combinations thereof, comprising preparing a ready-to-use (spray liquor) composition comprising a composition according to claim 9, and a salt of the formula (III')

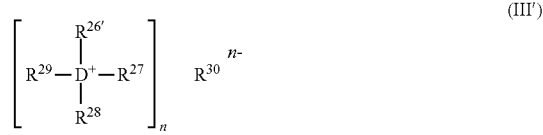

(III')

in which

D represents nitrogen or phosphorus, $R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$alkylene, where the substituents may be selected from the group consisting of halogen, nitro and cyano, n represents 1, 2, 3 or 4, and $R^{30}$ represents an inorganic or organic anion.

* * * * *